US011491239B2

(12) United States Patent
Barbieri et al.

(10) Patent No.: US 11,491,239 B2

(45) Date of Patent: Nov. 8, 2022

(54) MODIFIED CLOSTRIDIAL NEUROTOXINS AS VACCINES AND CONJUGATE VACCINE PLATFORMS

(71) Applicants: THE MEDICAL COLLEGE OF WISCONSIN, INC., Milwaukee, WI (US); WISCONSIN ALUMNI RESEARCH FOUNDATION, Madison, WI (US)

(72) Inventors: Joseph T. Barbieri, New Berlin, WI (US); Eric A. Johnson, Milwaukee, WI (US); Sabine Pellett, Milwaukee, WI (US); William H. Tepp, Milwaukee, WI (US); Amanda Przedpelski, Milwaukee, WI (US)

(73) Assignees: The Medical College of Wisconsin, Inc., Milwaukee, WI (US); Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 16/772,590

(22) PCT Filed: Dec. 17, 2018

(86) PCT No.: PCT/US2018/066033

§ 371 (c)(1),
(2) Date: Jun. 12, 2020

(87) PCT Pub. No.: WO2019/118974

PCT Pub. Date: Jun. 20, 2019

(65) Prior Publication Data

US 2020/0384120 A1 Dec. 10, 2020

Related U.S. Application Data

(60) Provisional application No. 62/599,444, filed on Dec. 15, 2017.

(51) Int. Cl.

| | |
|---|---|
| ***A61K 39/395*** | (2006.01) |
| ***A61K 47/68*** | (2017.01) |
| ***A61K 47/55*** | (2017.01) |
| ***A61K 39/00*** | (2006.01) |
| ***A61K 39/08*** | (2006.01) |
| ***C12N 15/10*** | (2006.01) |

(52) U.S. Cl.

CPC ...... *A61K 47/6829* (2017.08); *A61K 39/0015* (2013.01); *A61K 39/08* (2013.01); *A61K 47/55* (2017.08); *C12N 15/102* (2013.01); *C07K 2319/55* (2013.01)

(58) Field of Classification Search

None

See application file for complete search history.

(56) References Cited

U.S. PATENT DOCUMENTS

2005/0238663 A1 10/2005 Hunt
2008/0221012 A1* 9/2008 Steward ................ C07K 14/33 536/23.7
2011/0318385 A1* 12/2011 Jackson ................ C07K 14/33 536/23.7

OTHER PUBLICATIONS

Ngo et al, The protein Folding Problem and Tertiary Structure, Ch 14, p. 492-494 (Year: 1994).*

Zuverink et al., Infection and Immunity, vol. 83, No. 7, p. 27214-2724 (Year: 2015).*

Travassos, L. R.; et al., Linear Epitopes of Paracoccidioides brasiliensis and Other Fungal Agents of Human Systemic Mycoses as Vaccine Candidates Front Immunol 2017, 8, 224.

Van Nuffel, A. M.; et al., Intravenous and intradermal TriMix-dendritic cell therapy results in a broad T-cell response and durable tumor response in a chemorefractory stage IV-M1c melanoma patient. Cancer Immunol Immunother 2012, 61 (7), 1033-43.

Wang, N. Y.; et al., The next chapter for group B meningococcal vaccines. Crit Rev Microbiol 2017, 1-17.

Wang, Y.; et al., Effectiveness and practical uses of 23-valent pneumococcal polysaccharide vaccine in healthy and special populations. Hum Vaccin Immunother 2017, 1-10.

Webb, R. P.; et al., Recombinant Botulinum Neurotoxin Hc Subunit (BoNT Hc) and Catalytically Inactive Clostridium botulinum Holoproteins (ciBoNT HPs) as Vaccine Candidates for the Prevention of Botulism. Toxins (Basel) 2017, 9 (9).

Webb, R.P., et al. (2009). Production of catalytically inactive BoNT/A1 holoprotein and comparison with BoNT/A1 subunit vaccines against toxin subtypes A1, A2, and A3. Vaccine 27, 4490-4497.

Webb, R.P., et al. (2013). What next for botulism vaccine development? Expert Rev Vaccines 12, 481-492.

Weisemann, J.; et al., Botulinum Neurotoxin Serotype A Recognizes Its Protein Receptor SV2 by a Different Mechanism than Botulinum Neurotoxin B Synaptotagmin. Toxins (Basel) 2016, 8 (5).

(Continued)

*Primary Examiner* — Yunsoo Kim

(74) *Attorney, Agent, or Firm* — Quarles & Brady LLP

(57) ABSTRACT

Provided herein are engineered non-catalytic, non-toxic tetanus toxin variants and methods of using such engineered tetanus toxin variants as low dose, protective vaccines that are non-toxic and more potent than their respective chemically inactivated toxoids. In addition, provided herein are conjugate vaccine carriers comprising engineered tetanus toxin variants and methods of using such conjugate vaccines to elicit T-cell dependent immune memory responses which can target a broad spectrum of microbial pathogens as a single vaccine.

9 Claims, 15 Drawing Sheets

Specification includes a Sequence Listing.

(56) References Cited

OTHER PUBLICATIONS

Whitemarsh, R.C., et al. (2012). Novel application of human neurons derived from induced pluripotent stem cells for highly sensitive botulinum neurotoxin detection. Toxicol Sci 126, 426-435.
Whitemarsh, R.C., et al. (2013). Characterization of Botulinum Neurotoxin A Subtypes 1 Through 5 by Investigation of Activities in Mice, Neuronal Cell Cultures, and In Vitro. Infect Immun 81, 3894-3902.
Woldeamanuel, Y. W., Tetanus in Ethiopia: unveiling the blight of an entirely vaccine-preventable disease. Curr Neurol Neurosci Rep 2012, 12 (6), 655-65.
World Health Organization. (2017). Tetanus vaccines: WHO position paper-Feb. 2017. Weekly Epidemiological Record. 92(6), 53-76.
World Health Organization. Tetanus vaccines: WHO position paper, Feb. 2017—Recommendations. Vaccine 2018, 36 (25), 3573-3575.
Xu, Q., et al. (2009). An adenoviral vector-based mucosal vaccine is effective in protection against botulism. Gene Ther 16, 367-375.
Yu, Y.Z., et al. (2014). Pentavalent replicon vaccines against botulinum neurotoxins and tetanus toxin using DNA-based Semliki Forest virus replicon vectors. Hum Vaccin Immunother 10, 1874-1879.
Zhang, G.L. et al., Synthetic Glycans and Glycomimetics: A Promising Alternative to Natural Polysaccharides. Chemistry 2017.
Zuverink, M.; et al., A Heterologous Reporter Defines the Role of the Tetanus Toxin Interchain Disulfide in Light-Chain Translocation. Infect Immun 2015, 83 (7), 2714-24.
Przedpelski, A., et al. "A novel high-potency tetanus vaccine." Mbio 11.4 (2020): e01668-20.
Agarwal, R.; et al., Structural analysis of botulinum neurotoxin serotype F light chain: implications on substrate binding and inhibitor design. Biochemistry 2005, 44 (35), 11758-65.
Agnolon, V.; et al., The potential of adjuvants to improve immune responses against TdaP vaccines: A preclinical evaluation of MF59 and monophosphoryl lipid A. Int J Pharm 2015, 492 (1-2), 169-76.
Atassi, M.Z., et al. (2011). Regions of botulinum neurotoxin A light chain recognized by human anti-toxin antibodies from cervical dystonia patients immunoresistant to toxin treatment. The antigenic structure of the active toxin recognized by human antibodies. Immunobiology 216, 782-792.
Baldwin, M.R., et al. (2008). Subunit vaccine against the seven serotypes of botulism. Infect Immun 76, 1314-1318.
Bayart, C., et al. "The combined use of analytical tools for exploring tetanus toxin and tetanus toxoid structures." Journal of Chromatography B 1054 (2017): 80-92.
Berntsson, R. P.; et al., Structure of dual receptor binding to botulinum neurotoxin B. Nat Commun 2013, 4, 2058.
Blum, F. C.; et al., Entry of a recombinant, full-length, atoxic tetanus neurotoxin into Neuro-2a cells. Infect Immun 2014, 82 (2), 873-81.
Blum, F. C.; et al.. Multiple domains of tetanus toxin direct entry into primary neurons. Traffic 2014, 15 (10), 1057-65.
Broker, M.; et al., Polysaccharide conjugate vaccine protein carriers as a "neglected valency" —Potential and limitations. Vaccine 2017, 35 (25), 3286-3294.
Burns, J. R. Mechanisms of clostridial neurotoxin binding and entry. Diss. University of Missouri—Columbia, 2016.
Byrne, M.P., et al. (2000). Development of vaccines for prevention of botulism. Biochimie 82, 955-966.
Centers for Disease Control and Prevention (CDC. "Notice of CDC's discontinuation of investigational pentavalent (ABCDE) botulinum toxoid vaccine for workers at risk for occupational exposure to botulinum toxins." MMWR. Morbidity and mortality weekly report 60.42 (2011): 1454.
Centers for Disease Control and Prevention. Impact of vaccines universally recommended for children-United States, 1990-1998. MMWR Morb Mortal Wkly Rep 1999, 48 (12), 243-8.
Centers for Disease Control and Prevention. Thimerosal in vaccines: a joint statement of the American Academy of Pediatrics and the Public Health Service. MMWR Morb Mortal Wkly Rep 1999, 48 (26), 563-5.
Chen, C.; et al., Gangliosides as high affinity receptors for tetanus neurotoxin. J Biol Chem 2009, 284 (39), 26569-77.
Chen, S.; et al., Insights into the different catalytic activities of Clostridium neurotoxins. Biochemistry 2012, 51 (18), 3941-7.
Chen, S.; et al., Mechanism of substrate recognition by botulinum neurotoxin serotype A. J Biol Chem 2007, 282 (13), 9621-7.
Chen, S.; et al., Multiple pocket recognition of SNAP25 by botulinum neurotoxin serotype E. J Biol Chem 2007, 282 (35), 25540-7.
Cheng, L.W., et al. (2009). Antibody protection against botulinum neurotoxin intoxication in mice. Infect Immun 77, 4305-4313.
Chu, C., et al. "Further studies on the immunogenicity of Haemophilus influenzae type b and pneumococcal type 6A polysaccharide-protein conjugates." Infection and Immunity 40.1 (1983): 245-256.
Clapp, B., et al. (2010). Adenovirus F protein as a delivery vehicle for botulinum B. BMC Immunol 11, 36.
Clayton, M. A.; et al., Protective vaccination with a recombinant fragment of Clostridium botulinum neurotoxin serotype A expressed from a synthetic gene in *Escherichia coli*. Infect Immun 1995, 63 (7), 2738-42.
Cohn, A. C.; et al., Effectiveness and Duration of Protection of One Dose of a Meningococcal Conjugate Vaccine. Pediatrics 2017, 139 (2).
Di Bello, I.C., et al. (1994). Antagonism of the intracellular action of botulinum neurotoxin type A with monoclonal antibodies that map to light-chain epitopes. Eur J Biochem 219, 161-169.
Dolimbek, B.Z., et al. (2007). Mapping of the regions on the heavy chain of botulinum neurotoxin A (BoNT/A) recognized by antibodies of cervical dystonia patients with immunoresistance to BoNT/A. Mol Immunol 44, 1029-1041.
Dolimbek, G. S.; et al., Mapping of the antibody and T cell recognition profiles of the HN domain (residues 449-859) of the heavy chain of botulinum neurotoxin A in two high-responder mouse strains. Immunol Invest 2005, 34 (2), 119-42.
Drake, J. W.; et al., Rates of spontaneous mutation. Genetics 1998, 148 (4), 1667-86.
Dressler, D., Botulinum toxin drugs: brief history and outlook. J Neural Transm (Vienna) 2016, 123 (3), 277-9.
Fan, Y.; et al., A three monoclonal antibody combination potently neutralizes multiple botulinum neurotoxin serotype F subtypes. PLoS One 2017, 12 (3), e0174187.
Feikin, D. R.; et al., Randomized trial of the quantitative and functional antibody responses to a 7-valent pneumococcal conjugate vaccine and/or 23-valent polysaccharide vaccine among HIV-infected adults. Vaccine 2001, 20 (3-4), 545-53.
Fu, Z.; et al., Glycosylated SV2 and gangliosides as dual receptors for botulinum neurotoxin serotype F. Biochemistry 2009, 48 (24), 5631-41.
Garcia-Rodriguez, C., et al. (2011). Neutralizing human monoclonal antibodies binding multiple serotypes of botulinum neurotoxin. Protein Eng Des Sel 24, 321-331.
Gill, D. M., Bacterial toxins: a table of lethal amounts. Microbiol Rev 1982, 46 (1), 86-94.
Gu, S., et al. (2012). Botulinum neurotoxin is shielded by NTNHA in an interlocked complex. Science 335, 977-981.
Guazzelli, L.; et al., Synthesis of part structures of Cryptococcus neoformans serotype C capsular polysaccharide. Carbohydr Res 2016, 433, 5-13.
Halliwell, G., The action of proteolytic enzymes on Clostridium botulinum type A toxin. Biochem J 1954, 58 (1), 4-8.
Halperin, B. A.; et al., Kinetics of the antibody response to tetanus-diphtheria-acellular pertussis vaccine in women of childbearing age and postpartum women. Clin Infect Dis 2011, 53 (9), 885-92.
Hill, K.K., et al. (2007). Genetic diversity among Botulinum Neurotoxin-producing clostridial strains. Journal of bacteriology 189, 818-832.
International Searching Authority. International Search Report and Written Opinion for application PCT/US2018/066033. dated Jul. 10, 2019. 15 pages.

(56) References Cited

OTHER PUBLICATIONS

Isturiz, R. E.; et al., Pneumococcal conjugate vaccine use for the prevention of pneumococcal disease in adults <50 years of age. Expert Rev Vaccines 2017, 1-11.
Jacobson, M.J., et al. (2011). Purification, Modeling and Analysis of Neurotoxin BoNT/A5 from Clostridium botulinum Strain A661222. Applied and Environmental Microbiology.
Johnson, B. D.; et al., Graft-vs.-host and graft-vs.-leukemia reactions after delayed infusions of donor T-subsets. Biol Blood Marrow Transplant 1999, 5 (3), 123-32.
Johnson, E. A., et al. "Botulism." Handbook of clinical neurology 91 (2008): 333-368. (In two parts due to file size).
Keller, J. E., Characterization of new formalin-detoxified botulinum neurotoxin toxoids. Clin Vaccine Immunol 2008, 15 (9), 1374-9.
Killeen, K. P.; et al., Reversion of recombinant toxoids: mutations in diphtheria toxin that partially compensate for active-site deletions. Proc Natl Acad Sci U S A 1992, 89 (13), 6207-9.
Klein, N. P.; et al., Immunogenicity and safety of the Haemophilus influenzae type b and Neisseria meningitidis serogroups C and Y-tetanus toxoid conjugate vaccine co-administered with human rotavirus, hepatitis A and 13-valent pneumococcal conjugate vaccines: results from a phase III, randomized, multicenter study in infants. Hum Vaccin Immunother 2018, 1-12.
Kobayashi, R., et al. (2005). A novel neurotoxoid vaccine prevents mucosal botulism. J Immunol 174, 2190-2195.
Koepke, R.; et al., Global occurrence of infant botulism, 1976-2006. Pediatrics 2008, 122 (1), e73-82.
Kumai, T.; et al., Optimization of Peptide Vaccines to Induce Robust Antitumor CD4 T-cell Responses. Cancer Immunol Res 2017, 5 (1), 72-83.
Lacy, D. B.; et al., Sequence homology and structural analysis of the clostridial neurotoxins. Journal of molecular biology 1999, 291 (5), 1091-104.
Lam, K.H., et al. (2015). Diverse binding modes, same goal: The receptor recognition mechanism of botulinum neurotoxin. Prog Biophys Mol Biol 117, 225-231.
Lapenotiere, H.F., et al. (1995). Expression of a large, nontoxic fragment of botulinum neurotoxin serotype A and ts use as an immunogen. Toxicon : official journal of the International Society on Toxinology 33, 1383-1386.
Lees, A.; et al., Activation of soluble polysaccharides with 1-cyano-4-dimethylaminopyridinium tetrafluoroborate for use in protein-polysaccharide conjugate vaccines and immunological reagents. Vaccine 1996, 14 (3), 190-8.
Li, J., et al. (2015). Intranasal vaccination with an engineered influenza virus expressing the receptor binding subdomain of botulinum neurotoxin provides protective immunity against botulism and influenza. Front Immunol 6, 170.
Lin, G., et al. (2010). Expression of the Clostridium botulinum A2 neurotoxin gene cluster proteins and characterization of the A2 complex. Applied and Environmental Microbiology 76, 40-47.
Lou, J.; et al., A Single Tri-Epitopic Antibody Virtually Recapitulates the Potency of a Combination of Three Monoclonal Antibodies in Neutralization of Botulinum Neurotoxin Serotype A. Toxins (Basel) 2018, 10 (2).
Lou, J.; et al., Affinity maturation of human botulinum neurotoxin antibodies by light chain shuffling via yeast mating. Protein Eng Des Sel 2010, 23 (4), 311-9.
Malizio, C.J., et al. (2000). Purification of Clostridium botulinum type A neurotoxin. Methods in molecular biology (Clifton, NJ) 145, 27-39.
Masuyer, G.; et al., The structure of the tetanus toxin reveals pH-mediated domain dynamics. EMBO Rep 2017, 18 (8), 1306-1317.
Mayer, S.; et al., Analysis of the immune response against tetanus toxoid: enumeration of specific T helper cells by the Elispot assay. Immunobiology 2002, 205 (3), 282-9.
Mcguirk, P.; et al., Pathogen-specific regulatory T cells provoke a shift in the Th1/Th2 paradigm in immunity to infectious diseases. Trends Immunol 2002, 23 (9), 450-5.
Montal, M. "Botulinum neurotoxin: a marvel of protein design." Annual review of biochemistry 79 (2010): 591-617.
Montecucco, C., et al. (1993). Tetanus and botulism neurotoxins: a new group of zinc proteases. Trends in biochemical sciences 18, 324-327.
Montecucco, C., et al. (2004). Presynaptic receptor arrays for clostridial neurotoxins. Trends in microbiology 12, 442-446.
Moyron-Quiroz, J. E.; et al., The smallpox vaccine induces an early neutralizing IgM response. Vaccine 2009, 28 (1), 140-7.
Mustafa, W., et al. (2011). Immunization of mice with the non-toxic HC50 domain of botulinum neurotoxin presented by rabies virus particles induces a strong immune response affording protection against high-dose botulinum neurotoxin challenge. Vaccine 29, 4638-4645.
Nabel, G. J., Designing tomorrow's vaccines. N Engl J Med 2013, 368 (6), 551-60.
Needleman, S. B., et al. "A general method applicable to the search for similarities in the amino acid sequence of two proteins." Journal of molecular biology 48.3 (1970): 443-453.
Nencioni, L.; et al., Properties of pertussis toxin mutant PT-9K/129G after formaldehyde treatment. Infect Immun 1991, 59 (2), 625-30.
Oshima, M.; et al., Immune recognition of botulinum neurotoxin type A: regions recognized by T cells and antibodies against the protective H(C) fragment (residues 855-1296) of the toxin. Mol Immunol 1997, 34 (14), 1031-40.
Payne, J. R.; et al., Efficacy of Human Botulism Immune Globulin for the Treatment of Infant Botulism: The First 12 Years Post Licensure. J Pediatr 2017.
Pellett, S., et al. (2007). A neuronal cell-based botulinum neurotoxin assay for highly sensitive and specific detection of neutralizing serum antibodies. FEBS letters 581, 4803-4808.
Pellett, S., et al. (2010). Comparison of the primary rat spinal cord cell (RSC) assay and the mouse bioassay for botulinum neurotoxin type A potency determination. Journal of pharmacological and toxicological methods 61, 304-310.
Pellett, S., et al. (2016). Purification and Characterization of Botulinum Neurotoxin FA from a Genetically Modified Clostridium botulinum Strain. mSphere 1.
Pellett, S., et al., Assessment of ELISA as endpoint in neuronal cell-based assay for BoNT detection using hiPSC derived neurons. J Pharmacol Toxicol Methods 2017, 88 (Pt 1), 1-6.
Pellett, S., et al., Substrate cleavage and duration of action of botulinum neurotoxin type FA ("H, HA"). Toxicon 2018, 147, 38-46.
Perry, C. M., Meningococcal groups C and Y and haemophilus B tetanus toxoid conjugate vaccine (HibMenCY-TT;MenHibrix((R))): a review. Drugs 2013, 73 (7), 703-13.
Pier, C.L., et al. (2008). Recombinant holotoxoid vaccine against botulism. Infect Immun 76, 437-442.
Przedpelski, A., et al. "Enhancing toxin-based vaccines against botulism." Vaccine 36.6 (2018): 827-832.
Przedpelski, A., et al. (2013). Enhancing the protective immune response against botulism. Infect Immun 81, 2638-2644.
Rai, D., et al. (2009). Tracking the total CD8 T cell response to infection reveals substantial discordance in magnitude and kinetics between inbred and outbred hosts. J Immunol 183, 7672-7681.
Rao, K. N.; et al., Structural analysis of the catalytic domain of tetanus neurotoxin. Toxicon 2005, 45 (7), 929-39.
Rappuoli, R., Glycoconjugate vaccines: Principles and mechanisms. Sci Transl Med 2018, 10 (456).
Rappuoli, R., The vaccine containing recombinant pertussis toxin induces eariy and long-lasting protection. Biologicals 1999, 27 (2), 99-102.
Rappuoli, R.; et al., Progress towards the development of new vaccines against whooping cough. Vaccine 1992, 10 (14), 1027-32.
Ravichandran, E., et al. (2016). In Vivo Toxicity and Immunological Characterization of Detoxified Recombinant Botulinum Neurotoxin Type A. Pharm Res 33, 639-652.
Rummel, A.; et al., Botulinum neurotoxins C, E and F bind gangliosides via a conserved binding site prior to stimulation-

(56) References Cited

OTHER PUBLICATIONS dependent uptake with botulinum neurotoxin F utilising the three isoforms of SV2 as second receptor. J Neurochem 2009, 110 (6), 1942-54.
Schantz, E.J. et al. (1978). Standardized assay for Clostridium botulinum toxins. Journal of the Association of Official Analytical Chemists 61, 96-99.
Schiavo, G., et al. (2000). Neurotoxins affecting neuroexocytosis. Physiological reviews 80, 717-766.
Schmidt, J. J.; et al., Partial amino acid sequence of the heavy and light chains of botulinum neurotoxin type A. Biochem Biophys Res Commun 1984, 119 (3), 900-4.
Schwarz, P. J.; et al., Botulism immune globulin for infant botulism arrives—one year and a Gulf War later. West J Med 1992, 156 (2), 197-8.
Shone, C., et al. (2009). Bivalent recombinant vaccine for botulinum neurotoxin types A and B based on a polypeptide comprising their effector and translocation domains that is protective against the predominant A and B subtypes. Infect Immun 77, 2795-2801.
Sikorra, S.; et al., Substrate recognition mechanism of VAMP/synaptobrevin-cleaving clostridial neurotoxins. J Biol Chem 2008, 283 (30), 21145-52.
Skurnik, D.; et al., The exceptionally broad-based potential of active and passive vaccination targeting the conserved microbial surface polysaccharide PNAG. Expert Rev Vaccines 2016, 15 (8), 1041-53.
Smith, L. A., Botulism and vaccines for its prevention. Vaccine 2009, 27 Suppl 4, D33-9.
Specht, C. A.; et al., Protection against Experimental Cryptococcosis following Vaccination with Glucan Particles Containing Cryptococcus Alkaline Extracts. MBio 2015, 6 (6), e01905-15.
Strotmeier, J.; et al., Identification of the synaptic vesicle glycoprotein 2 receptor binding site in botulinum neurotoxin A. FEBS Lett 2014, 588 (7), 1087-93.
Sundeen, G.; et al., Vaccines against Botulism. Toxins (Basel) 2017, 9 (9).
Tepp, W.H., et al. (2012). Purification and characterization of a novel subtype a3 botulinum neurotoxin. Appl Environ Microbiol 78, 3108-3113.
Torii, Y., et al. (2002). Production and immunogenic efficacy of botulinum tetravalent (A, B, E, F) toxoid. Vaccine 20, 2556-2561.

* cited by examiner

| | IC50 |
|---|---|
| #3 | 0.0147 |
| #7 | 0.03405 |
| #78 | 0.01532 |
| #21 | 0.03851 |
| #24 | 0.07844 |
| #25 | 0.1319 |

FIG. 8

*Clostridium tetani* tetanus toxin (GenBank X06214.1)

MPITINNFRYSDPVNNDTIIMMEPPYCKGLDIYYKAFKITDRIWIVPERYEFGTKPEDFNPPSSLIEGASEYYDPNYLRTDSDKD
RFLQTMVKLFNRIKNNVAGEALLDKIINAIPYLGNSYSLLDKFDTNSNSVSFNLLEQDPSGATTKSAMLTNLIIFGPGPVLNKN
EVRGIVLRVDNKNYFPCRDGFGSIMQMAFCPEYVPTFDNVIENITSLTIGKSKYFQDPALLLMHELIHVLHGLYGMQVSSHEII
PSKQEIYMQHTYPISAEELFTFGGQDANLISIDIKNDLYEKTLNDYKAIANKLSQVTSCNDPNIDIDSYKQIYQQKYQFDKDSN
GQYIVNEDKFQILYNSIMYGFTEIELGKKFNIKTRLSYFSMNHDPVKIPNLLDDTIYNDTEGFNIESKDLKSEYKGQNMRVNT
NAFRNVDGSGLVSKLIGLCKKIIPPTNIRENLYNRTASLTDLGGELCIKIKNEDLTFIAEKNSFSEEPFQDEIVSYNTKNKPLNFN
YSLDKIIVDYNLQSKITLPNDRTTPVTKGIPYAPEYKSNAASTIEIHNIDDNTIYQYLYAQKSPTTLQRITMTNSVDDALINSTKI
YSYFPSVISKVNQGAQGILFLQWVRDIIDDFTNESSQKTTIDKISDVSTIVPYIGPALNIVKQGYEGNFIGALETTGVVLLLEYIP
EITLPVIAALSIAESSTQKEKIIKTIDNFLEKRYEKWIEVYKLVKAKWLGTVNTQFQKRSYQMYRSLEYQVDAIKKIIDYEYKI
YSGPDKEQIADEINNLKNKLEEKANKAMININIFMRESSRSFLVNQMINEAKKQLLEFDTQSKNILMQYIKANSKFIGITELKK
LESKINKVFSTPIPFSYSKNLDCWVDNEEDIDVILKKSTILNLDINNDIISDISGFNSSVITYPDAQLVPGINGKAIHLVNNESSEVI
VHKAMDIEYNDMFNNFTVSFWLRVPKVSASHLEQYGTNEYSIISSMKKHSLSIGSGWSVSLKGNNLIWTLKDSAGEVRQITF
RDLPDKFNAYLANKWVFITITNDRLSSANLYINGVLMGSAEITGLGAIREDNNITLKLDRCNNNNQYVSIDKFRIFCKALNPK
EIEKLYTSYLSITFLRDFWGNPLRYDTEYYLIPVASSSKDVQLKNITDYMYLTNAPSYTNGKLNIYYRRLYNGLKFIIKRYTPN
NEIDSFVKSGDFIKLYVSYNNNEHIVGYPKDGNAFNNLDRILRVGYNAPGIPLYKKMEAVKLRDLKTYSVQLKLYDDKNASL
GLVGTHNGQIGNDPNRDILIASNWYFNHLKDKILGCDWYFVPTDEGWTND

(SEQ ID NO:1)

FIG. 9

**2M-TT (TeNTRY) (GenBank X06214.1. modified for optimized expression in *Escherichia coli* )**

MPITINNFRYSDPVNNDTIIMMEPPYCKGLDIYYKAFKITDRIWIVPERYEFGTKPEDFNPPSSLIEGASEYYDPNYLRTDSDKD
RFLQTMVKLFNRIKNNVAGEALLDKIINAIPYLGNSYSLLDKFDTNSNSVSFNLLEQDPSGATTKSAMLTNLIIFGPGPVLNKN
EVRGIVLRVDNKNYFPCRDGFGSIMQMAFCPEYVPTFDNVIENITSLTIGKSKYFQDPALLLMHELIHVLHGLYGMQVSSHEII
PSKQEIYMQHTYPISAEELFTFGGQDANLISIDIKNDLYEKTLNDYKAIANKLSQVTSCNDPNIDIDSYKQIYQQKYQFDKDSN
GQYIVNEDKFQILYNSIMYGFTEIELGKKFNIKTALSFFSMNHDPVKIPNLLDDTIYNDTEGFNIESKDLKSEYKGQNMRVNTN
AFRNVDGSGLVSKLIGLCKKIIPPTNIRENLYNRTASLTDLGGELCIKIKNEDLTFIAEKNSFSEEPFQDEIVSYNTKNKPLNFNY
SLDKIIVDYNLQSKITLPNDRTTPVTKGIPYAPEYKSNAASTIEIHNIDDNTIYQYLYAQKSPTTLQRITMTNSVDDALINSTKIY
SYFPSVISKVNQGAQGILFLQWVRDIIDDFTNESSQKTTIDKISDVSTIVPYIGPALNIVKQGYEGNFIGALETTGVVLLLEYIPEI
TLPVIAALSIAESSTQKEKIIKTIDNFLEKRYEKWIEVYKLVKAKWLGTVNTQFQKRSYQMYRSLEYQVDAIKKIIDYEYKIYS
GPDKEQIADEINNLKNKLEEKANKAMININIFMRESSRSFLVNQMINEAKKQLLEFDTQSKNILMQYIKANSKFIGITELKKLE
SKINKVFSTPIPFSYSKNLDCWVDNEEDIDVILKKSTILNLDINNDIISDISGFNSSVITYPDAQLVPGINGKAIHLVNNESSEVIV
HKAMDIEYNDMFNNFTVSFWLRVPKVSASHLEQYGTNEYSIISSMKKHSLSIGSGWSVSLKGNNLIWTLKDSAGEVRQITFR
DLPDKFNAYLANKWVFITITNDRLSSANLYINGVLMGSAEITGLGAIREDNNITLKLDRCNNNNQYVSIDKFRIFCKALNPKEI
EKLYTSYLSITFLRDFWGNPLRYDTEYYLIPVASSSKDVQLKNITDYMYLTNAPSYTNGKLNIYYRRLYNGLKFIIKRYTPNN
EIDSFVKSGDFIKLYVSYNNNEHIVGYPKDGNAFNNLDRILRVGYNAPGIPLYKKMEAVKLRDLKTYSVQLKLYDDKNASLG
LVGTHNGQIGNDPNRDILIASNWYFNHLKDKILGCDWYFVPTDEGWTND

(SEQ ID NO:2)

FIG. 10

5M-TeNT

MPITINNFRYSDPVNNDTIIMMEPPYCKGLDIYYKAFKITDRIWIVPERYEFGTKPEDFNPPSSLIEGASEYYDPNYLRTDSDKD
RFLQTMVKLFNRIKNNVAGEALLDKIINAIPYLGNSYSLLDKFDTNSNSVSFNLLEQDPSGATTKSAMLTNLIIFGPGPVLNKN
EVRGIVLRVDNKNYFPCRDGFGSIMQMAFCPEYVPTFDNVIENITSLTIGKSKYFQDPALLLMHQLIHVLHGLYGMQVSSHEI
IPSKQEIYMQHTYPISAEELFTFGGQDANLISIDIKNDLYEKTLNDYKAIANKLSQVTSCNDPNIDIDSYKQIYQQKYQFDKDSN
GQYIVNEDKFQILYNSIMYGFTEIELGKKFNIKTALSFFSMNHDPVKIPNLLDDTIYNDTEGFNIESKDLKSEYKGQNMRVNTN
AFRNVDGSGLVSKLIGLCKKIIPPTNIRENLYNRTASLTDLGGELCIKIKNEDLTFIAEKNSFSEEPFQDEIVSYNTKNKPLNFNY
SLDKIIVDYNLQSKITLPNDRTTPVTKGIPYAPEYKSNAASTIEIHNIDDNTIYQYLYAQKSPTTLQRITMTNSVDDALINSTKIY
SYFPSVISKVNQGAQGILFLQWVRDIIDDFTNESSQKTTIDKISDVSTIVPYIGPALNIVKQGYEGNFIGALETTGVVLLLEYIPEI
TLPVIAALSIAESSTQKEKIIKTIDNFLEKRYEKWIEVYKLVKAKWLGTVNTQFQKRSYQMYRSLEYQVDAIKKIIDYEYKIYS
GPDKEQIADEINNLKNKLEEKANKAMININIFMRESSRSFLVNQMINEAKKQLLEFDTQSKNILMQYIKANSKFIGITELKKLE
SKINKVFSTPIPFSYSKNLDCWVDNEEDIDVILKKSTILNLDINNDIISDISGFNSSVITYPDAQLVPGINGKAIHLVNNESSEVIV
HKAMDIEYNDMFNNFTVSFWLRVPKVSASHLEQYGTNEYSIISSMKKHSLSIGSGWSVSLKGNNLIWTLKDSAGEVRQITFR
DLPDKFNAYLANKWVFITITNDRLSSANLYINGVLMGSAEITGLGAIREDNNITLKLDRCNNNNQYVSIDKFRIFCKALNPKEI
EKLYTSYLSITFLRDFWGNPLRYDTEYYLIPVASSSKDVQLKNITDYMYLTNAPSYTNGKLNIYYRRLYNGLKFIIKRYTPNN
EIDSFVKSGDFIKLYVSYNNNEHIVGYPKDGNAFNNLDRILLVGYNAPGIPLYKKMEAVKLRDLKTYSVQLKLYDDKNASLG
LVGTHNGQIGNDPNRDILIASNAYFNHLKDKILGCDWYFVPTDEGWTND

(SEQ ID NO:4)

FIG. 11

6M-TeNT

MPITINNFRYSDPVNNDTIIMMEPPYCKGLDIYYKAFKITDRIWIVPERYEFGTKPEDFNPPSSLIEGASEYYDPNYLRTDSDKD
RFLQTMVKLFNRIKNNVAGEALLDKIINAIPYLGNSYSLLDKFDTNSNSVSFNLLEQDPSGATTKSAMLTNLIIFGPGPVLNKN
EVRGIVLRVDNKNYFPCRDGFGSIMQMAFCPEYVPTFDNVIENITSLTIGKSKYFQDPALLLMHQLIHVLHGLYGMQVSSHEI
IPSKQEIYMQHTYPISAEELFTFGGQDANLISIDIKNDLYEKTLNDYKAIANKLSQVTSCNDPNIDIDSYKQIYQQKYQFDKDSN
GQYIVNEDKFQILYNSIMYGFTEIELGKKFNIKTALSFFSMNHDPVKIPNLLDDTIYNDTEGFNIESKDLKSEYKGQNMRVNTN
AFRNVDGSGLVSKLIGLCKKIIPPTNIRENLYNRTASLTDLGGELCIKIKNEDLTFIAEKNSFSEEPFQDEIVSYNTKNKPLNFNY
SLDKIIVDYNLQSKITLPNDRTTPVTKGIPYAPEYKSNAASTIEIHNIDDNTIYQYLYAQKSPTTLQRITMTNSVDDALINSTKIY
SYFPSVISKVNQGAQGILFLQWVRDIIDDFTNESSQKTTIDKISDVSTIVPYIGPALNIVKQGYEGNFIGALETTGVVLLLEYIPEI
TLPVIAALSIAESSTQKEKIIKTIDNFLEKRYEKWIEVYKLVKAKWLGTVNTQFQKRSYQMYRSLEYQVDAIKKIIDYEYKIYS
GPDAEQIADEINNLKNKLEEKANKAMININIFMRESSRSFLVNQMINEAKKQLLEFDTQSKNILMQYIKANSKFIGITELKKLE
SKINKVFSTPIPFSYSKNLDCWVDNEEDIDVILKKSTILNLDINNDIISDISGFNSSVITYPDAQLVPGINGKAIHLVNNESSEVIV
HKAMDIEYNDMFNNFTVSFWLRVPKVSASHLEQYGTNEYSIISSMKKHSLSIGSGWSVSLKGNNLIWTLKDSAGEVRQITFR
DLPDKFNAYLANKWVFITITNDRLSSANLYINGVLMGSAEITGLGAIREDNNITLKLDRCNNNNQYVSIDKFRIFCKALNPKEI
EKLYTSYLSITFLRDFWGNPLRYDTEYYLIPVASSSKDVQLKNITDYMYLTNAPSYTNGKLNIYYRRLYNGLKFIIKRYTPNN
EIDSFVKSGDFIKLYVSYNNNEHIVGYPKDGNAFNNLDRILLVGYNAPGIPLYKKMEAVKLRDLKTYSVQLKLYDDKNASLG
LVGTHNGQIGNDPNRDILIASNAYFNHLKDKILGCDWYFVPTDEGWTND

(SEQ ID NO:5)

FIG. 12

7M-TeNT

MPITINNFRYSDPVNNDTIIMMEPPACKGLDIYYKAFKITDRIWIVPERYEFGTKPEDFNPPSSLIEGASEYYDPNYLRTDSDKD
RFLQTMVKLFNRIKNNVAGEALLDKIINAIPYLGNSYSLLDKFDTNSNSVSFNLLEQDPSGATTKSAMLTNLIIFGPGPVLNKN
EVRGIVLRVDNKNYFPCRDGFGSIMQMAFCPEYVPTFDNVIENITSLTIGKSKYFQDPALLLMHQLIHVLHGLYGMQVSSHEI
IPSKQEIYMQHTYPISAEELFTFGGQDANLISIDIKNDLYEKTLNDYKAIANKLSQVTSCNDPNIDIDSYKQIYQQKYQFDKDSN
GQYIVNEDKFQILYNSIMYGFTEIELGKKFNIKTALSFFSMNHDPVKIPNLLDDTIYNDTEGFNIESKDLKSEYKGQNMRVNTN
AFRNVDGSGLVSKLIGLCKKIIPPTNIRENLYNRTASLTDLGGELCIKIKNEDLTFIAEKNSFSEEPFQDEIVSYNTKNKPLNFNY
SLDKIIVDYNLQSKITLPNDRTTPVTKGIPYAPEYKSNAASTIEIHNIDDNTIYQYLYAQKSPTTLQRITMTNSVDDALINSTKIY
SYFPSVISKVNQGAQGILFLQWVRDIIDDFTNESSQKTTIDKISDVSTIVPYIGPALNIVKQGYEGNFIGALETTGVVLLLEYIPEI
TLPVIAALSIAESSTQKEKIIKTIDNFLEKRYEKWIEVYKLVKAKWLGTVNTQFQKRSYQMYRSLEYQVDAIKKIIDYEYKIYS
GPDAEQIADEINNLKNKLEEKANKAMININIFMRESSRSFLVNQMINEAKKQLLEFDTQSKNILMQYIKANSKFIGITELKKLE
SKINKVFSTPIPFSYSKNLDCWVDNEEDIDVILKKSTILNLDINNDIISDISGFNSSVITYPDAQLVPGINGKAIHLVNNESSEVIV
HKAMDIEYNDMFNNFTVSFWLRVPKVSASHLEQYGTNEYSIISSMKKHSLSIGSGWSVSLKGNNLIWTLKDSAGEVRQITFR
DLPDKFNAYLANKWVFITITNDRLSSANLYINGVLMGSAEITGLGAIREDNNITLKLDRCNNNNQYVSIDKFRIFCKALNPKEI
EKLYTSYLSITFLRDFWGNPLRYDTEYYLIPVASSSKDVQLKNITDYMYLTNAPSYTNGKLNIYYRRLYNGLKFIIKRYTPNN
EIDSFVKSGDFIKLYVSYNNNEHIVGYPKDGNAFNNLDRILLVGYNAPGIPLYKKMEAVKLRDLKTYSVQLKLYDDKNASLG
LVGTHNGQIGNDPNRDILIASNAYFNHLKDKILGCDWYFVPTDEGWTND

(SEQ ID NO:6)

FIG. 13

8M-TeNT

MPITINNFRYSDPVNNDTIIMMEPPACKGLDIYYKAFKITDRIWIVPERYEFGTKPEDFNPPSSLIEGASEYYDPNYLRTDSDKD
RFLQTMVKLFNRIKNNVAGEALLDKIINAIPYLGNSYSLLDKFDTNSNSVSFNLLEQDPSGATTKSAMLTNLIIFGPGPVLNKN
EVRGIVLRVDNKNYFPCRDGFGSIMQMAFCPEYVPTFDNVIENITSLTIGKSKYFQDPALLKMHQLIHVLHGLYGMQVSSHEI
IPSKQEIYMQHTYPISAEELFTFGGQDANLISIDIKNDLYEKTLNDYKAIANKLSQVTSCNDPNIDIDSYKQIYQQKYQFDKDSN
GQYIVNEDKFQILYNSIMYGFTEIELGKKFNIKTALSFFSMNHDPVKIPNLLDDTIYNDTEGFNIESKDLKSEYKGQNMRVNTN
AFRNVDGSGLVSKLIGLCKKIIPPTNIRENLYNRTASLTDLGGELCIKIKNEDLTFIAEKNSFSEEPFQDEIVSYNTKNKPLNFNY
SLDKIIVDYNLQSKITLPNDRTTPVTKGIPYAPEYKSNAASTIEIHNIDDNTIYQYLYAQKSPTTLQRITMTNSVDDALINSTKIY
SYFPSVISKVNQGAQGILFLQWVRDIIDDFTNESSQKTTIDKISDVSTIVPYIGPALNIVKQGYEGNFIGALETTGVVLLLEYIPEI
TLPVIAALSIAESSTQKEKIIKTIDNFLEKRYEKWIEVYKLVKAKWLGTVNTQFQKRSYQMYRSLEYQVDAIKKIIDYEYKIYS
GPDAEQIADEINNLKNKLEEKANKAMININIFMRESSRSFLVNQMINEAKKQLLEFDTQSKNILMQYIKANSKFIGITELKKLE
SKINKVFSTPIPFSYSKNLDCWVDNEEDIDVILKKSTILNLDINNDIISDISGFNSSVITYPDAQLVPGINGKAIHLVNNESSEVIV
HKAMDIEYNDMFNNFTVSFWLRVPKVSASHLEQYGTNEYSIISSMKKHSLSIGSGWSVSLKGNNLIWTLKDSAGEVRQITFR
DLPDKFNAYLANKWVFITITNDRLSSANLYINGVLMGSAEITGLGAIREDNNITLKLDRCNNNNQYVSIDKFRIFCKALNPKEI
EKLYTSYLSITFLRDFWGNPLRYDTEYYLIPVASSSKDVQLKNITDYMYLTNAPSYTNGKLNIYYRRLYNGLKFIIKRYTPNN
EIDSFVKSGDFIKLYVSYNNNEHIVGYPKDGNAFNNLDRILLVGYNAPGIPLYKKMEAVKLRDLKTYSVQLKLYDDKNASLG
LVGTHNGQIGNDPNRDILIASNAYFNHLKDKILGCDWYFVPTDEGWTND

(SEQ ID NO:7)

| Neurotoxin | Loop sequence |
|---|---|
| TT | 765-GPDKE-769 |
| BT A1 | 755-EEEKN-759 |
| BT B1 | 743-EKEKS-747 |
| BT G | 748-EEDKM-752 |
| BT F | 745-LDEKN-749 |
| BT E | 745-TDEKS-749 |
| BT C | 752-GSDKE-756 |
| BT D | 748-GSDKE-752 |

MODIFIED CLOSTRIDIAL NEUROTOXINS AS VACCINES AND CONJUGATE VACCINE PLATFORMS

CROSS-REFERENCE TO RELATED APPLICATIONS

This application is a national stage filing under 35 U.S.C. 371 of International Application No. PCT/US2018/066033, filed Dec. 17, 2018, which claims priority to U.S. Provisional Patent Application No. 62/599,444, filed on Dec. 15, 2017, both of which are incorporated by reference in their entirety as if fully set forth herein.

STATEMENT REGARDING FEDERALLY SPONSORED RESEARCH

This invention was made with government support under grant numbers AI030162 awarded by NIH and FD-U-001418 awarded by FDA. The government has certain rights in the invention.

BACKGROUND

*Botulinum* neurotoxins (BoNTs), the most poisonous substances known to man, are protein toxins produced by *Clostridium botulinum* and select strains of *Clostridium butyricum* and *Clostridium baratii* (Hill and Smith, 2013; Johnson and Montecucco, 2008). BoNTs are synthesized as 150 kDa dichain proteins made up of a 100 kDa heavy chain (HC) and a 50 kDa light chain (LC) linked by a disulfide bond. The HC is further divided into an N-terminal domain ($H_N$), which aids in translocation of the LC into the cell cytosol, and a C-terminal domain ($H_C$), which recognizes and bind to cell surface receptors on neuronal cells (Montal, 2010). Once inside the cell, the LC specifically cleaves a portion of a soluble N-ethylmaleimide sensitive-factor attachment protein receptors (SNARE), thereby inactivating neurotransmitter release (Montecucco and Schiavo, 1993, *Trends in biochemical sciences* 18, 324-327; Schiavo et al., 1995). An experimental vaccine has previously been used to protect 'at risk' populations from botulism, however, use of this chemically inactivated BoNT toxoid vaccine was discontinued due to declining potency. Also, conventional tetanus toxin fragment vaccines are not ideal because of problems with low antigenicity and immunopotency. Accordingly, there remains a need in the art for non-catalytic, non-toxic variants of tetanus and *botulinum* toxins for use as adjuvants and as conjugate vaccines.

SUMMARY OF THE DISCLOSURE

Provided herein are recombinant non-catalytic, non-toxic variant forms of tetanus toxin and uses of such variant toxins. The data described here show significantly reduced toxicity relative to native tetanus toxin and relative to previously described tetanus variants. We envision several independent engineered mutations that inactivate the intrinsic toxicity of tetanus toxin and which can be combined to produce a safe and effective vaccine, including but not limited to the elimination of catalytic activity by eliminating substrate affinity or reducing the rate of reaction, eliminating receptor binding, inhibiting translocation potential, or interfering with toxin interdomain cleavage or disulfide bond disruption, among other steps in toxin intoxication. Described herein are experiments in which we engineered toxins having mutations that reduced host receptor binding along with a reduction in catalysis. These data demonstrate the potential for recombinant toxins comprising selected independent mutations that render them non-toxic and suitable for use as vaccines and conjugate vaccine without the need for chemical cross-linking to reduce toxicity.

In a first aspect, provided herein is a modified tetanus toxin polypeptide comprising a sequence having at least 95% identity to SEQ ID NO:1 and having a mutation at each of positions R372 and Y375, and further comprising a mutation at two or more positions selected from E334, K768, R1126, and W1289, where each position is numbered relative to SEQ ID NO:1, the polypeptide having reduced catalytic activity, translocation, and receptor binding compared with the toxicity and receptor binding of SEQ ID NO:1. The amino acid R at position R372 can be replaced with amino acid A, and the amino acid Y at position Y375 can be replaced with amino acid F. The mutations can comprise R372A, Y375F, E334Q, R1226L, and W1289A. The modified polypeptide can further comprise a covalently linked carbohydrate, whereby the polypeptide is a polypeptide-carbohydrate conjugate. The modified polypeptide can be encoded by SEQ ID NO:2.

In some cases, the mutations can comprise R372A, Y375F, E334Q, K768A, R1226L, and W1289A. The modified polypeptide can be encoded by SEQ ID NO:5. In some cases, the modified polypeptide can further comprise a mutation at one or both of positions L231 and Y26, where each position is numbered relative to SEQ ID NO:1. The mutations at one or both of positions L231 and Y26 comprise L231K and Y26A. The modified polypeptide can be encoded by SEQ ID NO:6 or SEQ ID NO:7.

In another aspect, provided herein is a composition comprising a modified polypeptide as described herein and a pharmaceutically acceptable carrier.

In a further aspect, provided herein is a method of reducing the risk of a subject developing tetanus by inducing an immune response through administering to the subject a therapeutically effective amount of a modified polypeptide as described herein. In some cases, the modified polypeptide is used as an adjuvant. In some cases, the modified polypeptide is used as a vaccine.

The foregoing and other aspects and advantages of the invention will appear from the following description. In the description, reference is made to the accompanying drawings which form a part hereof, and in which there are shown, by way of illustration, preferred embodiments of the invention. Such embodiments do not necessarily represent the full scope of the invention, however, and reference is made therefore to the claims and herein for interpreting the scope of the invention.

BRIEF DESCRIPTION OF THE DRAWINGS

FIG. 8 is an amino acid sequence encoding wild-type Clostridium tetani tetanus toxin (SEQ ID NO:1).

FIG. 9 is an amino acid sequence encoding 2M-TT (SEQ ID NO:2).

FIG. 10 is an amino acid sequence encoding 5M-TeNT (SEQ ID NO:4).

FIG. 11 is an amino acid sequence encoding 6M-TeNT (SEQ ID NO:5).

FIG. 12 is an amino acid sequence encoding 7M-TeNT (SEQ ID NO:6).

FIG. 13 is an amino acid sequence encoding 8M-TeNT (SEQ ID NO:7).

DETAILED DESCRIPTION OF THE DISCLOSURE

Figure 1:
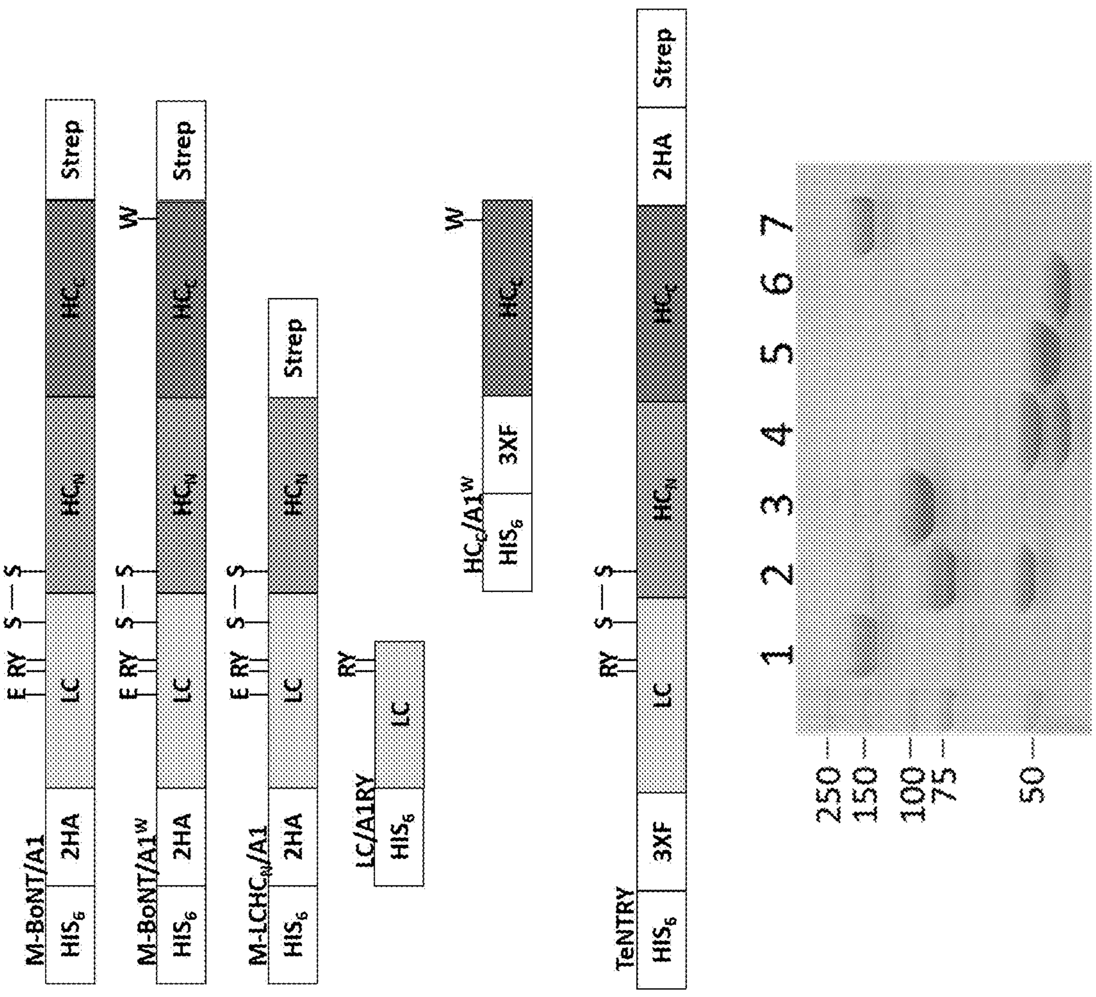
FIG. 1 illustrates recombinant proteins used to assess the host immune response to vaccination. (Upper panel) Schematic of BoNT-derivatives used in this study are shown. Where indicated, two epitopes ($His_6$ and Strep) were used for protein purification. 3XFLAG (3XF) and two sequential hemagglutinin (2HA) epitopes were included for cellular studies. Domain junctions were defined, using the crystal structure of BoNT/A1 (PDB:3BTA). Single amino acid designation above each schematic indicates the introduction of amino acid substitutions introduced to reduce catalysis (LC) or receptor binding ($HC_C$). Note, single chain BoNT and $LCHC_N$ were used for vaccination. (Lower panel) Four μg of the indicated proteins were subjected to SDS-PAGE and Coomassie blue staining. Lanes: 1, M-BoNT/A1; 2, M-BoNT/A1 trypsin nicked and reduced; 3, M-LCHC$_N$/A1; 4. M-LCHC$_N$/A1 trypsin nicked and reduced; 5, LC/A1$^{RY}$; 6, HC$_C$/A1$^W$; and 7, TeNT$^{RY}$. Migration of molecular weight marker proteins (kDa) are shown in left lane. Note in lane 2 nicked HC runs at ~80 kDa, which was shown in other experiments to be due to cleavage of the belt region of HC by trypsin.

The present invention has been described in terms of one or more preferred embodiments, and it should be appreciated that many equivalents, alternatives, variations, and modifications, aside from those expressly stated, are possible and within the scope of the invention.

The methods and compositions described herein are based at least in part on the inventor's development of genetically engineered toxins that are both non-catalytic and incapable of neuronal cell binding. As described in the paragraphs and examples that follow, tetanus toxins and *botulinum* toxins (BoNT) having engineered defects that hinder catalysis and receptor binding provide a platform for vaccine development for toxin-mediated diseases. For example, no toxicity was detected with modified tetanus toxin and BoNT rendered non-catalytic and incapable of receptor binding via engineered mutations. Moreover, such modified toxins were suitable as vaccines to protect against *botulinum* neurotoxin challenge.

Compositions

Preferably, genetically modified toxins of the present disclosure comprise genetic modifications at multiple targets relative to a wild-type toxin, where such modifications eliminate residual toxicity and enhance safety, which will be expanded upon below. Although BoNT and tetanus toxin act on different substrates and receptors, the inventors determined that immune cells take up a non-catalytic, non-receptor binding form of BoNT (referred to herein as "M-BoNT$^{W}$") and mount a similar neutralizing immune response as observed with a non-catalytic BoNT ("M-BoNT"). Based on this observation, additional independent sites of mutation were determined to engineer other non-catalytic, non-receptor toxin variants. When modified as described herein, the resulting engineered non-catalytic, non-receptor binding toxins are suitable for use as vaccine and conjugate vaccine platforms.

Without being bound to any particular theory or mode of action, mutations engineered at independent sites in tetanus toxin and *botulinum* toxin render the toxin proteins unable to express toxicity via independent mechanisms, thus providing a fail-safe against inadvertent genetic reversion to toxicity. Such properties are advantageous for use of variant toxins as vaccines against tetanus and botulism and as conjugate vaccine platforms.

Accordingly, provided herein are recombinantly inactivated bacterial toxins that are irreversibly non-toxic, more potent, and easier to produce and manipulate than current chemically inactivated toxoid and, thus, provide improved vaccines and conjugate vaccine carriers. In a first aspect, provided herein are isolated preparations of recombinant non-catalytic, non-toxic modified forms of bacterial protein toxins (e.g., tetanus toxin and *botulinum* neurotoxin), where the modified toxins are full length toxins comprising at least four amino acid substitutions that render the proteins incapable of expressing toxicity by independent mechanisms. By "preparation" we mean any concentration of the toxin polypeptide that is enhanced or purified relative to its natural occurrence. Preferably, the preparation is substantially pure or is combined with other ingredients into a pharmaceutical preparation. In some cases, a preparation of the present invention may include one or more adjuvants or carriers that might be coupled to the toxin polypeptide sequence help to stimulate the immune system. In other cases, the preparation itself has adjuvant activity and is effective to boost an immune response to a conjugated antigen or co-administered antigen.

As used herein, "toxin" refers to a noxious or poisonous substance (e.g., a cytotoxin) that is formed or elaborated either as an integral part of a cell or tissue (endotoxin), as an intracellular or extracellular product (exotoxin), or as a combination thereof, during the metabolism and growth of certain microorganisms. As used herein, the term "modified toxin" refers to a non-catalytic, non-toxic variant form of a toxin, wherein the toxin is rendered non-catalytic and non-toxic by genetically engineered (e.g., non-naturally occurring, man-made) modifications to the amino acid sequence of the polypeptide toxin. In exemplary embodiments, modified toxins are genetically engineered or otherwise modified variants of a toxin produced by a bacterium of the genus *Clostridium* (e.g., *C. difficile, C. novyi, C. sordellii, C. perfringens, C. tetani*, and *C. botulinum*). The toxins may be recombinant, synthetic, part of a fusion protein (which includes, e.g., an antigen, or a polypeptide (e.g., $His_6$) which facilitates purification of the fusion protein), covalently conjugated to an antigen, and/or chemically cross-linked to an antigen. In some cases, non-catalytic, non-toxic forms of toxins are referred to as toxoids. Toxioids lack toxicity but retain their antigenicity and their immunizing capacity.

As used herein, the term "reduced toxicity" means that, relative to a first composition comprising a particular protein active ingredient (e.g., wild-type TT), a second composition comprising a modified version of a particular protein active ingredient can be administered to a mammal at a dose level which is the same or greater than what is a fatal for the first composition but without death resulting to the mammal. Reduced toxicity encompasses partially or completely eliminated toxicity as detectable by methods known to those who practice in the art. In addition, reduced toxicity encompasses reduced systemic toxicity (i.e., upon intravenous administration) or reduced toxicity upon intramuscular administration.

In certain embodiments, the preparation comprises a modified tetanus toxin. Typically, a tetanus toxin modified as described herein exhibits one or more altered properties as compared to the wild-type tetanus toxin polypeptide shown in SEQ ID NO:1, for example, significantly decreased catalytic activity and receptor binding activity. In some embodiments, the modified tetanus toxins described herein are at least 1,000,000 times less toxic than wild-type tetanus toxin.

TABLE 1

Exemplary toxins M-BoNT/A1$^{W}$ and 5M-TeNT comprising multiple functionally independent mutations as a vaccine and conjugate vaccine

| Residues mutated (function inhibited) | M-BoNT/A1$^{W}$ | 5M-TeNT |
|---|---|---|
| E (catalysis) | E224A | E334Q |
| R (catalysis) | R363A | R372A |
| Y (catalysis) | Y366F | Y375F |
| R (receptor binding) | Wild-type | R1226L |
| W (receptor binding) | W1266A | W1289A |

In certain embodiments, the preparation comprises a modified tetanus toxin having mutations at amino acid residues 372 and 375, and further having a mutation at one or more of residues 334, 1226, and 1289, where the residue positions are numbered relative to the full-length wild-type tetanus neurotoxin (*Clostridium tetani* CN3911; GenBank accession no. X06214) set forth as SEQ ID NO:1. In certain embodiments, the amino acid mutations at residues 372 and 375 are R372A and Y375F, and the modified toxin further comprises at least one mutation selected from E334Q, R1226L, and W1289A. In some cases, the modified toxin comprises five mutations (R372A, Y375F, E334Q, R1226L, and W1289A) numbered relative to SEQ ID NO:1 and is referred to herein as “5M-TeNT” or “5M-TT.” See Table 1. In some cases, 5M-TeNT is encoded by the amino acid sequence set forth as SEQ ID NO:4.

In some embodiments, the tetanus toxin has a modified translocation domain. For example, the lysine (K) residue at position 768 is located within a loop that connects two long alpha helices. Mutation of this single amino acid to an alanine (A) inactivates or blocks light chain translocation. In some cases, the K768A mutation is added to 5M-TT modified toxin to produce 6M-TT, whereby the resulting modified tetanus toxins comprises independent mutations at six positions (see Tables 2 and 3). In some cases, the modified toxin comprises six mutations (R372A, Y375F, E334Q, K768A, R1226L, and W1289A) numbered relative to SEQ ID NO:1 and is referred to herein as “6M-TeNT” or “6M-TT.” In some cases, 6M-TeNT is encoded by the amino acid sequence set forth as SEQ ID NO:5. Without being bound by any particular mechanism or theory, vaccine potency of 6M-TT is expected to be higher than 5M-TT but should have a lower rate of reversion than 5M-TT. The addition of a mutation at one or more of D767, K768, or E769A to 5M-TT will yield more complete inactivation of the genetically engineered vaccine by inactivating a function of the translocation domain in addition to disrupted functionality of the catalytic and receptor binding domains.

TABLE 2

Exemplary toxins 6M-TeNT comprising multiple functionally independent mutations as a vaccine and conjugate vaccine

| Residues mutated (function inhibited) | M-BoNT/A1[W] | 6M-TeNT (“6M-TT”) |
|---|---|---|
| E (catalysis) | E224A | E334Q |
| R (catalysis) | R363A | R372A |
| Y (catalysis) | Y366F | Y375F |
| R (receptor binding) | Wild-type | R1226L |
| W (receptor binding) | W1266A | W1289A |
| K (light chain translocation) | Wild-type | K768A (or D767A or E769A) |

In some embodiments, the tetanus toxin has been modified to inhibit VAMP-2 cleavage. For example, mutation of the leucine residue at position 231 (for example, mutation of the leucine to a lysine (K)) inactivates the toxin’s catalytic activity for VAMP-2 cleavage. In some cases, the L231K mutation is added to 6M-TT modified toxin to produce 7M-TT, whereby the resulting modified tetanus toxins comprises independent mutations at seven positions (Table 3). In some cases, the modified toxin comprises eight independent mutations (R372A, Y375F, E334Q, R1226L, W1289A, K768A, and L231K) numbered relative to SEQ ID NO:1 and is referred to herein as “7M-TeNT” or “7M-TT.” In some cases, 7M-TeNT is encoded by the amino acid sequence set forth as SEQ ID NO:6.

In some embodiments, the tetanus toxin has been modified to inhibit VAMP-2 binding. For example, mutation of the tyrosine (Y) residue at position 26 (for example, mutation of the tyrosine to an alanine (A)) inactivates VAMP-2 binding capacity of the toxin. In some cases, the Y26A mutation is added to 7M-TT modified toxin to produce 8M-TT, whereby the resulting modified tetanus toxins comprises independent mutations at eight positions (Table 3). In some cases, the modified toxin comprises eight independent mutations (R372A, Y375F, E334Q, R1226L, W1289A, K768A, L231K, and Y26A) numbered relative to SEQ ID NO:1 and is referred to herein as “8M-TeNT” or “8M-TT.” In some cases, 8M-TeNT is encoded by the amino acid sequence set forth as SEQ ID NO:7.

TABLE 3

Exemplary mutations for inactivating multiple independent TT functions

| | Zn++ binding | Substrate Binding & catalysis | Light Chain translocation | Ganglioside receptor binding |
|---|---|---|---|---|
| | E234Q, R372A, Y375F (TT(R372A, Y375F, 2M-TT) is 125,000-fold less toxic than native TT [42] | Y26A, L231K | K768A Inhibits LC translocation (preliminary data) | R1226L, W1289A This mutation is ~800-fold less toxic than TT WT |
| 2MTT | R372A, Y375F | | | |
| 5M-TT | E234Q, R372A, Y375F | | | R1226L, W1289A |
| 6M-TT | E234Q, R372A, Y375F | | K768A (or D767A or E769A) | R1226L, W1289A |
| 7M-TT | E234Q, R372A, Y375F | L231K | K768A (or D767A or E769A) | R1226L, W1289A |
| 8M-TT | E234Q, R372A, Y375F | Y26A, L231K | K768A (or D767A or E769A) | R1226L, W1289A |

In some cases, the modified tetanus toxin comprises other amino acid substitutions at residue positions 372, 275, 334, 768, 1226, 1289, 231, and/or 26. For example, amino acids that may substitute for the listed amino acids include substitutions that reverse the charge or hydrophobicity reversal of the original residue, conservative amino acid substitutions, and substitutions that delete the original residue.

As is well known to those skilled in the art, altering the primary structure of a polypeptide by a conservative amino acid substitution may not significantly alter the activity of that polypeptide because the side-chain of the amino acid which is inserted into the sequence may be able to form similar bonds and contacts as the side chain of the amino acid which has been substituted out. This is so even when the substitution is in a region which is critical in determining the polypeptide’s conformation.

Conservative amino acid substitutions are art recognized substitutions of one amino acid for another amino acid having similar characteristics. Conservative amino acid substitutions may be achieved by modifying a nucleotide sequence to introduce a nucleotide change that will encode the conservative substitution. For example, each amino acid may be described as having one or more of the following characteristics: electropositive, electronegative, aliphatic, aromatic, polar, hydrophobic and hydrophilic. Conservative substitutions include substitution among amino acids within each group. Acidic amino acids include aspartate, glutamate. Basic amino acids include histidine, lysine, arginine; aliphatic amino acids include isoleucine, leucine and valine. Aromatic amino acids include phenylalanine, glycine, tyrosine and tryptophan. Polar amino acids include aspartate, glutamate, histidine, lysine, asparagine, glutamine, arginine, serine, threonine and tyrosine. Hydrophobic amino acids include alanine, cysteine, phenylalanine, glycine, isoleucine, leucine, methionine, proline, valine and tryptophan. Amino acids may also be described in terms of relative size, where alanine, cysteine, aspartate, glycine, asparagine, proline, threonine, serine, valine, are considered to be small.

In some cases, non-conservative substitutions are possibly provided if these substitutions do not disrupt the tertiary structure of an epitope within the polypeptide, for example, which do not interrupt the immunogenicity (for example, the antigenicity) of the polypeptide and do not restore toxicity.

In certain embodiments, the modified tetanus toxin comprises mutations at amino acid residues 372 and 375, and further comprises a mutation at one or more of residues 334, 1226, and 1289, where the modified toxin is conjugated or coupled to another peptide, as described below, for appropriate therapeutic methods. Advantageously, modified tetanus toxins of this disclosure do not require detoxification with formalin for use as a vaccine or adjuvant. In some cases, small quantities of formalin (~0.04%) or another fixative or stabilizing reagent (e.g., formalin, glutaraldehyde, β-propiolactone and the like) are added to the modified tetanus toxin as a stabilizing agent, but such quantities are smaller (e.g., smaller by an order of magnitude) than those generally used (~0.4%) to detoxify wild-type tetanus toxin (or tetanus toxin not modified as described herein) to form "tetanus toxoid."

In certain embodiments, modified toxins described herein further comprise molecules such as carbohydrates, protein or peptide (e.g., antigens), and chemical moieties. In particular, provided herein are recombinant non-catalytic, non-toxic variant toxin forms (e.g., modified tetanus toxin and modified *botulinum* neurotoxin) further modified to comprise a conjugated or chemically linked (e.g., cross-linked) carbohydrate. In this manner, the modified toxins conjugated to carbohydrates provide a platform for use as T-cell dependent immunogens. In some cases, other molecules or moieties (e.g., antigens) can be further linked to the cross-linked moiety as "cargo."

In some cases, a modified, carbohydrate-conjugated tetanus toxin comprises five mutations (R372A, Y375F, E334Q, R1226L, and W1289A) numbered relative to SEQ ID NO:1 and is referred to herein as "TeNT(CB)." In other cases, a modified, carbohydrate-conjugated BoNT toxin comprises four mutations (E224A, R363A, Y366F, and W1266A) numbered relative to UniProtKB/Swiss-Prot: P10845.4 and is referred to herein as "BoNT(CB)." In some cases, carbohydrates are conjugated to the modified toxin by chemical cross-linking. Common chemical reactions for covalently linking polysaccharides to polypeptides such as toxin include, without limitation, reductive amination, cyanalation conjugation, and carbodiimide reactions. In other cases, carbohydrate-toxin conjugates are prepared by other synthetic schemes such as the scheme described by Chu et al., 1983. *Infect and Immun.* 40(1):245-256.

The term "carbohydrate" as used herein is intended to include polysaccharides, oligosaccharides and other carbohydrate polymers, including monomeric sugars. Typically, polysaccharides have from about 10 to up to 2,000 or more repeating units, and preferably from about 100 to 1900 repeating unit. Oligosaccharides typically about from about 2 to 10 repeating units to about 15, 20, 25, 30, or 35 to about 40 or 45 repeating units. In some cases, carbohydrates suitable for conjugation to modified toxins provided herein include, without limitation, polysaccharides that have carboxyl groups. In such cases, the polysaccharide having carboxyl groups can be conjugated through a thiol derivative of said carboxyl groups to the modified toxin.

The terms "polypeptide," "peptide," and "protein," as used herein, refer to a polymer comprising amino acid residues predominantly bound together by covalent amide bonds. By the term "protein," we mean to encompass all the above definitions. The terms apply to amino acid polymers in which one or more amino acid residue may be an artificial chemical mimetic of a naturally occurring amino acid, as well as to naturally occurring amino acid polymers and non-naturally occurring amino acid polymers. As used herein, the terms may encompass amino acid chains of any length, including full length proteins, wherein the amino acids are linked by covalent peptide bonds. The protein or peptide may be isolated from a native organism, produced by recombinant techniques, or produced by synthetic production techniques known to one skilled in the art.

In some cases, spacer moieties are employed as spacer arm bridges between the modified toxin and linked molecule. The spacer moiety can be any of a wide variety of molecular structures including, without limitation, dextran, polyglutamic acid, and oligopeptides.

Sequence identity between amino acid sequences can be determined by comparing an alignment of the sequences. When an equivalent position in the compared sequences is occupied by the same amino acid, then the molecules are identical at that position. Scoring an alignment as a percentage of identity is a function of the number of identical amino acids at positions shared by the compared sequences. When comparing sequences, optimal alignments may require gaps to be introduced into one or more of the sequences, to take into consideration possible insertions and deletions in the sequences. Sequence comparison methods may employ gap penalties so that, for the same number of identical molecules in sequences being compared, a sequence alignment with as few gaps as possible, reflecting higher relatedness between the two compared sequences, will achieve a higher score than one with many gaps. Calculation of maximum percent identity involves the production of an optimal alignment, taking into consideration gap penalties. As mentioned above, the percentage sequence identity may be determined using the Needleman-Wunsch Global Sequence Alignment tool, publicly available at blast.ncbi.nlm.nih.gov/Blast.cgi, using default parameter settings. The Needleman-Wunsch algorithm was published in *J. Mol. Biol.* (1970) vol. 48:443-53.

Polypeptides and nucleic acids of the invention may be prepared synthetically using conventional synthesizers. Alternatively, they may be produced using recombinant DNA technology and may be incorporated into suitable expression vector, which is then used to transform a suitable host cell, such as a prokaryotic cell such as *E. coli*. The transformed host cells are cultured and the polypeptide isolated therefrom.

In another embodiment, the present invention is a nucleic acid sequence which codes for the modified toxin preparations and other nucleic acid sequence which hybridize to a nucleic molecule consisting of the above-described nucleotide sequences under high stringency conditions. In a particular-embodiment provided herein are DNA sequences encoding the modified tetanus toxin having mutations at amino acid residues 372 and 375, and further comprises a mutation at one or more of residues 334, 1226, and 1289 or the modified catalytic domain described herein. In some cases, the nucleic acid sequence encoding a modified tetanus toxin is set forth as SEQ ID NO:3.

The term "stringent conditions" as used herein refers to parameters with which the art is familiar. For example, nucleic acid hybridization parameters may be found in references which compile such methods, e.g., *Molecular Cloning: A Laboratory Manual*, J. Sambrook, et al., eds., Second Edition, Cold Spring Harbor Laboratory Press, Cold Spring Harbor, New York, 1989, or *Current Protocols in Molecular Biology*, F. M. Ausubel, et al., eds., John Wiley & Sons, Inc., New York. More specifically, high stringency conditions as used herein, refers to hybridization at 65° C. in hybridization buffer (3.5×SSC, 0.02% Ficoll, 0.02% Polyvinyl pyrolidone, 0.02% Bovine Serum Albumin, 25 mM $NaH_2PO_4$ (pH 7), 0.5% SDS, 2 mM EDTA). SSC is 0.15M Sodium Chloride/0.015M Sodium Citrate, pH 7; SDS is Sodium Dodecyl Sulphate; and EDTA is Ethylene diaminetetraacetic acid. After hybridization, the membrane upon which the DNA is transferred is washed at 2×SSC at room temperature and then at 0.1-0.5×SSC/0.1×SDS at temperatures up to 68° C., e.g., 55° C., 60° C., 65° C. or 68° C. Alternatively, high stringency hybridization may be performed using a commercially available hybridization buffer, such as ExpressHyb™ buffer (Clontech) using hybridization and washing conditions described by the manufacturer.

It will also be understood that the invention embraces the use of the sequences in expression vectors, as well as to transfect host cells and cell lines, be these prokaryotic (e.g. *E. coli*), or eukaryotic (e.g., dendritic cells, CHO cells, COS cells, yeast expression systems, recombinant baculovirus expression in insect cells). The expression vectors require that the pertinent sequence, i.e., those described supra, be operably linked to a promoter.

In another aspect, provided herein is an immunogenic composition comprising a modified toxin as described herein which, upon introduction into a host, will confer immunity to that host, in the event the host is subsequently challenged by the same microorganism (e.g., tetanus bacillus), which produced the protein(s). In preferred embodiments, the immunogenic composition is a vaccine comprising a modified toxin as described herein and further comprising an excipient and/or diluent appropriate where composition is to be administered to a subject in need of vaccination against developing disease caused by tetanus bacilli (*Clostridium tetani*) or *Clostridium botulinum*, or their purified toxins.

The term "vaccine," as used herein, refers to a composition that includes an antigen. Vaccine may also include a biological preparation that improves immunity to a particular disease. A vaccine may typically contain an agent, referred to as an antigen, that resembles a disease-causing microorganism, and the agent may often be made from weakened or killed forms of the microbe, its toxins or one of its surface proteins. The antigen may stimulate the body's immune system to recognize the agent as foreign, destroy it, and "remember" it, so that the immune system can more easily recognize and destroy any of these microorganisms that it later encounters. Similarly, the modified toxin preparations, combined with vaccines against other pathogens, could "boost" the immune responses to the pathogen of interest, by acting themselves as vaccine adjuvants. Adjuvants can be classified according to their physiochemical properties or mechanisms of action. The two major classes of adjuvants include compounds that directly act on the immune system such as bacterial toxins that stimulate immune responses, and molecules able to facilitate the presentation of antigens in a controlled manner and behaving as a carrier.

Selection of appropriate vaccine components is within the routine capability of the skilled person. For example, the vaccine composition of the invention may conveniently be formulated using a pharmaceutically acceptable excipient or diluent, such as, for example, an aqueous solvent, non-aqueous solvent, non-toxic-excipient, such as a salt, preservative, buffer and the like. Examples of non-aqueous solvents are propylene glycol, polyethylene glycol, vegetable oil and injectable organic esters such as ethyloleate. Aqueous solvents include water, alcoholic/aqueous solutions, saline solutions, parenteral vehicles such as sodium chloride, Ringer's dextrose, etc. Preservatives include antimicrobial, anti-oxidants, chelating agents and inert gases. The pH and exact concentration of the various components the vaccine composition are adjusted according to routine skills.

In some cases, the preparation described herein may include purified modified toxins, including preparation comprising partial toxin complexes. In some embodiments, the preparations may further include stabilizers that are known to stabilize the modified BoNT and tetanus toxin proteins. Suitable stabilizers are known in the art, and include, but are not limited to, for example, human or bovine serum albumin, gelatin, recombinant albumin as described in US Publication US2005/0238663 (the contents of which are incorporated by reference in its entirety) among others.

The terms "subject" and "patient" are used interchangeably and refer to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

A preparation of the present invention can be administered in a therapeutically effective amount. The terms "effective amount" or "therapeutically effective amount" refer to an amount of an antigen or vaccine that would induce an immune response in a subject receiving the antigen or vaccine which is adequate to prevent signs or symptoms of disease, including adverse health effects or complications thereof, caused by infection with a pathogen, such as a virus or a bacterium. Humoral immunity or cell mediated immunity or both humoral and cell mediated immunity may be induced. The immunogenic response of an animal to a vaccine may be evaluated, e.g., indirectly through measurement of antibody titers, lymphocyte proliferation assays, or directly through monitoring signs and symptoms after challenge with wild-type strain. The protective immunity conferred by a vaccine may be evaluated by measuring, e.g., reduction in clinical signs such as mortality, morbidity, temperature number, overall physical condition, and overall health and performance of the subject. The amount of a vaccine that is therapeutically effective may vary depending on the particular preparation used, or the condition of the subject, and may be determined by a physician.

A preparation of the present invention can be administered in a therapeutically effective amount depending on the type of treatment necessary. Methods of determining suitable dosage or dosage ranges for individual treatment are known to those in the art. For methods provided herein, a preparation of the present invention can be administered by any means that achieves the intended purpose or is deemed appropriate by those skilled in the art. In an exemplary embodiment, a modified toxin preparation is administered either as a single dose or, when appropriate, as continuous administration using, for instance, a mini pump system. In some cases, a modified toxin preparation is provided as a liquid dosages form or as a lyophilized dosages form that is, for example, reconstituted prior to administration.

The term "protected," as used herein, refers to immunization of a patient against a disease or condition. The immunization may be caused by administering a vaccine comprising an antigen. Specifically, in the present invention, the immunized patient is protected from tetanus disease or symptoms thereof.

In one embodiment, a suitable dosage is from about 1 μg to 20 μg.

Suitable routes of administration for the preparations of modified toxin described herein include, but are not limited to, direct injection. In certain embodiments, each dose is administered intramuscularly.

Dosage, toxicity, and therapeutic efficacy of the agents of the present technology can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

As used herein, a "therapeutically effective amount" refers to an amount of a compound that, when administered to a subject for treating a disease, is sufficient to affect such treatment for the disease. The "therapeutically effective amount" will vary depending on the compound, the disease state being treated, the severity or the disease treated, the age and relative health of the subject, the route and form of administration, the judgment of the attending medical or veterinary practitioner, and other factors. For purposes of the present invention, "treating" or "treatment" describes the management and care of a patient to combat the disease, condition, or disorder. The terms embrace both preventative, i.e., prophylactic, and palliative treatment.

The conjugated delivery platform described herein can be adjusted to target specific conditions or diseases by adjusting which conjugated modified Tet toxin platform is used.

Methods

In another aspect, provided herein are methods for engineering vaccines and conjugate vaccines having reduced toxicity and increased potency. The methods comprise genetically modifying particular amino acid residues within domains of a multi-domain protein toxin whereby the toxin is rendered incapable of expressing toxicity by either catalytic activity or receptor binding activity on target cells (e.g., neurons), is deficient in translocation, and has reduced potential for reversion to a toxic form. Through modification of multiple, independent protein functions, the methods provided herein advantageously provide full length toxins that are ideal candidates for potent vaccines and conjugate vaccines, having virtually no potential for reversion of the protein to toxicity. As used herein, the term "potency" refers to the specific ability or capacity of a vaccine, as indicated by appropriate laboratory tests or by adequately controlled clinical data, to effect protective immunity. In other words, potency is a measure of a vaccine's strength.

In some cases, the method of obtaining an engineered bacterial protein toxoid having increased potency as a vaccine comprises or consists essentially of the following steps: selecting one or more amino acid positions in each domain of an amino acid sequence encoding a multi-domain bacterial protein toxin, where each position is selected to inactivate a protein function associated with each domain, where the domains comprise two or more of a catalytic domain, a translocation domain, a receptor binding domain, and a substrate binding domain; substituting a native amino acid residue at each selected position with a non-native amino acid residue, whereby the substitution inactivates one or more protein functions associated with the domain; and expressing in a host cell a nucleic acid sequence encoding a full-length bacterial protein toxin comprising the substituted non-native amino acid residues, whereby the expressed protein exhibits partial or complete loss of catalytic activity, receptor binding activity, translocation activity, or substrate binding activity relative to the full-length bacterial protein toxin comprising the native amino acids.

Selecting amino acid residues for modification including analyzing protein sequence (e.g., primary amino acid sequence) or structural information to identify individual functional amino acid residues of each domain of the bacterial protein toxin. Preferably, selected residues are those one or more individual amino acid residues of each functional domain (e.g., catalytic domain, translocation domain, receptor binding domain, substrate binding domain) that can be modified without destabilizing the full-length protein and without loss of immunogenicity. Protein stability can be assessed by any appropriate method. In some cases, modified toxins are tested for stability by measuring trypsin sensitivity,[3] and modified toxins are tested for immunogenicity by measuring the immune response to modified toxin vaccination in a mouse mode[4].

Protein structure information can be obtained by any appropriate method such as, for example, x-ray crystallography, electron microscopy, nuclear magnetic resonance spectroscopy, computational protein structure modeling, or a combination thereof. In some cases, the crystal structure of a bacterial protein toxin of interest can be used to identify, for example, specific sites of interaction between functional domains of the toxin and functionally conserved residues between related protein toxins. For example, using diphtheria toxin as an example, amino acid residues involved in catalysis, substrate binding, translocation, and receptor binding are identified in the literature from prior studies and engineered into the gene encoding diphtheria toxin to produce a mutated diphtheria toxin gene that encodes multiple, independent mutations in each of the four functional domains of the toxin based upon alignment of the amino acid sequence within the crystal structure of diphtheria toxin. Nucleic acid sequences encoding the mutated diphtheria toxin will be transformed into *Escherichia coli* and the protein produced recombinantly and tested for loss of toxicity, maintenance of stability, and retained immunogenicity.

By way of example, inter- and intra-domain molecular interactions can be determined from analysis of a wild-type bacterial protein toxin's crystal structure. Substitution mutations can be achieved using well-known methods, such as site-directed mutagenesis, PCR-mediated mutagenesis, and total gene synthesis, as well as other methods known in the art. Illustrative methods of mutagenesis protocols are shown, for example, in the following Examples. In some cases, site-directed mutagenesis is used to generate mutations at single amino acid residues. In some cases, a software program such as PrimerX (available at bioinformatics.org/primerx/ on the World Wide Web) can be used to design oligonucleotide primers for site specific mutagenesis. The wild type bacterial protein toxin gene can be cloned into an expression vector to serve as a template for mutagenesis by any appropriate method such as, for example, polymerase chain reaction. Mutagenesis can be confirmed by nucleic acid sequencing. In some cases, a polynucleotide encoding a modified protein toxin is located in an expression vector. In some cases, the vector is in a host cell (e.g., a bacterial cell, a yeast cell, eukaryotic cell). Numerous expression vectors and systems are known, both for prokaryotes and eukaryotes, and the selection of an appropriate system is a matter of choice. Expression and purification of a modified protein product of the invention can be easily performed by one skilled in the art. See, Sambrook et al., "Molecular cloning-A Laboratory Manual, second edition."

The methods are applicable to virtually any bacterial protein toxin, also known as exotoxins, which are multi-domain proteins that are secreted by bacteria and, in many cases, resemble enzymes in that they act catalytically and exhibit substrate specificity. Bacterial protein toxins include, without limitation, *botulinum* toxin, tetanus toxin, shiga toxin, diphtheria toxin, *Bordetella pertussis* toxin, *E. coli* heat-labile toxin LT, *Bacillus anthraces* toxin, *Pseudomonas* exotoxin A, anthrax toxin Lethal Factor (LF), cholera enterotoxin, and *Staphylococcus aureus* exfoliatin B. Table 4 sets forth exemplary bacterial protein toxins for which crystal structure information is available for use in designing genetically engineered recombinant, non-toxic, high potency toxoids that are particularly advantageous for vaccines and conjugate vaccines.

TABLE 4

Bacterial protein toxins that have multiple, independent functional domains and solved structure

| Bacterial Toxin | AB organization | AB organization and Protein Data Bank reference of the crystal structure of the bacterial toxin (AB)PDB# |
|---|---|---|
| Anthrax toxin | A2-B | (A1)1K93 (A2)1J7N (B)1ACC |
| Cholera toxin | AB5 | (AB5)1XTC |
| Botulinum toxin | AB | (AB)3BTA |
| *Clostridium difficile* toxin A | AB | (AB)4R04 |
| *Clostridium difficile* toxin B | AB | (A)3SS1 (B)6C0B |
| Diphtheria toxin | AB | (AB)1SGK |
| Tetanus toxin | AB | (AB)5N0C |
| *E. coli* heat-labile enterotoxin | AB5 | (AB5)1LTT |
| Pertussis toxin | AB5 | (AB5) 1PRT |
| *P. aeruginosa* exotoxin A | AB | (AB)1IKQ |
| *P. aeruginosa* ExoS | Type III effector | (A)1HE9 |
| *P. aeruginosa* ExoU | Type III effector | (A) 4AKX |
| Shiga toxin | AB5 | (AB5)1DMO |
| Typhoid toxin | A2B5 | (A2B5)4K6L |
| Yersinia pestis (plague) YopE | Type III effector | (A)1JYA |

In some cases, independent, inactivating modifications are selected to disrupt one or more of a bacterial protein toxin's catalytic domain, substrate binding domain, translocation domain, and receptor-binding domain. For example, diphtheria toxin is a bacterial protein toxin comprising having a length of 535 amino acids. Inactivating amino acid residues involved with catalysis (E149S), substrate binding (H21A), translocation (E349K, E362K), and receptor binding (K516A, K526A, H391A) functions will yield a non-toxic, yet potent diphtheria vaccine.

It will be understood, however, that the methods can be applied to virtually any protein having multiple functional domains (e.g., effector domains) for which amino acid sequence and/or crystal structure information is available and for which inactivation modifications can be determined based on known structure-function properties.

In certain embodiments, genetic modifications to hinder host receptor activity are introduced into the C-terminal portion of the Heavy chain ($HC_C$). To hinder catalytic activity, genetic modifications are introduced into the light chain at amino acid residues required or important for neurotransmitter release via the SNARE complex.

The techniques and procedures described or referenced herein are generally well understood and commonly employed using conventional methodology by those skilled in the art, such as, for example, the widely utilized molecular cloning methodologies described in Ausubel et al., Current Protocols in Molecular Biology, Wiley Interscience Publishers, (1995). As appropriate, procedures involving the use of commercially available kits and reagents are generally carried out in accordance with manufacturer defined protocols and/or parameters unless otherwise noted.

Kits.

In another aspect, provided herein is a kit for administering to a subject a vaccine or adjuvant comprising a modified toxin vaccine as described herein. In one embodiment, the kit comprises a form of a modified toxin (e.g., a modified tetanus toxin as described herein). The kit may further comprise instructions enabling a user to carry out a method of vaccinating a subject against developing a disease caused by *Clostridium tetani*, particularly a disease caused by tetanus toxin. In one embodiment, the modified toxin of the present invention is formulated, delivered and stored for use in physiologic conditions. Suitable pharmaceutical carriers include, but are not limited to, for example, saline solution (e.g., 0.9% sodium chloride), phosphate buffer saline, lactated ringer's solution, and the like.

By "instructions for use" we mean a publication, a recording, a diagram, or any other medium of expression which is used to communicate the usefulness of the invention for one of the purposes set forth herein. The instructional material of the kit can, for example, be affixed to a container which contains the present invention or be shipped together with a container which contains the invention. Alternatively, the instructional material can be shipped separately from the container or provided on an electronically accessible form on an internet website with the intention that the instructional material and the biocompatible hydrogel be used cooperatively by the recipient.

In the specification and in the claims, the terms "including" and "comprising" are open-ended terms and should be interpreted to mean "including, but not limited to . . . . " These terms encompass the more restrictive terms "consisting essentially of" and "consisting of."

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The invention will be more fully understood upon consideration of the following non-limiting examples.

EXAMPLES

Example 1

Isolation and Characterization of M-BoNT/A1 and M-BoNT/A1$^W$

This Example describes full length BoNT-engineered with defects in catalysis and receptor binding protected against challenge by $10^6$ $LD_{50}$ of native BoNT/A1. These data indicate the potential for genetically engineered toxins as a platform strategy with multiple mutations that reduce toxicity by independent mechanisms for development of vaccines against botulism and other toxin-mediated diseases.

Materials and Methods:

Biosafety and Biosecurity: Experiments conducted at the University of Wisconsin-Madison were approved by the Institutional Biosafety Committee. In addition, experiments were conducted in laboratories approved for this research by the Federal Select Agent Program by researchers who have undergone suitability assessments and adhere to institutional policies and practices. Animal experiments were approved and conducted according to the guidelines of the Animal Care and Use Committee at the University of Wisconsin-Madison. The Department of Health and Human Services determined that genes and protein products of BoNT/A encoding three LC mutations (E224A/R363A/Y366F), termed M) do not meet the regulatory definition of a select agent, allowing production of M-BoNT/A without select agent registration (§ 73.3 HHS select agents and toxins 42 CFR 73.3 (e)(1).

*Botulinum* Neurotoxins: BoNT/A1, /A2, /A3 and /A5 were purified from *C. botulinum* strains Hall A-hyper, Kyoto-F, CDC A3 (provided by Susan Maslanka and Brian Raphael, Centers for Disease Control and Prevention) and A661222 by standard toxin purification protocols (Jacobson et al., 2011; Lin et al., 2010; Malizio et al., 2000; Tepp et al., 2012). BoNT/A6 was purified from CDC41370 B2tox$^-$ (modified from strain CDC41370 to produce only BoNT/A6) toxin using previously described methods (Pellett et al., 2016). Toxin purity was confirmed by spectroscopy and SDS-PAGE analysis (Whitemarsh et al., 2013). Purified toxins were stored in phosphate buffered saline with 40% glycerol at −20° C. until use. Activities of the five subtype preparations were determined using a standard intraperitoneal mouse bioassay (MBA) as previously described (Hatheway, 1988; Schantz, 1978). The half-lethal dose of each toxin was defined as 1 mouse LD50 Unit (U). Specific activities of the BoNT/A subtypes were; 8 pg/U (Al), 7.9 pg/U (A2), 17 pg/U (A3), 7.3 pg/U (A5), and 5.9 pg/U (A6).

Recombinant BoNT Derivatives: Production of $HC_C$A1 (W1266A) ($HC_C$/A1$^W$), LC/A1 (R363A/Y366F) (LC/A1$^{RY}$), $LCHC_N$/A1 (E224A/R363A/Y366F) (M-$LCHC_N$/Al), BoNT/A1 (E224A/R363A/Y366F) (M-BoNT/A1), BoNT/A1 (E224A/R363A/Y366F/W1266A) (M-BoNT/A1$^W$) and non-catalytic-Tetanus toxin (R372A/Y375F) (TeNTRY) was performed as previously described (Przedpelski et al., 2013). Briefly, *E. coli* were grown overnight on LB agar with 50 μg/ml kanamycin at 37° C. Cultures were inoculated into LB medium (400 ml) containing kanamycin for 3-6 hours with shaking at 37° C. to an OD600 of ~0.6 when 1.0 mM IPTG was added, followed by an overnight incubation with shaking at 16° C. Cells were harvested and the pellet was suspended in lysis buffer (20 mM Tris (pH 7.9), 500 mM NaCl, 5 mM Imidazole, RNase, DNase, and protease inhibitors) (Sigma). Cells were broken with a French Press, clarified by centrifugation, and filtered through a 0.45 μm Surfactant-Free Cellulose Acetate membrane (Thermo Fischer). Lysates were further purified by tandem gravity-flow chromatography using $Ni^{2+}$-NTA resin (Qiagen), p-aminobenzamidine-agarose (Sigma), and Strep-tactin Superflow high-capacity resin (IBA-LifeSciences). Purified proteins were dialyzed into 10 mM Tris (pH 7.9), 200 mM NaCl, and 40% glycerol and stored at −20° C. Recombinant proteins used in this study are shown (FIG. 1). The nucleotide sequence encoding M-BoNT/A1$^W$ is set forth as SEQ ID NO:4 (see FIG. 9).

Vaccine Challenge: Groups of female ICR mice (18 to 22 g) were immunized intraperitoneally with either $HC_C$/A1$^W$, M-$LCHC_N$/A1, M-BoNT/A1, or M-BoNT/A1$^W$ at the indicated concentration mixed with an equal volume of alhydrogel as an adjuvant. Non-trypsinized M-BoNT/A1 and M-BoNT/A1$^W$ were used as vaccines. Vaccines were administered on day 1 and 14, blood was collected by maxillary bleed on day 21, and mice were challenged with BoNT/A1, BoNT/A2, or a BoNT-/A2, /A3, /A5, A6 cocktail as indicated on day 26. At least eight mice per group were used in each experiment as indicated. Results were evaluated for statistical relevance by two-tailed, paired student t-test with a p=0.05.

Figure 6:
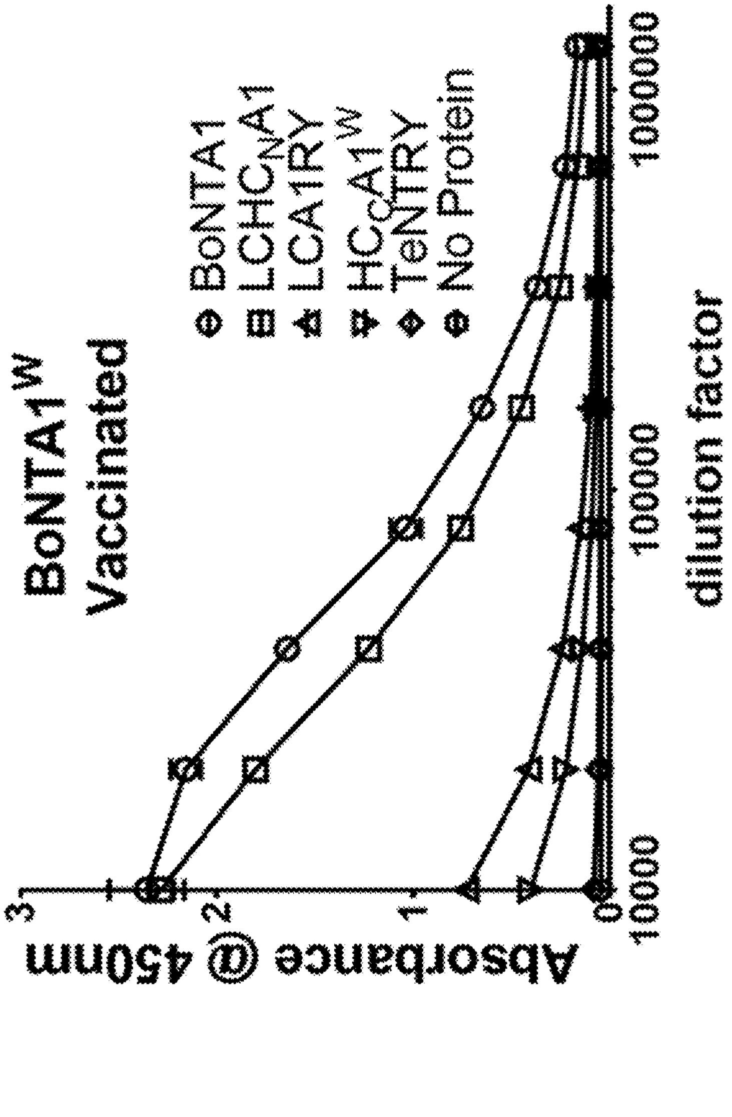
FIG. 6 is a representative ELISA of serum from a mouse vaccinated with M-BoNT/A1$^W$ that survived challenge by BoNT/A1. Serum from a BoNT/A1$^W$ vaccination of a mouse surviving BoNT/A1 challenge was analyzed by ELISA as described in the Methods Section, using the indicated antigens. Values are the average of a representative determination performed in duplicate with standard deviation indicated.

ELISA: BoNT derivatives or TeNT$^{RY}$ (250 ng/well) were added in 0.1 ml of coating buffer, 50 mM $Na_2CO_3$ (pH 9.6) to high protein binding 96-well plates (Corning) and incubated overnight at 4° C. Plates were then washed three times with 0.3 ml of phosphate-buffered saline (PBS) with 0.05% Tween 20 and blocked at room temperature (RT) for 30 minutes with 0.2 ml of PBS with 1% (wt/vol) bovine serum albumin (BSA). Plates were incubated at RT for 1 h with the indicated dilution of serum either 1:20,000 or 1:30,000 from individually vaccinated mice in PBS with 1% (wt/vol) BSA (0.1 ml). After washing three times with 0.3 ml PBS with 0.05% Tween 20, plates were incubated at RT for 1 hour with goat α-mouse IgG-horseradish peroxidase (IgG-HRP diluted 1:20,000; Thermo) in PBS with 1% (wt/vol) BSA. Plates were washed three times with 0.3 ml PBS with 0.05% Tween 20 and then incubated with 0.1 ml per well tetramethyl benzidine (TMB; Thermo Ultra TMB) as substrate. Reactions were terminated after 10 min with 0.1 ml of 0.1 M $H_2SO_4$, and absorbance was read at 450 nm. Control ELISAs, measuring bound antigens with α-HA and α-FLAG antibodies showed the presence of the appropriate epitope within each antigen, within 15% (data not shown). For the ELISA, statistical analyses were performed on groups of individually analyzed sera (N=10) based upon immunization and/or challenge conditions by two tailed, unpaired Student t test with $P<0.05$=*, 0.01=, 0.001=*, and 0.0001=** (GraphPad Prism 7). Individual sera were analyzed by at least two-independent ELISA performed in duplicate. Analysis of mouse serum at 1:20,000-1:30,000 fold dilutions was based upon assessment of several individual sera. The serum dilutions were established from a dose-response ELISA of several mice vaccinated with M-BoNT/A1 which survived challenge with BoNT/A1. A representative ELISA is shown in FIG. 6**.

Cell based assay for detection of neutralizing antibodies: Cell based neutralization assays were performed as previously described (Whitemarsh et al., 2012). Briefly, human induced pluripotent stem cell (hiPSC) derived neurons (Cellular Dynamics International, WI) were seeded into poly-L-ornithine and Matrigel™ coated 96-well TPP plates (Midwest Scientific, MO) at a density of about 35,000-40,000 cells per well and maintained in iCell Neurons culture media (Cellular Dynamics International, WI) according to manufacturer's instructions for 7 days prior to the neutralization assay. To detect neutralizing antibodies in the mouse sera, 2 pM of BoNT/A1 was combined with serial dilutions of sterile filtered sera in culture media and incubated for 1 hour at 37° C. BoNT/A1 without sera was used as a 'no antibody' reference, and serum from naïve mice was used as a control. Serum without toxin was used as a negative control. Fifty μl of each antibody-toxin mixture was added per well of hiPSC derived neurons in at least duplicates, respectively, and cells were incubated for 24 hours at 37° C., 5% $CO_2$. The toxin/antibody was aspirated from the cells, and cell lysates were prepared in 50 μl of lithium dodecyl sulfate (LDS) sample buffer (Life Technologies). The cell lysates were analyzed by Western blot for SNAP-25 cleavage as previously described (Pellett et al., 2007; Pellett et al., 2010). Images were obtained using PhosphaGlo reagent (KPL, Gaithersburg, Md.) and a Fotodyne/FOTO/Analyst FX imaging system (Harland, Wis.). Cleaved (24 kDa) versus uncleaved (25 kDa) SNAP-25 signal was analyzed by densitometry using TotalLab Quant software (Fotodyne, Harland, Wis.). Percentage of protection was determined by comparison to the 'no-antibody' control, and $IC_{50}$ values were estimated, using GraphPad Prism 6 software and a nonlinear regression, variable slope, four parameters.

Results

M-BoNT/A1 is Not Toxic to Outbred Mice or Cells in Culture

Ten μg of either trypsinized- or non-trypsinized-M-BoNT/A1/mouse (ICR) injected intraperitoneal did not result in observable signs of botulism, indicating M-BoNT/A1 was at least one million-fold less toxic than native BoNT/A1. In addition, incubation of human iPSC derived neurons with 80 nM M-BoNT/A1 did not yield detectable SNAP-25 cleavage, while incubation with 50 fM native BoNT/A1 cleaved SNAP-25, indicating at least a million-fold lower toxicity by the cell based assay (data not shown).

M-BoNT/A1 and M-BoNT/A1$^W$ are More Protective Vaccines than $HC_C$/A1$^W$

Figure 2:
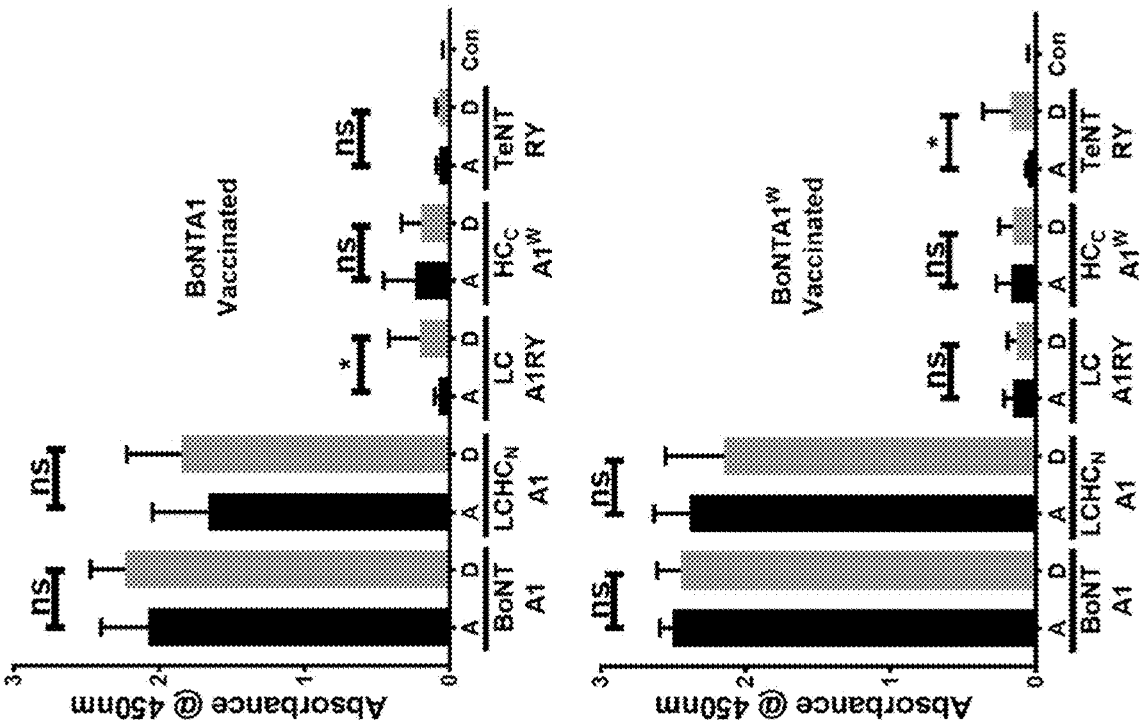
FIG. 2 is an ELISA of sera from mice vaccinated with M-BoNT/A1 or M-BoNT/A1$^1$ and challenge by native BoNT/A2, a heterologous subtype. Mice were vaccinated with M-BoNT/A1 (upper panel) or M-BoNT/A1$^1$ (lower panel) and sera collected prior to a $10^6$ LD50 native BoNT/A2 challenge. Mice surviving (A) or non-surviving (D) challenge are indicated. ELISAs were performed measuring antibody titers of sera (1:20,000 dilution) for M-BoNT/A1; M-LCHC$_N$/A1; LC/A1$^{RY}$; HC$_C$/A1$^W$; TeNT$^{RY}$; and no protein control (Con). Bound mouse antibodies were detected with goat α-mouse IgG-HRP (1:20,000 dilution), using TMB reagent. Reactions were stopped with dilute $H_2SO_4$ and read @ 450 nm. Data are presented as the average of 5 mice (A) and 4 mice (D) following M-BoNT/A1 vaccination and 3 mice (A) and 6 mice (D) following M-BoNT/A1$^W$ vaccination from two independent experiments performed in duplicate with standard deviation indicated. Statistical analyses were performed as described herein: P, 0.05=*.

Vaccine challenges were conducted on outbred ICR mice (n=8-10) to reflect natural immune variance within the host (Rai et al., 2009), using a primary immunization followed by one boost. Since previous studies showed $HC_C$/A1 (W1266A) ($HC_C$/A1$^W$) had similar vaccine potency in the mouse model of botulism as $HC_C$/A1 (Przedpelski et al., 2013), M-BoNT/A1$^W$ was also engineered. Mice vaccinated with 0.3 μg/mouse single chain M-BoNT/A1$^W$ or 0.2 μg/mouse M-LCHC$_N$/A1 were protected against challenge by $10^6$ $LD_{50}$ of native BoNT/A1 or $10^5$ $LD_{50}$ of a BoNT/A subtype cocktail ($2.5\times10^4$ $LD_{50}$ each A2, A3, A5, A6) and partially protected against challenge by $10^6$ $LD_{50}$ of native BoNT/A2, a heterologous subtype (Table 4). Mice vaccinated with 0.1 μg/mouse $HC_C$/A1$^W$ were partially protected against challenge by $10^3$ $LD_{50}$ of native BoNT/A1 or native BoNT/A2. These data indicate that at equimolar doses, the M-BoNT/A1$^W$ and the M-LCHC$_N$/A1 vaccines protected against 1,000-fold more toxin than the $HC_C$/A1$^W$ vaccine. In a comparison of the vaccines using weight equivalent doses, mice vaccinated with 0.3 μg/mouse of $HC_C$/A1$^W$, were partially protected against challenge by $10^5$ $LD_{50}$ of native BoNT/A1 or $10^5$ $LD_{50}$ of native BoNT/A subtype cocktail. This indicates that even at equal concentrations (and a 3-fold molar excess of $HC_C$), the M-BoNT/A1$^W$ and the M-LCHC$_N$/A1 vaccines protected better against homologous and heterologous BoNT/A challenge. No difference in protection of the M-BoNT/A1$^W$ and M-BoNT/A1 vaccine were noted, indicating that the additional 'receptor binding' mutation does not affect vaccine potency. Overall, M-BoNT/A1, M-BoNT/A1$^W$ and M-LCHC$_N$/A1 were more potent vaccines than $HC_C$/A1$^W$. Duration of action in cultured neurons was further investigated in human iPSC derived neurons by exposing the neurons to serial dilutions of either BoNT/A1 or BoNT/A6 for 72 hours, followed by complete removal of extracellular toxin, and further incubation in culture media. Cells with each dilution series were harvested at days 3, 39, and 70 in triplicate, and the $EC_{50}$ for SNAP-25 cleavage was determined for each time point. For BoNT/A6, $EC_{50}$ values were ~0.04, 0.7, and 1 U/50 μl/well (32, 560, and 800 fM) at days 3, 39, and 70, respectively (FIG. 2). For BoNT/A1 $EC_{50}$ values were ~0.7, 6.3, and 28 U/50 μl/well (313, 2940, and 12,880 fM, respectively) at days 3, 39, and 70 (FIG. 2). The half-life of BoNT/A1 and /A6 in these hiPSC derived neurons as determined from the $EC_{50}$ values over time was similar for both BoNT/A1 and /A6, approximately 12 days and 14 days, respectively (FIG. 2). Taken together, these results indicate that BoNT/A6 has a long duration of action, similar to other BoNT/A subtypes.

Antibody responses to BoNT vaccination varied qualitatively and quantitatively in outbred mice.

Vaccination with M-BoNT/A1$^W$ and M-BoNT/A1 provided complete protection to challenge by $10^5$ $LD_{50}$ BoNT/A2 and partial protection to challenge by $10^6$ $LD_{50}$ of native BoNT/A2, a heterologous subtype (Table 5). Antibody responses of vaccinated mice analyzed by ELISA showed mice surviving or not surviving native BoNT/A2 challenge had similar dominant antibody titers to BoNT and LCHC$_N$, which were not statistically different (FIG. 2). Thus, partial protection against native BoNT/A2 challenge appears to be due to specific differences in the composition of neutralizing epitopes between BoNT/A subtypes, not the ability of the vaccinated mice to mount an immune response to the delivered vaccine.

TABLE 5

Vaccine potency of recombinant BoNT and BoNT-derivatives in the mouse model of botulism

| Vaccine Primary & Boost (μg)[a] | Challenge BoNT serotype | Survivors/Challenged Units of BoNT/A $LD_{50}$ challenge (U)[b] $10^3$ U | $10^4$ U | $10^5$ U | $10^6$ U |
|---|---|---|---|---|---|
| Experiment 1 | | | | | |
| M-BoNT/A1 (0.3) | A1 | 10/10 | —[c] | — | — |
| | A2 | 10/10 | — | — | — |
| M-BoNT/A1$^{W}$[d] (0.3) | A1 | 10/10 | — | — | — |
| | A2 | 10/10 | — | — | — |
| $HC_C$/A1$^W$ (0.1) | A1 | 7/10 | — | — | — |
| | A2 | 6/10 | — | — | — |
| Alum | A1 | 0/5 | — | — | — |
| Experiment 2 | | | | | |
| M-BoNT/A1 (0.3) | A2 | — | 8/8 | 8/8 | 5/9 |
| M-BoNT/A1$^W$ (0.3) | A2 | — | 8/8 | 8/8 | 3/9 |
| Alum | A2 | — | — | — | 0/5 |
| Experiment 3 | | | | | |
| M-BoNT/A1$^W$ (0.3) | A1 | — | — | — | 10/10 |
| M-LCHC$_N$/A1 (0.2) | A1 | — | — | — | 10/10 |
| M-LCHC$_N$ (0.2) + $HC_C$/A1$^W$ (0.1) | A1 | — | — | — | 10/10 |

TABLE 5-continued

Vaccine potency of recombinant BoNT and BoNT-derivatives in the mouse model of botulism

| Vaccine Primary & Boost (μg)[a] | Challenge BoNT serotype | Survivors/Challenged Units of BoNT/A $LD_{50}$ challenge (U)[b] | | | |
|---|---|---|---|---|---|
| | | $10^3$ U | $10^4$ U | $10^5$ U | $10^6$ U |
| $HC_C$/A1[W] (0.3) | A1 | — | — | 7/10 | — |
| M-BoNT/A1[W] (0.3) | A(subtype cocktail)[e] | — | — | 10/10 | — |
| M-$LCHC_N$/A1 (0.2) | A(subtype Cocktail) | — | — | 10/10 | — |
| M-$LCHC_N$/A1 (0.2) + $HC_C$/A1[W] (0.1) | A(subtype Cocktail) | — | — | 9/10 | — |
| $HC_C$/A1[W] (0.3) | A(subtype Cocktail) | — | — | 7/10 | — |
| Alum | A(subtype Cocktail) | — | 0/5 | — | — |

[a]Mice were immunized IP with the indicated vaccine with alhydrogel as adjuvant. Vaccines were administered on day 1 and 14, blood was collected on day 21, and mice were challenged as indicated on day 26

[b]U = One half-lethal dose of a botulinum neurotoxin at 72 h post challenge is defined as 1 mouse $LD_{50}$

[c]— = not determined

[d] W = W1266A mutation within the ganglioside binding domain of HC/A1

[e]A(subtype cocktail) = 25,000 $LD_{50}$ U of BoNT/A2/A3/A5 and /A6 (total 100,000 $LD_{50}$ U)

Figure 3:
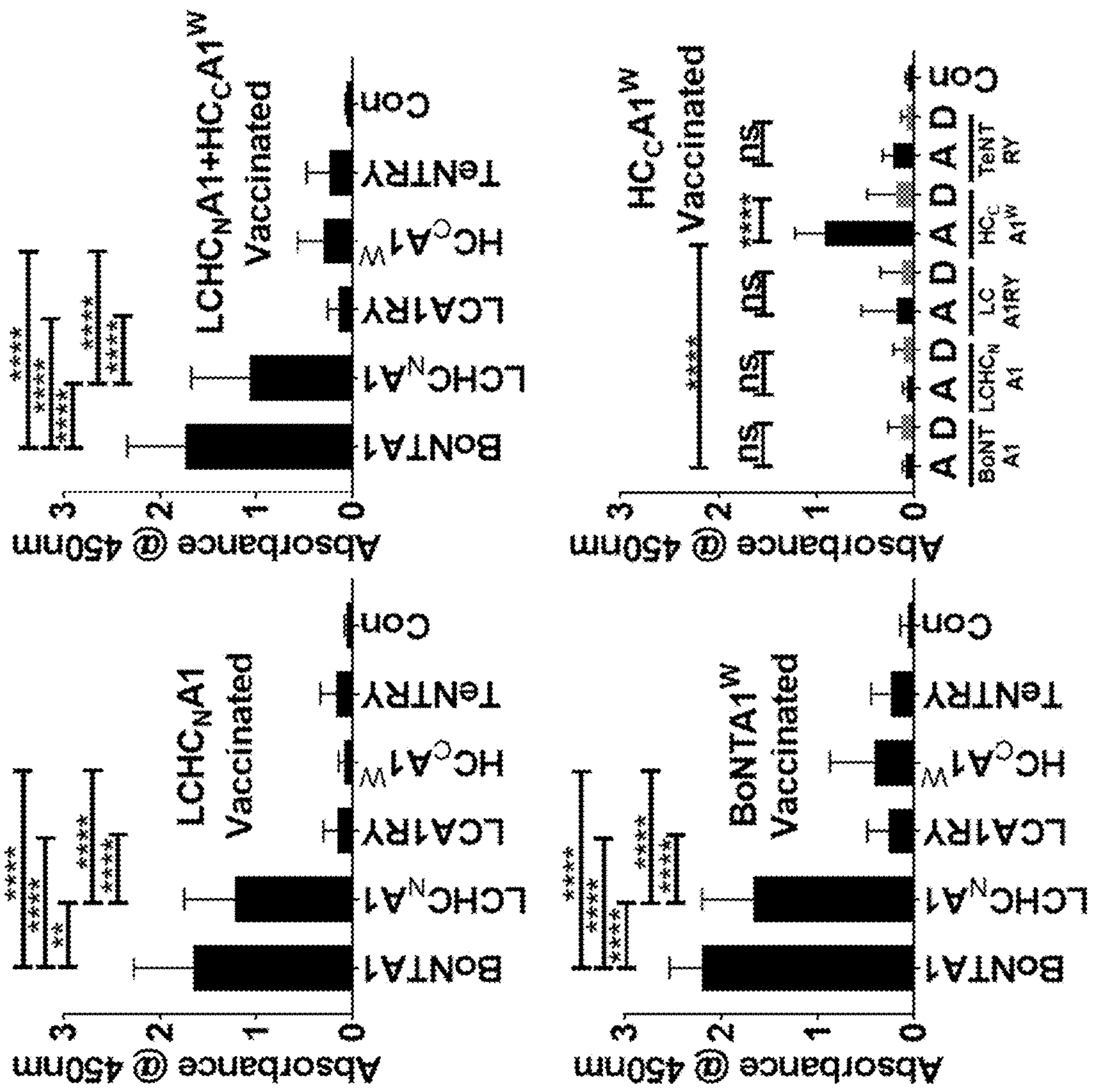
FIG. 3 is an ELISA of sera from mice vaccinated with BoNT derivatives and challenged with native BoNT/A1. Mice were vaccinated with M-BoNT/A1$^W$ (0.3 μg), M-LCHC$_N$/A1 (0.2 μg), M-LCHC$_N$/A1 (0.2 μg)+HC$_C$/A1$^W$ (0.1 μg), or HC$_C$/A1$^W$ (0.3 μg). Sera were obtained prior to BoNT challenge. ELISAs determining antibody titers of sera (1:30,000 dilution) for M-BoNT/A1; M-LCHC$_N$/A1; LC/A1$^{RY}$; HC$_C$/A1$^W$; TeNT$^{RY}$; and no protein control (Con). Bound mouse antibodies were detected with goat α-mouse IgG-HRP (1:20,000 dilution), using TMB reagent. Reactions were stopped with dilute $H_2SO_4$ and read @ 450 nm. Data are presented as the average of 10 independent sera of mice surviving BoNT/A1 challenge from Experiment 3 in Table 1 analyzed in two independent experiments performed in duplicate with standard deviation indicated; except for mice vaccinated with HC$_C$/A1$^W$ where the data are from 7 survivors (A) or 3 non-survivors (D) of native BoNT/A1 challenge. Variance in the range of titers was due to the varied antibody titers among individual mice, not to variance in the ELISA replicates. Statistical analyses were performed as described in Methods Section: P<0.05=*, 0.01=, 0.001=*, and 0.0001=****.
Figure 7:
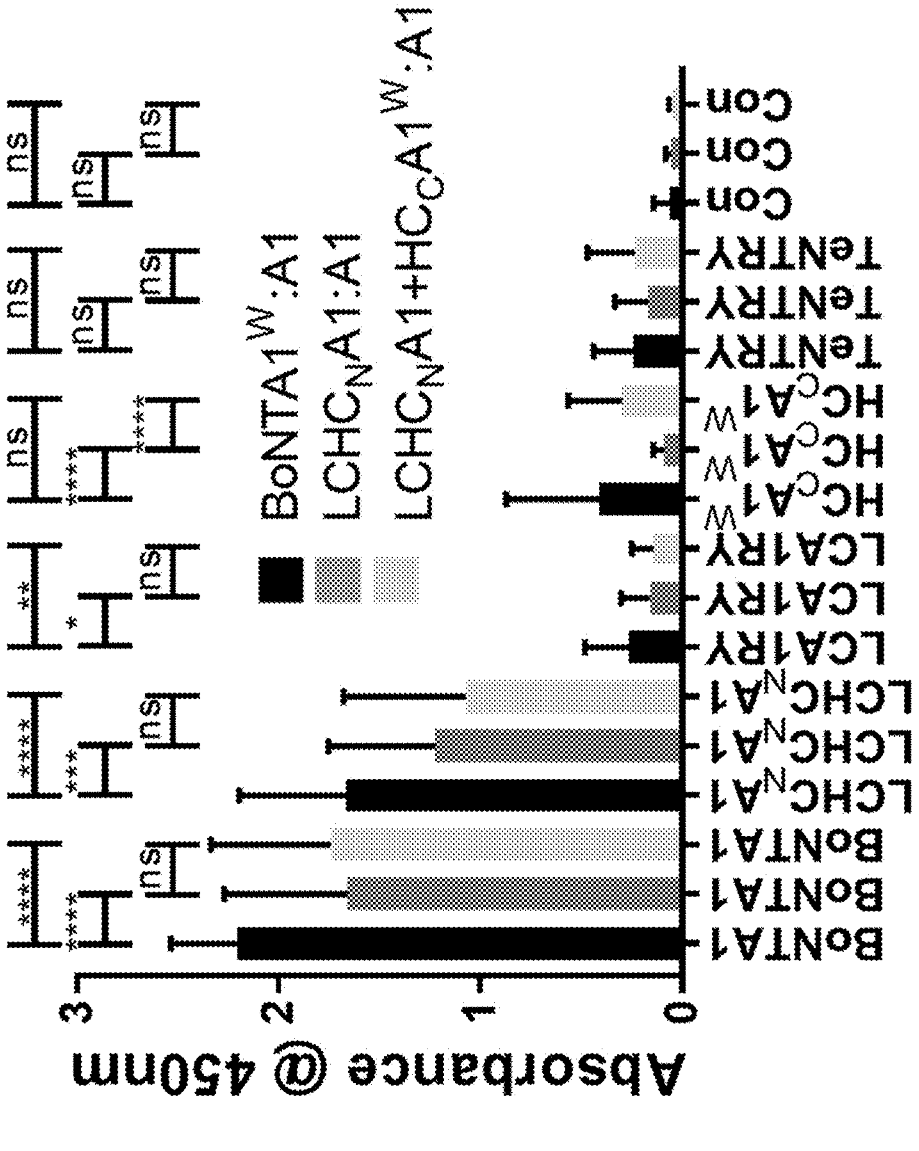
FIG. 7 demonstrates that M-BoNT/A1$^W$ is more immunogenic than M-LCHC$_N$/A1, or LCHC$_N$/A1+HC$_C$/A1$^W$. Sera from individual mice vaccinated with M-BoNT/A1 (0.3 μg), M-LCHC$_N$/A1$^W$ (0.2 μg), or M-LCHC$_N$/A1 (0.2 μg)+HC$_C$/A1$^W$ (0.1 μg) surviving challenged with $10^6$ LD$_{50}$BoNT/A1 were analyzed by ELISA for antibodies to M-BoNT/A1, M-LCHC$_N$/A1, LC/A1$^{RY}$, HC$_C$/A1$^W$, TeNT$^{RY}$, or no protein (Con). Data are presented as the average of 10 independent sera of mice surviving BoNT/A1 challenge from Experiment 3 in Table 1 analyzed in two independent experiments performed in duplicate with standard deviation indicated. Statistical analyses were performed as described in Methods Section: P<0.05=*, 0.01=, 0.001=*, and 0.0001=****.

Antibody responses of vaccinated mice were analyzed by ELISA of individual sera using either the LCA1[RY], $HC_C$/A1[W], M-$LCHC_N$/A1, or M-BoNT/A1 holotoxin as binding substrates. The antibody response within each group of vaccinated mice varied within the group quantitatively and qualitatively. Mice vaccinated with M-BoNT/A1[W] (FIG. 3, lower left) showed dominant antibody titers to BoNT (mean titer 2.2 (range 1.3-2.6)) and $LCHC_N$ (mean titer 1.7 (range 0.8-2.4)). Titers to $HC_C$ varied between mice (mean titer 0.41 (range 0.07-1.83)). Titers to LC were not above controls, indicating most of the antibody response was directed towards the HC. Variance in the range of titers was due to the varied antibody titers among individual mice, not to variance in the ELISA replicates. A similar immune response to M-BoNT/A1 vaccination was observed (data not shown). Mice vaccinated with M-$LCHC_N$/A1 (FIG. 3, upper left) also had dominant antibody titers to BoNT and $LCHC_N$, with on average lower titers than mice vaccinated with M-BoNT/A1[W]. Mice vaccinated with M-$LCHC_N$/A1+$HC_C$/A1[W] had antibody titer profiles that were qualitatively like mice vaccinated with M-BoNT/A1[W], quantitatively they compared to mice vaccinated with M-$LCHC_N$/A1 alone (FIG. 7). Mice vaccinated with $HC_C$/A1[W] had antibody titers to $HC_C$ that correlated with survival to BoNT/A1 challenge (FIG. 3, lower right). Mice vaccinated with M-BoNT/A1[W] possessed limited antibody titers to TeNT[RY] (FIG. 3), indicating that the observed antibody responses were BoNT-specific.

Figure 4:
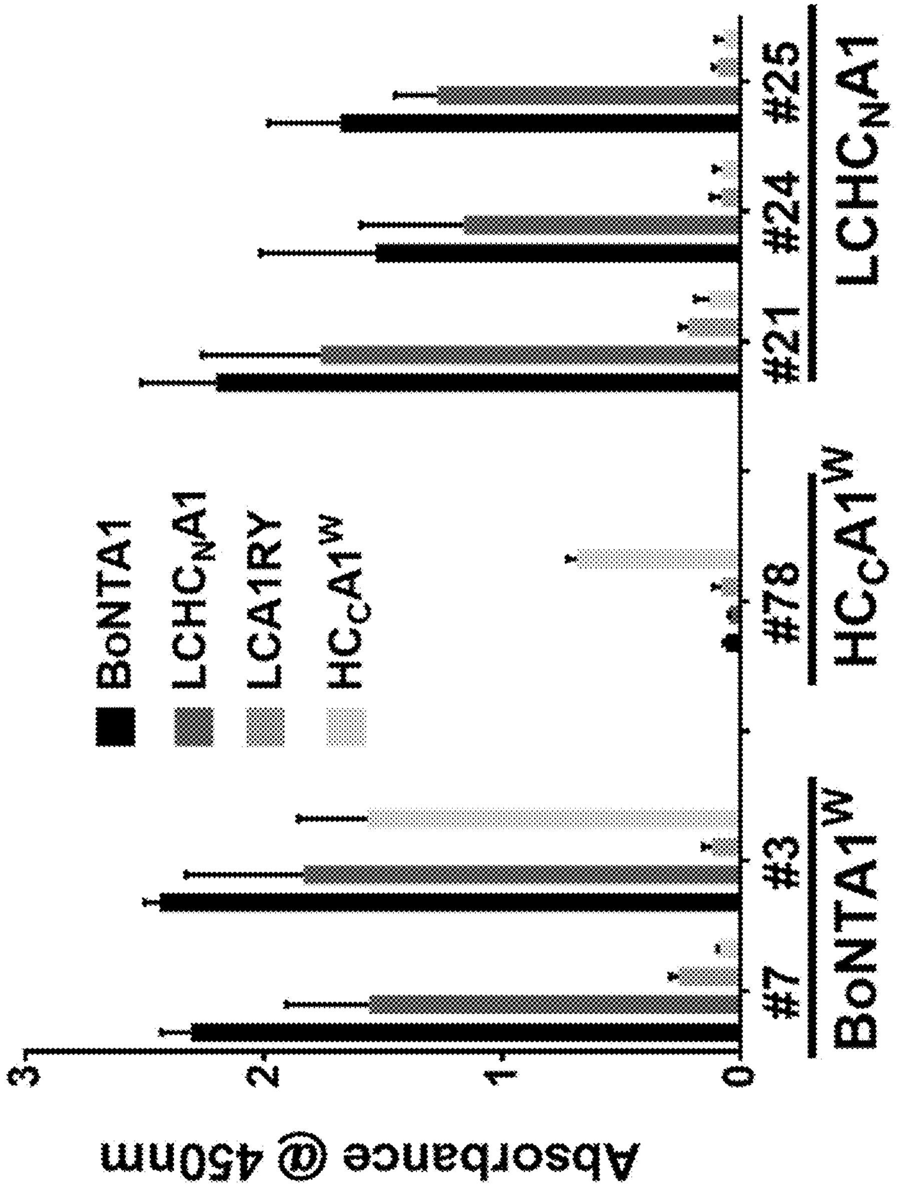
FIG. 4 is an ELISA of serum from individual mice vaccinated with M-BoNT derivatives and surviving challenge by native BoNT/A1. Sera obtained prior to BoNT challenge from individual mice vaccinated with BoNT/A1$^W$ (#7 and #3), HC$_C$/A1$^W$ (#78) and LCHC$_N$/A1 (#21, #24, and #25) surviving native BoNT/A1 challenge were analyzed by ELISA (1:30,000 dilution) using M-BoNT/A1; M-LCHC$_N$/A1; LC/A1$^{RY}$; HC$_C$/A1$^W$ as antigens. Bound mouse antibodies were detected with goat α-mouse IgG-HRP (1:20,000 dilution), using TMB reagent. Reactions were stopped with dilute $H_2SO_4$ and read @ 450 nm. Data presented are the average of two independent experiments each performed duplicate with standard deviation indicated.

Properties of sera from individually vaccinated mice surviving BoNT challenge. Analysis of individual sera from mice vaccinated with M-BoNT/A1[W], M-$LCHC_N$/A1, or $HC_C$/A1[W] surviving native BoNT/A1 challenge showed several representative immune responses to vaccination (FIG. 4). Since our earlier studies (Przedpelski et al., 2013 *Infect Immun.* 81(7):2638-44) did not characterize the antibody response to M-$LCHC_N$/A1 vaccination, sera from three $LCHC_N$/A1 vaccinated mice were analyzed. ELISA results showed mice vaccinated with M-BoNT/A1[W] had dominant antibody titers to BoNT and $LCHC_N$ (#7) or to BoNT, $LCHC_N$, and $HC_C$ (mouse #3). Mice vaccinated with M-$LCHC_N$/A1 showed dominant antibody responses to BoNT and $LCHC_N$ (mice #21, #24, and #25), while mice vaccinated with $HC_C$/A1[W] and surviving BoNT/A1 challenge had a dominant antibody response to $HC_C$ (mouse #78). Overall, the antibody responses to TeNT[RY] were low, indicating that the immunoreactivity detected in the ELISA were specific to BoNT.

The BoNT/A and $HC_C$ vaccines elicit stronger neutralizing antibody response than the $LCHC_N$ vaccine.

Figure 5:
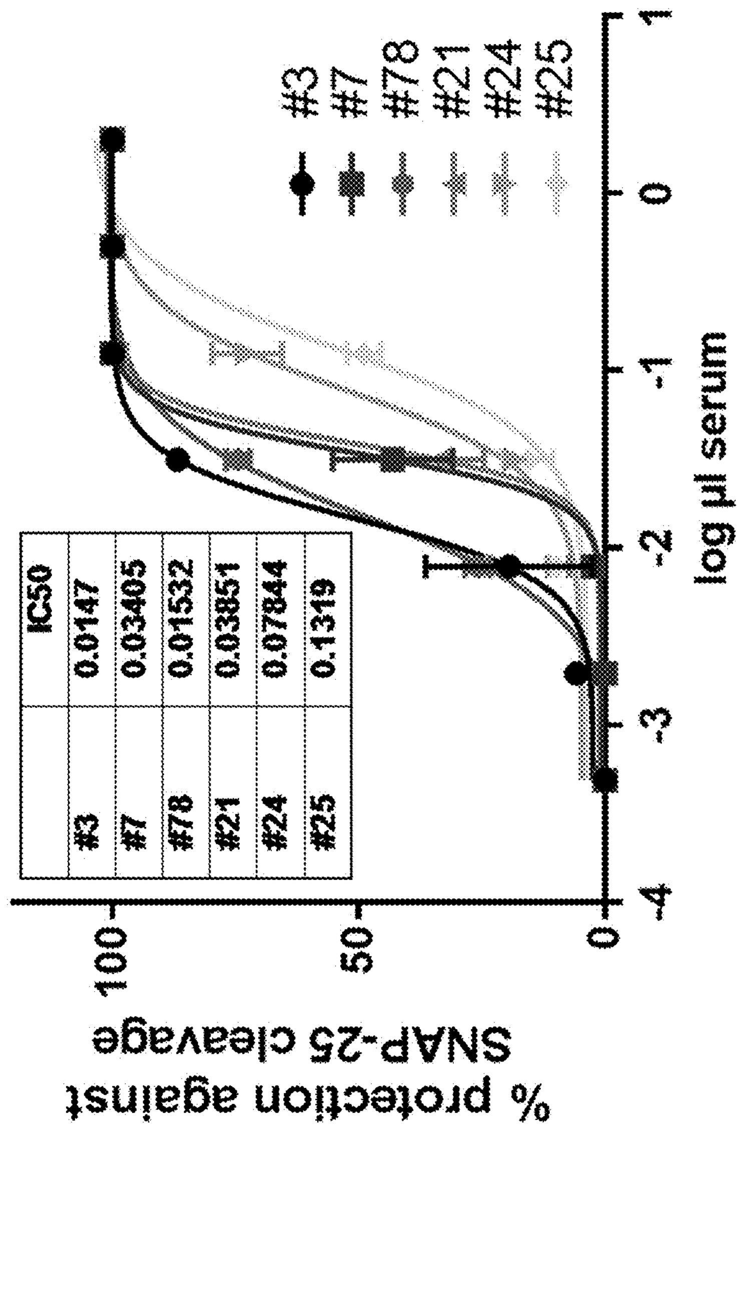
FIG. 5 demonstrates serum neutralization of native BoNT/A1 cleavage of SNAP25 in human induced pluripotent stem cells (hiPSCs). Sera obtained prior to BoNT challenge from individual mice vaccinated with M-BoNT/A1$^W$ (#7 and #3), HC$_C$/A1$^W$ (#78) and M-LCHC$_N$/A1 (#21, #24, and #25) surviving BoNT/A1 challenge were analyzed for their capacity to neutralize native BoNT/A1. Human induced pluripotent stem cell (hiPSC)-derived neurons were seeded into poly-L-ornithine and Matrigel coated plates at a density of 35,000-40,000 cells per well and maintained in iCell Neurons culture media for 7 days prior to the neutralization assay. To detect neutralizing antibodies in the mouse sera, 2 pM of native BoNT/A1 was combined with serial dilutions of sterile filtered sera and in culture media and incubated for 1 hour at 37° C. A 'no-antibody' buffer was used as a control. Fifty μl of each antibody-toxin mixture was added per well of hiPSC derived neurons in at least duplicates and cells were incubated for 24 h at 37° C., 5% $CO_2$. The toxin/antibody was aspirated from the cells, and cell lysates were subjected to PAGE followed by analyzed by Western blot for SNAP-25 cleavage (Pellett et al., 2007; Pellett et al., 2010). Cleaved versus noncleaved SNAP-25 was quantified by densitometry and the % of protection was determined by comparison to the 'no-antibody' control. IC$_{50}$ values were estimated using GraphPad Prism 6 software and a nonlinear regression, variable slope, four parameters.

The neutralizing antibodies in vaccinated mouse sera were measured by cell-based assay using hiPSC derived neurons. From each vaccination group of the equimolar vaccination challenge, 10 sera were pooled and tested for their ability to neutralize BoNT/A1 induced cleavage of SNAP25 in the cell based assay. M-BoNT/A1[W] vaccinated pool was most potent for neutralization with an $IC_{50}$ value of 0.004, which was about 2-fold lower than the $HC_C$/A1[W] vaccinated pool and the M-$LCHC_N$/A1+$HC_C$/A1[W] vaccinated pool, and about 5-fold lower than the M-$LCHC_N$/A1 vaccinated pool (data not shown). The similarity in neutralizing antibody titers in mice vaccinated with $HC_C$ and M-BoNT/A1 was striking considering that the M-BoNT/A1 vaccine protected mice against >1,000-fold greater toxin challenge than the $HC_C$ vaccine. To investigate this further, the ability of six representative individual sera to neutralize BoNT/A1 cleavage of SNAP25 in a cell based assay was also determined (FIG. 5). Overall, each of the six sera neutralized BoNT/A1 action with ~10-fold difference in the serum potency. Sera from $HC_C$/A1[W] vaccination (mouse #78) and M-BoNT/A1[W] vaccination (mouse #3), which contained a dominant antibody response to $HC_C$ (FIG. 4), were the most potent inhibitors of BoNT/A1 cleavage of SNAP-25. Sera without a detectable $HC_C$ antibody response (mice #7, #21, #24, and #25), were less effective in inhibiting SNAP-25 cleavage. Thus, in this assay, vaccines with $HC_C$ epitopes elicited a greater ‘neutralizing/blocking antibody’ response than the $LCHC_N$ vaccine. Together, these data indicate that the $HC_C$ domain of BoNT/A1 elicits a stronger neutralizing/blocking antibody response than the $HC_N$ or LC domains, but that the $HC_N$ and possibly the LC domain play a major role in in vivo protection.

Discussion

In an outbred mouse model of botulism, M-BoNT/A1, M-BoNT/A1[W] and M-$LCHC_N$/A1 were more potent vaccines than $HC_C$/A1[W]. Assessment of sera from vaccinated mice that survived BoNT/A1 challenge showed a common response to $LCHC_N$ consistent with the presence of neutralizing epitopes within $LCHC_N$. The ability of M-BoNT/A1[W] to elicit a similar protective immune response relative to M-BoNT/A1 showed reduction of host cell binding did not negatively affect vaccine efficacy. Thus, full-length BoNT engineered with defects in both the catalytic and receptor binding domains represents a novel platform strategy for development of vaccines against botulism and other toxin-mediated diseases. Collier and coworkers (Killeen et al., 1992) showed the ability to generate second-site mutations that partially reverted a genetically inactivated diphtheria toxin as a test for vaccine development. In addition, recent studies by Smith and coworkers show a need for greater attenuation than only reduction of catalysis for several serotypes of BoNT-based vaccines (Webb et al., 2017).

In an earlier study, $LCHC_N$ was described as a BoNT vaccine candidate (Shone et al., 2009). $LCHC_N$ was produced in high amounts by *E. coli* by fermentation and was effective as a single dose vaccine to a low dose BoNT challenge ($10^3$ $LD_{50}$ of BoNT). In this report, we observed that $LCHC_N$ was a potent vaccine by direct comparison to other BoNT vaccine candidates, using a primary immunization with one boost and confirmed the presence of neutralizing epitope(s) within LCHCN (Shone et al., 2009). Dolly and colleagues identified a LC specific monoclonal antibody (Mab) that prevented BoNT/A action (Cenci Di Bello et al., 1994), while Marks and colleagues identified BoNT/A neutralizing mAbs with LC function that inhibited SNARE cleavage (Cheng et al., 2009) and mAbs that targeted $HC_N$ and neutralized several BoNT serotypes (Garcia-Rodriguez et al., 2011). Together, these studies indicate that BoNT vaccination elicits the production of antibodies to neutralizing epitopes within the $LCHC_N$ domains. Since M-BoNT/A1$^W$ elicited a greater antibody response than M-$LCHC_N$/A1 (FIG. 7), along with the determination that $HC_C$ produced antibodies with the greatest neutralizing/blocking potencies in cultured cells, vaccines that include $HC_C$, such as M-BoNT/A1$^W$, would be expected to be more protective in a 'high-dose' exposure scenario than $LCHC_N$ or $HC_C$ vaccine derivatives.

The $HC_C$ is a popular domain to develop vaccines against botulism, using DNA- and viral-vectors, as well as protein-base vaccines built upon earlier studies showing neutralizing potency of the $HC_C$ (Clayton et al., 1995) and ease of production (Baldwin et al., 2008). Smith and colleagues expressed $HC_C$ in the yeast, *Pichia pastoris*, and reported protective immunity elicited by HC(c) (Byrne and Smith, 2000) and subsequently, a bivalent vaccine composed of recombinant $HC_C$/A and $HC_C$/B (rBV A/B), which is now in clinical trial (Webb and Smith, 2013). *E. coli* has also been used as a heterologous host for BoNT vaccine development, including production of a seven serotype (A-G) $HC_C$-vaccine against BoNT challenge (Baldwin et al., 2008). To enhance vaccine potency a mutation was introduced to the $HC_C$ blocking host receptor binding, where $HC_C^W$ retained vaccine potency (Przedpelski et al., 2013). While ease of production makes $HC_C$ an attractive vaccine platform, the current study showed M-BoNT/A1$^W$ was a more potent vaccine than $HC_C$/A1W. This is supported by the finding of Atassi and colleagues, who detected immune epitopes within the LC and $HC_N$, using human serum from cervical dystonia patients resistant to BoNT therapy (Atassi et al., 2011; Dolimbek et al., 2007), consistent with the immunogenicity of the $LCHC_N$ of BoNT.

A recent study by Smith and coworkers (Webb et al., 2017) reported that catalytically inactive BoNT showed greater potency to challenge by 1000 $LD_{50}$ toxin challenge after single vaccination than the corresponding $HC_C$. The challenge experiments described by Smith coworkers measured threshold toxin challenges, which differed from the current study that measures protection to endpoint toxin challenge. The data showed that in both cases, either measuring protection to toxin challenge by threshold or endpoint, full-length BoNT vaccines were more potent than their respective $HC_C$ subunits. M-BoNT/A1$^W$, with defects in catalysis and host receptor binding, was effective in the endpoint toxin challenges relative to the subunit. By inactivation of multiple functional sites to lower the potential toxicity due to cell binding or entry, utility of M-BoNT/A1$^W$ as a vaccine candidate addresses a concern that genetic inactivation of catalytic function alone may not provide a sufficient margin of safety for vaccine development of full-length BoNTs (Webb et al., 2017).

While the utility of the $HC_C$ as a vaccine candidate against botulism is established (Baldwin et al., 2008; Henderson, 2006), the current study shows multi-domain derivatives of BoNT are more potent vaccines than $HC_C$. M-BoNT/A1$^W$ elicited a common dominant antibody response to $LCHC_N$, but a varied $HC_C$ antibody response in outbred mice. The ability to reduce both catalysis and receptor binding support the use of M-BoNT/A1$^W$ as a vaccine platform against botulism. Protection against a BoNT/A subtype cocktail confirmed broad neutralization capacity of this vaccine. M-BoNT/A1$^W$ used as a vaccine in this study was not processed to an activated, di-chain form and toxicity was not detected in mice or cells, suggesting single chain M-BoNT/A1$^W$ as a safe and effective vaccine.

Example 2

Characterization of Disrupted Light Chain Translocation in Lysine768 TeNT Variants This section describes the identification and characterization for the first time of a single amino acid point mutation within the translocation domain of TT that blocked light chain (LC) translocation. Identification of a role for K768 in LC translocation provides, for the first time, an opportunity to inactivate independent activities of TT, and by analogy BT (see Table 6), catalysis, translocation, and receptor binding, for recombinant vaccine development.

Using tetanus toxin, we recently identified a rate limiting step in Light Chain (LC) translocation encoded within the translocation domain. Lysine (K) 768 is located in a loop that links two long α-helices (helixl2-13 and helixl6-17). Site directed mutagenesis identified a point mutation K768A, located within the loop that connects the two long α-helices of the translocation domain that inhibited translocation (FIG. 12). Cell studies showed that M-TT(K768A) was did not bind neuronal membranes, which supports a role for the loop in membrane penetration. Control experiments showed that the K768A mutation did not inhibit TT binding, entry, trafficking, or pore formation in hosts cell and did not inhibit the preferred cleavage of Light Chain (LC)-Heavy Chain (HC) by trypsin, indicating that the mutation did not disturb overall M-TT structure and implicating a direct role for the loop in light chain translocation. Other experiments indicated that K768 was not a component of the pH trigger. This is the first single amino acid within the translocation domain that is required to Light Chain translocation and implicates a role for the two long α-helices (helix12-13 and helix16-17) in toxin-membrane interactions. Other experiments demonstrated that a D767A/E769A mutation also yielded a translocation defect in tetanus toxin, making D767/E769 complementary and/or additive to K768 for inhibiting LC translocation in tetanus toxin.

Engineering independent mutations into *botulinum* toxin (BT) (see Table 6) and TT vaccine candidates will inactivate each of the three functions of toxin action: catalysis, translocation, and receptor binding, thus enhancing vaccine safety. Multiple, independent mutations reduce toxin potency exponentially, enhancing vaccine safety without disturbing protein structure and potentially immunogenicity, and reduce reversion potential during large scale production.

TABLE 6

| Exemplary point mutations for 8M-BT/A | | | | | |
|---|---|---|---|---|---|
| M-BT/A | Zn++ binding | Substrate Binding and catalysis | Light Chain translocation | Protein receptor binding | Ganglioside receptor binding |
| | E224Q, R363A, Y366F Termed 3M-BT/A and is >$10^6$-fold less toxic than BT WT | L174A, E370A This double mutation is $4X10^4$-fold less catalytic than LC/AWT | K758A Inhibits LC translocation (preliminary data) | R1156A This mutation Inhibits 5V2 binding, | W1266A This mutation is ~800-fold less toxic than BT WT |
| 4M-BT/A | E224Q, R363A, Y366F | | | | W1266A |
| 5M-BT/A | E224Q, R363A, Y366F | | | R1156A | W1266A |
| 6M-BT/A | E224Q, R363A, Y366F | | K758A | R1156A | W1266A |
| 7M-BT/A | E224Q, R363A, Y366F | D370A | K758A | R1156A | W1266A |
| 8M-BT/A | E224Q, R363A, Y366F | L174A, D370A | K758A | R1156A | W1266A |

Example 3

Engineered M-Tetanus Toxin (M-TT) as a Low Dose Protective Vaccine

Figure 14:
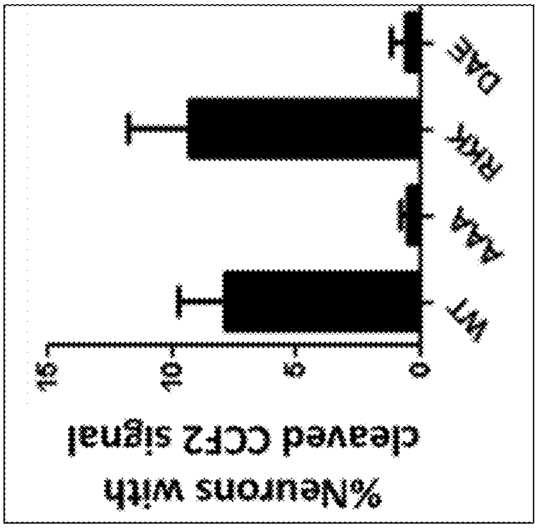
FIG. 14 demonstrates that K768 mediates light chain translocation in tetanus toxin. (left panel) TT$^{767}$DKE (WT), TT$^{767}$AAA, TT$^{767}$RKK, or TT$^{767}$DAE were incubated with neurons and assayed for translocation as reporter (β-lactamase) CCF2 cleavage. (right panel) Alignment of TT and BTs at $^{767}$DKE. Note the conserved lysine (K) among toxins.
Figure 15:
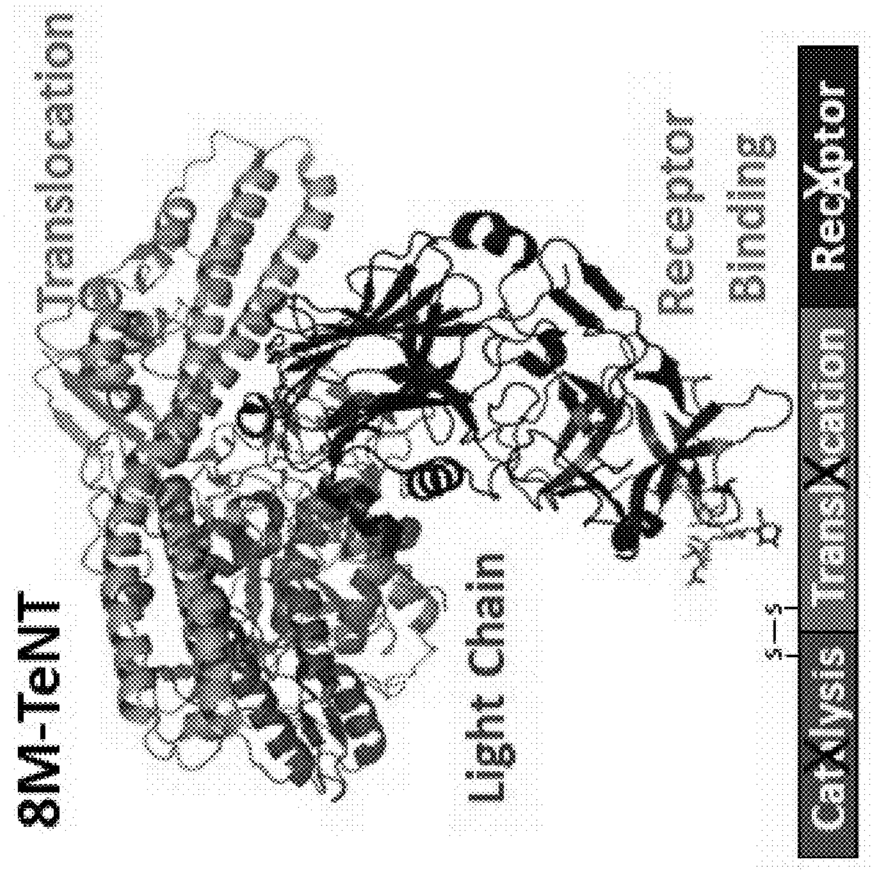
FIG. 15 is a crystal structure of TeNTRY PDB:5n0b. Four TT functions were inactivated: Light Chain E234Q, R373A, Y376F (Zn$^{++}$ binding), L231K (VAMP-2 cleavage) and Y26A (VAMP-2 binding), K768A (LC translocation), and R1226L and W1289A (receptor binding).

Organized like BT, Tetanus toxin (TT) is an AB toxin that comprises an N-terminal domain (catalytic Light Chain, LC) and a C-terminal domain (translocation and receptor binding Heavy Chain, HC). Mutation of two amino acids within the $Zn^{++}$ binding pocket of TT(R372A,Y375F) yielded 2M-TT that inhibited $Zn^{++}$ binding and reduced toxicity by 125, 000-fold relative to native tetanus toxin. The 2M-TT amino acid sequence is set forth as SEQ ID NO:2, with the nucleotide sequence set forth as SEQ ID NO:3. In preliminary experiments to further reduce toxicity, an additional mutation to extend the inhibition of $Zn^{++}$ binding (E234Q) was added based upon E234 stabilizing H233, which directly coordinates $Zn^{++}$ binding. Next, neuron binding to dual ganglioside receptor binding was inhibited by engineering two independent mutations (R1226L, W1289A), producing 5M-TT (see Table 7). As a proof of principle, we engineered 6M-TT with an additional mutation to inhibit LC translocation (K768A) (FIG. 14). 6M-TT contains mutations in each of the tetanus toxin functions: catalysis, translocation, and receptor binding. 6M-TT was purified from *E. coli* at 6 mg/liter of batch culture. Four mice each injected with 20 μg of single chain or di-chain 6M-TT did not show any symptoms of tetanus. Thus, 6M-TT is a soluble, well-expressed, and non-toxic protein.

TABLE 7

| Exemplary point mutations for 8M-TT | | | | |
|---|---|---|---|---|
| | Zn++ binding | Substrate Binding & catalysis | Light Chain translocation | Ganglioside receptor binding |
| | E234Q, R372A, Y375F (TT(R372A, Y375F. 2M-TT) is 125,000-fold less toxic than native TT [42] | Y26A, L231K | K768A Inhibits LC translocation (preliminary data) | R1226L, W1289A This mutation is ~800-fold less toxic than TT WT |
| 2MTT | R372A, Y375F | | | |
| 5M-TT | E234Q, R372A, Y375F | | | R1226L, W1289A |
| 6M-TT | E234Q, R372A, Y375F | | K768A (or D767A or E769A) | R1226L, W1289A |
| 7M-TT | E234Q, R372A, Y375F | L231K | K768A (or D767A or E769A) | R1226L, W1289A |
| 8M-TT | E234Q, R372A, Y375F | Y26A, L231K | K768A (or D767A or E769A) | R1226L, W1289A |

6M-TT will be further engineered to, sequentially, inhibit binding and cleavage of VAMP-2 by introducing mutations at positions Y26 and L231 mutations, producing 7M-TT and 8M-TT L231 was chosen based upon earlier studies that showed this mutation reduced the kcat without affecting VAMP-2 affinity and since the L231K mutation did not affect the overall structure of the LC[9]. Y26 was chosen based upon location within the S7 pocket of HCR/T and evidence that the Y26A mutation reduced the LC/T affinity for VAMP-2[9] (see Table 7). 8M-TT and the intermediate products (6M-TT, and 7M-TT) will be subjected to circular dichroism to measure secondary structure, trypsin sensitivity to measure overall protein stability, and mass spectrometry to measure protein composition [42]

Since we now know that 6M-TT is produced as a soluble protein, is highly expressed, and a 20 μg injection is nontoxic in mice, toxicity of 6M-TT, 7M-TT, and 8M-TT will first be assessed in human neuronal cell-based assays, analyzing VAMP-2 cleavage after cell entry as well as VAMP-2 cleavage in cell lysates [64]. If no cleavage or cytotoxicity is detected, absence of in vivo toxicity will be established in the mouse model, using outbred female ICR mice (18 to 22 g, 5 mice/group) (Table 8).

TABLE 8

Residual Toxicity of 8M-TT

| IP injection of 8M-TT (μg) | +3 → +14 day-post Injection |
|---|---|
| 0 | Score for survival |
| 20 | Observe pathology |
| 50 | Weight loss |
| 250 | Signs of stress |
| 1000 | Major organ damage |
| | Tetanus symptoms |

Initial experiments will inject mice intraperitoneally with 20, 50, 250, or 1000 μg of 8M-TT per mouse (by weight 1000 μg equals ~$4\times10^7$ $LD_{50}$ of wild-type tetanus toxin)[65]. Injected mice will be scored for survival for 3 days in the mouse bioassay and observed for up to 14 days for any symptoms indicating TT pathology including, no weight gain, signs of stress, organ damage, and tetanus symptoms. Male mice will be tested for gender disparities.

Outbred female ICR mice (8/ group) will be immunized with 0.01-0.1 μg of optimized M-TT or equivalent amounts of chemically inactivated tetanus toxoid, followed on day 14 with a boost vaccination (Table 9). On day 26, mice are bled and on day 30 mice are challenged with $10^3$-$10^6$ U of tetanus toxin. To investigate long term protection, vaccinated mice will be maintained for 180 days and challenged with TT to test for the duration of immune response. Mice surviving 3 days are scored protected. Serum obtained prior to challenge will be tested for anti-TT by ELISA as previously described [6] and for neutralizing potency against tetanus toxin intoxication of cultured neurons, as an inhibition of VAMP-2 cleavage [71-72]. Male mice will be tested to confirm no gender disparities.

TABLE 9

Potency of a protective optimized M-TT vaccine[A]

| | Days post primary immunization | | |
|---|---|---|---|
| Vaccine (μg) | 14 | 26 & 176 | 30 & 180 |
| Alhydrogel alone<br>8M-TT (0.01-0.1 μg)<br>Chemically inactivated TT (0.01-0.1 μg) | Boost Vaccination | Collect blood | Challenge with $10^3$-$10^6$ U TT |

[A]Mice are vaccinated IP with two doses of M-TT primary (day 0) and boost (day 14)., At day 22 and 176, mice are bleed (Ig titers to TT), challenged with $10^3$-$10^6$ U TT on day 26 and 180, and scored for survival for 3 days.

We expect that each independent LC point mutation introduced will have a multiplicative decrease on the catalytic activity and have reflective reductions in M-TT toxic potency, since the LC mutations inhibit independent steps in catalysis. We do not anticipate that these LC or HC mutations will affect protein stability or immunogenicity, based upon earlier studies on their effect as individual mutations in LC-TT or HC-TT. The injection of 1000 μg of 8M-TT is unlikely to be toxic in our mouse model and 8M-TT will likely have a more neutralizing immune response relative to chemically-inactivated TT, allowing low dose immunization with 8M-TT.

A recent review estimated only a fraction of the potential immunization potency of current conjugate vaccines has been achieved[4]. Studies of microbial pathogens continue to identify additional immunogens that require conjugation to protein toxoids to produce effective T-cell dependent immune responses. These include, but are not limited to, capsules of the meningococcus, [15] fungi, [16], and the pneumococcus [17-18]. In addition, synthetic glycans provide a promising future alternative to natural polysaccharides-based vaccines, which vary in purity and content [20-22.] Tetanus toxoid is an immunogenic carrier protein [23], for polysaccharides. Tetanus toxin is among the best candidates to develop these next generation recombinant conjugate vaccines based upon our knowledge of TT structure-function properties and baseline information of tetanus toxin as a chemically inactivated toxoid, and the continued global need for tetanus vaccination. The production of a safe, easy-to-produce, and protective recombinant TT vaccine, for the first time, enables analysis of recombinant, full length atoxic (non-toxic) TT as a conjugate vaccine carrier. There currently is a lack of knowledge on the protective properties of conjugate vaccine carriers, including tetanus toxoid [73]. The recombinant atoxic M-TT can be used a carrier of several commonly used antigens to measure the enhanced immune response to the antigens when conjugated to M-TT versus chemically inactivated TT.

The protocol for conjugating oligosaccharides to M-TT follow published protocols of the Lees laboratory [74]. Briefly, polysaccharides (PS) are reduced to a molecular weight of 100-300 kDa using an LV-1 microfluidizer. PS are prepared at 5 mg/ml in water and activated with 1-cyano-4-dimethylamino-pyridinium tetrafluoroborate (CDAP, 0.5 mg/mg) [74]. An equal weight of protein (5 mg/ml) is added and the solution maintained at pH 9. The reaction is monitored by size exclusion chromatography (SEC) HPLC and quenched with excess glycine. Conjugates are purified by SEC and molecular weight determined by SEC-Multi-Angle Light Scattering. Authenticated polysaccharides and peptides will be crosslinked to 8M-TT: (i) Group B streptococcus (GBS) polysaccharide serotypes Ia, Ib, II, III, IV and IV; (2) Poly-β-(1-6)-N-acetyl-glucosamine (PNAG) which mediates biofilm formation as a candidate broad spectrum vaccine for *Klebsiella pneumoniae, Enterobacter cloacae, Stenotrophomonas maltophilia*, and the *Burkholderia cepacia* complex (BCC)[45]; (3) Peptides currently being tested in flu vaccines.

Outbred female ICR mice (8/ group) will be immunized with 0.01-0.1 μg of conjugated-optimized M-TT or equivalent amounts of chemically inactivated tetanus toxoid, followed on day 14 with a boost vaccination (Table 10). On day 26 mice are bled, and on day 30 mice are challenged with $10^3$-$10^6$ U of tetanus toxin. To investigate long term protection, vaccinated mice will be maintained for 180 days and challenged with TT to test for the duration of immune response. Mice surviving 3 days are scored protected. Serum obtained prior to challenge will be tested for anti-conjugate and anti-TT by ELISA as previously described [6 74]. Male mice will be tested for gender disparities.

TABLE 10

Potency of a protective conjugate 8M-TT vaccine [A]

| | Day post primary immunization | | |
|---|---|---|---|
| Vaccine (μg) | 14 | 26 or 176 | 30 or 180 |
| Conjugated-8M-TT (0.01 or 0.1 μg)<br>Conjugated-chemically inactivated TT (0.01 or 0.1 μg) | Boost Vaccination | Collect blood Assess α-conjugate and α-8M- | Challenge with $10^3$-$10^6$ U TT |

TABLE 10-continued

Potency of a protective conjugate 8M-TT vaccine [A]

| Vaccine (μg) | Day post primary immunization 14 | 26 or 176 | 30 or 180 |
|---|---|---|---|
| Equivalent conjugate antigen, alone | | TT IgM and IgG titers | |
| Alum (control) | | | |

[A] Mice are vaccinated IP with conjugate-M-TT (primary and boost). At day 21, mice are bleed (Ig titers) and challenged with $10^3$ or $10^6$ U TT on day 30. Mice are challenged with $10^3$ or $10^6$ U BT/A and scored for survival for 3 days. In a separate experiment, vaccinated mice are held and on day 176 bled to measure Ig titers, T Helper Cells and B Memory and then challenged with native TT.

The PNAG oligosaccharide, GBS polysaccharide, and flu peptides will be individually conjugated to 8M-TT vaccine. Subsequent experiments will combine GBS and PNAG to produce a multiplex polysaccharide conjugate-8M-TT vaccine. Next, the flu peptides and PNAG will be combined to make a multiplex-peptide-polysaccharide conjugate-8M-TT vaccine. These experiments will test the potential of 8M-TT as a vaccine carrier.

It is expected that individual conjugated vaccines, PNAG-8M-TT, GBS-8M-TT, and peptide-8M-TT, will elicit similar immune response to the conjugate and stronger immune response to TT relative to the respective conjugate-chemically inactivated TT vaccine. We also anticipate that the immune response to polysaccharides and peptide within the 8M-TT vaccine will elicit a similar immune response relative to when the individual antigens are conjugated to 8M-TT. We anticipate the immune response to 8M-TT will correlate with protection to native TT challenge.

REFERENCES

1. Rappuoli, R., The vaccine containing recombinant pertussis toxin induces early and long-lasting protection. *Biologicals* 1999, 27 (2), 99-102.
2. Agnolon, V.; Bruno, C.; Leuzzi, R.; Galletti, B.; D'Oro, U.; Pizza, M.; Seubert, A.; O'Hagan, D. T.; Baudner, B. C., The potential of adjuvants to improve immune responses against TdaP vaccines: A preclinical evaluation of MF59 and monophosphoryl lipid A. *Int J Pharm* 2015, 492 (1-2), 169-76.
3. Nabel, G. J., Designing tomorrow's vaccines. *N Engl J Med* 2013, 368 (6), 551-60.
4. Rappuoli, R., Glycoconjugate vaccines: Principles and mechanisms. *Sci Transl Med* 2018, 10 (456).
5. Drake, J. W.; Charlesworth, B.; Charlesworth, D.; Crow, J. F., Rates of spontaneous mutation. *Genetics* 1998, 148 (4), 1667-86.
6. Przedpelski, A.; Tepp, W. H.; Zuverink, M.; Johnson, E. A.; Pellet, S.; Barbieri, J. T., Enhancing toxin-based vaccines against botulism. *Vaccine* 2018.
7. Chen, S.; Kim, J. J.; Barbieri, J. T., Mechanism of substrate recognition by *botulinum* neurotoxin serotype A. *J Biol Chem* 2007, 282 (13), 9621-7.
8. Weisemann, J.; Stern, D.; Mahrhold, S.; Dorner, B. G.; Rummel, A., *Botulinum* Neurotoxin Serotype A Recognizes Its Protein Receptor SV2 by a Different Mechanism than *Botulinum* Neurotoxin B Synaptotagmin. *Toxins* (*Basel*) 2016, 8 (5).
9. Chen, S.; Karalewitz, A. P.; Barbieri, J. T., Insights into the different catalytic activities of *Clostridium* neurotoxins. *Biochemistry* 2012, 51 (18), 3941-7.
10. Chen, C.; Fu, Z.; Kim, J. J.; Barbieri, J. T.; Baldwin, M. R., Gangliosides as high affinity receptors for tetanus neurotoxin. *J Biol Chem* 2009, 284 (39), 26569-77.
11. Centers for Disease, C.; Prevention, Impact of vaccines universally recommended for children—United States, 1990-1998. *MMWR Morb Mortal Wkly Rep* 1999, 48 (12), 243-8.
12. Rappuoli, R.; Podda, A.; Pizza, M.; Covacci, A.; Bartoloni, A.; de Magistris, M. T.; Nencioni, L., Progress towards the development of new vaccines against whooping cough. *Vaccine* 1992, 10 (14), 1027-32.
13. Centers for Disease, C.; Prevention, Thimerosal in vaccines: a joint statement of the American Academy of Pediatrics and the Public Health Service. *MMWR Morb Mortal Wkly Rep* 1999, 48 (26), 563-5.
14. Van Nuffel, A. M.; Benteyn, D.; Wilgenhof, S.; Corthals, J.; Heirman, C.; Neyns, B.; Thielemans, K.; Bonehill, A., Intravenous and intradermal TriMix-dendritic cell therapy results in a broad T-cell response and durable tumor response in a chemorefractory stage IV-Mlc melanoma patient. *Cancer Immunol Immunother* 2012, 61 (7), 1033-43.
15. Wang, N. Y.; Pollard, A. J., The next chapter for group B meningococcal vaccines. *Crit Rev Microbiol* 2017, 1-17.
16. Specht, C. A.; Lee, C. K.; Huang, H.; Tipper, D. J.; Shen, Z. T.; Lodge, J. K.; Leszyk, J.; Ostroff, G. R.; Levitz, S. M., Protection against Experimental Cryptococcosis following Vaccination with Glucan Particles Containing Cryptococcus Alkaline Extracts. *MBio* 2015, 6 (6), e01905-15.
17. Feikin, D. R.; Elie, C. M.; Goetz, M. B.; Lennox, J. L.; Carlone, G. M.; Romero-Steiner, S.; Holder, P. F.; O'Brien, W. A.; Whitney, C. G.; Butler, J. C.; Breiman, R. F., Randomized trial of the quantitative and functional antibody responses to a 7-valent pneumococcal conjugate vaccine and/or 23-valent polysaccharide vaccine among HIV-infected adults. *Vaccine* 2001, 20 (3-4), 545-53.
18. Wang, Y.; Li, J.; Wang, Y.; Gu, W.; Zhu, F., Effectiveness and practical uses of 23-valent pneumococcal polysaccharide vaccine in healthy and special populations. *Hum Vaccin Immunother* 2017, 1-10.
19. Kumai, T.; Lee, S.; Cho, H. I.; Sultan, H.; Kobayashi, H.; Harabuchi, Y.; Celis, E., Optimization of Peptide Vaccines to Induce Robust Antitumor CD4 T-cell Responses. *Cancer Immunol Res* 2017, 5 (1), 72-83.
20. Travassos, L. R.; Taborda, C. P., Linear Epitopes of Paracoccidioides brasiliensis and Other Fungal Agents of Human Systemic Mycoses As Vaccine Candidates. *Front Immunol* 2017, 8, 224.
21. Ye, X., Synthetic Glycans and Glycomimetics: A Promising Alternative to Natural Polysaccharides. *Chemistry* 2017.
22. Guazzelli, L.; McCabe, O.; Oscarson, S., Synthesis of part structures of Cryptococcus neoformans serotype C capsular polysaccharide. *Carbohydr Res* 2016, 433, 5-13.
23. Perry, C. M., Meningococcal groups C and Y and haemophilus B tetanus toxoid conjugate vaccine (Hib-MenCY-TT; MenHibrix((R))): a review. *Drugs* 2013, 73 (7), 703-13.
24. Killeen, K. P.; Escuyer, V.; Mekalanos, J. J.; Collier, R. J., Reversion of recombinant toxoids: mutations in diphtheria toxin that partially compensate for active-site deletions. *Proc Natl Acad Sci USA* 1992, 89 (13), 6207-9.
25. Dressler, D., *Botulinum* toxin drugs: brief history and outlook. *J. Neural Transm* (*Vienna*) 2016, 123 (3), 277-9.
26. Centers for Disease, C.; Prevention, Notice of CDC's discontinuation of investigational pentavalent (ABCDE) *botulinum* toxoid vaccine for workers at risk for occupational exposure to *botulinum* toxins. *MMWR Morb Mortal Wkly Rep* 2011, 60 (42), 1454-5.

27. Koepke, R.; Sobel, J.; Arnon, S. S., Global occurrence of infant botulism, 1976-2006. *Pediatrics* 2008, 122 (1), e73-82.
28. Schwarz, P. J.; Arnon, S. S., Botulism immune globulin for infant botulism arrives—one year and a Gulf War later. *West J Med* 1992, 156 (2), 197-8.
29. Payne, J. R.; Khouri, J. M.; Jewell, N. P.; Arnon, S. S., Efficacy of Human Botulism Immune Globulin for the Treatment of Infant Botulism: The First 12 Years Post Licensure. *J Pediatr* 2017.
30. Sundeen, G.; Barbieri, J. T., Vaccines against Botulism. *Toxins* (*Basel*) 2017, 9 (9).
31. Smith, L. A., Botulism and vaccines for its prevention. *Vaccine* 2009, 27 *Suppl* 4, D33-9.
32. Fan, Y.; Garcia-Rodriguez, C.; Lou, J.; Wen, W.; Conrad, F.; Zhai, W.; Smith, T. J.; Smith, L. A.; Marks, J. D., A three monoclonal antibody combination potently neutralizes multiple *botulinum* neurotoxin serotype F subtypes. *PLoS One* 2017, 12 (3), e0174187.
33. Lou, J.; Geren, I.; Garcia-Rodriguez, C.; Forsyth, C. M.; Wen, W.; Knopp, K.; Brown, J.; Smith, T.; Smith, L. A.; Marks, J. D., Affinity maturation of human *botulinum* neurotoxin antibodies by light chain shuffling via yeast mating. *Protein Eng Des Sel* 2010, 23 (4), 311-9.
34. Lou, J.; Wen, W.; Conrad, F.; Meng, Q.; Dong, J.; Sun, Z.; Garcia-Rodriguez, C.; Farr-Jones, S.; Cheng, L. W.; Henderson, T. D.; Brown, J. L.; Smith, T. J.; Smith, L. A.; Cormier, A.; Marks, J. D., A Single Tri-Epitopic Antibody Virtually Recapitulates the Potency of a Combination of Three Monoclonal Antibodies in Neutralization of *Botulinum* Neurotoxin Serotype A. *Toxins* (*Basel*) 2018, 10 (2).
35. Webb, R. P.; Smith, T. J.; Smith, L. A.; Wright, P. M.; Guernieri, R. L.; Brown, J. L.; Skerry, J. C., Recombinant *Botulinum* Neurotoxin Hc Subunit (BoNT Hc) and Catalytically Inactive *Clostridium botulinum* Holoproteins (ciBoNT HPs) as Vaccine Candidates for the Prevention of Botulism. *Toxins* (*Basel*) 2017, 9 (9).
36. Cohn, A. C.; MacNeil, J. R.; Harrison, L. H.; Lynfield, R.; Reingold, A.; Schaffner, W.; Zell, E. R.; Plikaytis, B.; Wang, X.; Messonnier, N. E.; Active Bacterial Core Surveillance, T.; MeningNet Surveillance, P., Effectiveness and Duration of Protection of One Dose of a Meningococcal Conjugate Vaccine. *Pediatrics* 2017, 139 (2).
37. Isturiz, R. E.; Hall-Murray, C.; McLaughlin, J. M.; Snow, V.; Schmoele-Thoma, B.; Webber, C.; Thompson, A.; Scott, D. A., Pneumococcal conjugate vaccine use for the prevention of pneumococcal disease in adults <50 years of age. *Expert Rev Vaccines* 2017, 1-11.
38. Tetanus vaccines: WHO position paper—February 2017. *Wkly Epidemiol Rec* 2017, 92 (6), 53-76.
39. Woldeamanuel, Y. W., Tetanus in Ethiopia: unveiling the blight of an entirely vaccine-preventable disease. *Curr Neurol Neurosci Rep* 2012, 12 (6), 655-65.
40. World Health Organization. Electronic address, s. w. i., Tetanus vaccines: WHO position paper, February 2017—Recommendations. *Vaccine* 2018, 36 (25), 3573-3575.
41. Blum, F. C.; Tepp, W. H.; Johnson, E. A.; Barbieri, J. T., Multiple domains of tetanus toxin direct entry into primary neurons. *Traffic* 2014, 15 (10), 1057-65.
42. Blum, F. C.; Przedpelski, A.; Tepp, W. H.; Johnson, E. A.; Barbieri, J. T., Entry of a recombinant, full-length, atoxic tetanus neurotoxin into Neuro-2a cells. *Infect Immun* 2014, 82 (2), 873-81.
43. Masuyer, G.; Conrad, J.; Stenmark, P., The structure of the tetanus toxin reveals pH-mediated domain dynamics. *EMBO Rep* 2017, 18 (8), 1306-1317.
44. Klein, N. P.; Abu-Elyazeed, R.; Baine, Y.; Cheuvart, B.; Silerova, M.; Mesaros, N., Immunogenicity and safety of the Haemophilus influenzae type b and Neisseria meningitidis serogroups C and Y-tetanus toxoid conjugate vaccine co-administered with human rotavirus, hepatitis A and 13-valent pneumococcal conjugate vaccines: results from a phase III, randomized, multicenter study in infants. *Hum Vaccin Immunother* 2018, 1-12.
45. Skurnik, D.; Cywes-Bentley, C.; Pier, G. B., The exceptionally broad-based potential of active and passive vaccination targeting the conserved microbial surface polysaccharide PNAG. *Expert Rev Vaccines* 2016, 15 (8), 1041-53.
46. McGuirk, P.; Mills, K. H., Pathogen-specific regulatory T cells provoke a shift in the Th1/Th2 paradigm in immunity to infectious diseases. *Trends Immunol* 2002, 23 (9), 450-5.
47. Moyron-Quiroz, J. E.; McCausland, M. M.; Kageyama, R.; Sette, A.; Crotty, S., The smallpox vaccine induces an early neutralizing IgM response. *Vaccine* 2009, 28 (1), 140-7.
48. Mayer, S.; Laumer, M.; Mackensen, A.; Andreesen, R.; Krause, S. W., Analysis of the immune response against tetanus toxoid: enumeration of specific T helper cells by the Elispot assay. *Immunobiology* 2002, 205 (3), 282-9.
49. Oshima, M.; Hayakari, M.; Middlebrook, J. L.; Atassi, M. Z., Immune recognition of *botulinum* neurotoxin type A: regions recognized by T cells and antibodies against the protective H(C) fragment (residues 855-1296) of the toxin. *Mol Immunol* 1997, 34 (14), 1031-40.
50. Dolimbek, G. S.; Dolimbek, B. Z.; Aoki, K. R.; Atassi, M. Z., Mapping of the antibody and T cell recognition profiles of the HN domain (residues 449-859) of the heavy chain of *botulinum* neurotoxin A in two high-responder mouse strains. *Immunol Invest* 2005, 34 (2), 119-42.
51. Clayton, M. A.; Clayton, J. M.; Brown, D. R.; Middlebrook, J. L., Protective vaccination with a recombinant fragment of *Clostridium botulinum* neurotoxin serotype A expressed from a synthetic gene in *Escherichia coli. Infect Immun* 1995, 63 (7), 2738-42.
52. Nencioni, L.; Volpini, G.; Peppoloni, S.; Bugnoli, M.; De Magistris, T.; Marsili, I.; Rappuoli, R., Properties of pertussis toxin mutant PT-9K/129G after formaldehyde treatment. *Infect Immun* 1991, 59 (2), 625-30.
53. Zuverink, M.; Chen, C.; Przedpelski, A.; Blum, F. C.; Barbieri, J. T., A Heterologous Reporter Defines the Role of the Tetanus Toxin Interchain Disulfide in Light-Chain Translocation. *Infect Immun* 2015, 83 (7), 2714-24.
54. Johnson, B. D.; Becker, E. E.; Truitt, R. L., Graft-vs.-host and graft-vs.-leukemia reactions after delayed infusions of donor T-subsets. *Biol Blood Marrow Transplant* 1999, 5 (3), 123-32.
55. Keller, J. E., Characterization of new formalin-detoxified *botulinum* neurotoxin toxoids. *Clin Vaccine Immunol* 2008, 15 (9), 1374-9.
56. Sikorra, S.; Henke, T.; Galli, T.; Binz, T., Substrate recognition mechanism of VAMP/synaptobrevin-cleaving clostridial neurotoxins. *J Biol Chem* 2008, 283 (30), 21145-52.
57. Chen, S.; Barbieri, J. T., Multiple pocket recognition of SNAP25 by *botulinum* neurotoxin serotype E. *J Biol Chem* 2007, 282 (35), 25540-7.

58. Lacy, D. B.; Stevens, R. C., Sequence homology and structural analysis of the clostridial neurotoxins. *Journal of molecular biology* 1999, 291 (5), 1091-104.
59. Rummel, A.; Hafner, K.; Mahrhold, S.; Darashchonak, N.; Holt, M.; Jahn, R.; Beermann, S.; Karnath, T.; Bigalke, H.; Binz, T., *Botulinum* neurotoxins C, E and F bind gangliosides via a conserved binding site prior to stimulation-dependent uptake with *botulinum* neurotoxin F utilising the three isoforms of SV2 as second receptor. *J Neurochem* 2009, 110 (6), 1942-54.
60. Agarwal, R.; Binz, T.; Swaminathan, S., Structural analysis of *botulinum* neurotoxin serotype F light chain: implications on substrate binding and inhibitor design. *Biochemistry* 2005, 44 (35), 11758-65.
61. Berntsson, R. P.; Peng, L.; Dong, M.; Stenmark, P., Structure of dual receptor binding to *botulinum* neurotoxin B. *Nat Commun* 2013, 4, 2058.
62. Fu, Z.; Chen, C.; Barbieri, J. T.; Kim, J. J.; Baldwin, M. R., Glycosylated SV2 and gangliosides as dual receptors for *botulinum* neurotoxin serotype F. *Biochemistry* 2009, 48 (24), 5631-41.
63. Strotmeier, J.; Mahrhold, S.; Krez, N.; Janzen, C.; Lou, J.; Marks, J. D.; Binz, T.; Rummel, A., Identification of the synaptic vesicle glycoprotein 2 receptor binding site in *botulinum* neurotoxin A. *FEBS Lett* 2014, 588 (7), 1087-93.
64. Pellett, S.; Tepp, W. H.; Lin, G.; Johnson, E. A., Substrate cleavage and duration of action of *botulinum* neurotoxin type FA ("H, HA"). *Toxicon* 2017.
65. Gill, D. M., Bacterial toxins: a table of lethal amounts. *Microbiol Rev* 1982, 46 (1), 86-94.
66. Halperin, B. A.; Morris, A.; Mackinnon-Cameron, D.; Mutch, J.; Langley, J. M.; McNeil, S. A.; Macdougall, D.; Halperin, S. A., Kinetics of the antibody response to tetanus-diphtheria-acellular pertussis vaccine in women of childbearing age and postpartum women. *Clin Infect Dis* 2011, 53 (9), 885-92.
67. Halliwell, G., The action of proteolytic enzymes on *Clostridium botulinum* type A toxin. *Biochem J* 1954, 58 (1), 4-8.
68. Schmidt, J. J.; Sathyamoorthy, V.; DasGupta, B. R., Partial amino acid sequence of the heavy and light chains of *botulinum* neurotoxin type A. *Biochem Biophys Res Commun* 1984, 119 (3), 900-4.
69. Rao, K. N.; Kumaran, D.; Binz, T.; Swaminathan, S., Structural analysis of the catalytic domain of tetanus neurotoxin. *Toxicon* 2005, 45 (7), 929-39.
70. Chen, C.; Fu, Z.; Kim, J. J.; Barbieri, J. T.; Baldwin, M. R., Gangliosides as high affinity receptors for tetanus neurotoxin. *The Journal of biological chemistry* 2009, 284 (39), 26569-77.
71. Pellett, S.; Tepp, W. H.; Lin, G.; Johnson, E. A., Substrate cleavage and duration of action of *botulinum* neurotoxin type FA ("H, HA"). *Toxicon* 2018, 147, 38-46.
72. Pellett, S.; Tepp, W. H.; Johnson, E. A.; Sesardic, D., Assessment of ELISA as endpoint in neuronal cell-based assay for BoNT detection using hiPSC derived neurons. *J Pharmacol Toxicol Methods* 2017, 88 (Pt 1), 1-6.
73. Broker, M.; Berti, F.; Schneider, J.; Vojtek, I., Polysaccharide conjugate vaccine protein carriers as a "neglected valency"—Potential and limitations. *Vaccine* 2017, 35 (25), 3286-3294.
74. Lees, A.; Nelson, B. L.; Mond, J. J., Activation of soluble polysaccharides with 1-cyano-4-dimethylaminopyridinium tetrafluoroborate for use in protein-polysaccharide conjugate vaccines and immunological reagents. *Vaccine* 1996, 14 (3), 190-8.

It should be noted that the above description, attached figures and their descriptions are intended to be illustrative and not limiting of this invention. Many themes and variations of this invention will be suggested to one skilled in this and, in light of the disclosure. All such themes and variations are within the contemplation hereof. For instance, while this invention has been described in conjunction with the various exemplary embodiments outlined above, various alternatives, modifications, variations, improvements, and/or substantial equivalents, whether known or that rare or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/or substantial equivalents of these exemplary embodiments.

We claim:

1. A modified tetanus toxin polypeptide comprising the mutations R372A, Y375F, K768A, E234Q, R1226L, and W1289A, wherein each position is numbered relative to SEQ ID NO:1, the polypeptide having reduced toxicity and receptor binding compared with the toxicity and receptor binding of SEQ ID NO:1.

2. The modified polypeptide of claim 1, wherein the mutations comprise R372A, Y375F, E234Q, D767A, E769A, K768A, R1226L, and W1289A.

3. The modified polypeptide of claim 2, wherein the modified polypeptide comprises SEQ ID NO:5.

4. The modified polypeptide of claim 1, further comprising a mutation at one or both of positions L230 and Y26, wherein each position is numbered relative to SEQ ID NO:1.

5. The modified polypeptide of claim 4, wherein the mutations at one or both of positions L230 and Y26 comprise L230K and Y26A.

6. (Previously Presented The modified polypeptide of claim 4, wherein the modified polypeptide comprises SEQ ID NO:6 or SEQ ID NO:7.

7. The modified polypeptide of claim 1, further comprising a covalently linked carbohydrate or peptide, whereby the polypeptide is a polypeptide-carbohydrate conjugate or a polypeptide-peptide conjugate.

8. A composition comprising a modified polypeptide according to claim 1 and a pharmaceutically acceptable carrier.

9. A method of reducing the risk of a subject developing tetanus by inducing an immune response through administering to the subject a therapeutically effective amount of a modified polypeptide according to claim 1.

* * * * *

SEQUENCE LISTING

```
<160> NUMBER OF SEQ ID NOS: 7

<210> SEQ ID NO 1
<211> LENGTH: 1315
<212> TYPE: PRT
<213> ORGANISM: Clostridium tetani

<400> SEQUENCE: 1

Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
            20                  25                  30

Tyr Tyr Lys Ala Phe Lys Ile Thr Asp Arg Ile Trp Ile Val Pro Glu
        35                  40                  45

Arg Tyr Glu Phe Gly Thr Lys Pro Glu Asp Phe Asn Pro Pro Ser Ser
    50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
```

-continued

```
                85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
        195                 200                 205

Val Ile Glu Asn Ile Thr Ser Leu Thr Ile Gly Lys Ser Lys Tyr Phe
    210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
    290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
            340                 345                 350

Ser Ile Met Tyr Gly Phe Thr Glu Ile Glu Leu Gly Lys Lys Phe Asn
        355                 360                 365

Ile Lys Thr Arg Leu Ser Tyr Phe Ser Met Asn His Asp Pro Val Lys
    370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
        435                 440                 445

Arg Glu Asn Leu Tyr Asn Arg Thr Ala Ser Leu Thr Asp Leu Gly Gly
    450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
            500                 505                 510
```

-continued

```
Ile Val Asp Tyr Asn Leu Gln Ser Lys Ile Thr Leu Pro Asn Asp Arg
        515                 520                 525

Thr Thr Pro Val Thr Lys Gly Ile Pro Tyr Ala Pro Glu Tyr Lys Ser
    530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
        595                 600                 605

Gly Ile Leu Phe Leu Gln Trp Val Arg Asp Ile Ile Asp Asp Phe Thr
    610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
            660                 665                 670

Leu Leu Glu Tyr Ile Pro Glu Ile Thr Leu Pro Val Ile Ala Ala Leu
        675                 680                 685

Ser Ile Ala Glu Ser Ser Thr Gln Lys Glu Lys Ile Ile Lys Thr Ile
    690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
            740                 745                 750

Lys Lys Ile Ile Asp Tyr Glu Tyr Lys Ile Tyr Ser Gly Pro Asp Lys
        755                 760                 765

Glu Gln Ile Ala Asp Glu Ile Asn Asn Leu Lys Asn Lys Leu Glu Glu
    770                 775                 780

Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
                805                 810                 815

Leu Leu Glu Phe Asp Thr Gln Ser Lys Asn Ile Leu Met Gln Tyr Ile
            820                 825                 830

Lys Ala Asn Ser Lys Phe Ile Gly Ile Thr Glu Leu Lys Lys Leu Glu
        835                 840                 845

Ser Lys Ile Asn Lys Val Phe Ser Thr Pro Ile Pro Phe Ser Tyr Ser
    850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                885                 890                 895

Ser Asp Ile Ser Gly Phe Asn Ser Ser Val Ile Thr Tyr Pro Asp Ala
            900                 905                 910

Gln Leu Val Pro Gly Ile Asn Gly Lys Ala Ile His Leu Val Asn Asn
        915                 920                 925
```

-continued

```
Glu Ser Ser Glu Val Ile Val His Lys Ala Met Asp Ile Glu Tyr Asn
    930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
                965                 970                 975

Ile Ser Ser Met Lys Lys His Ser Leu Ser Ile Gly Ser Gly Trp Ser
            980                 985                 990

Val Ser Leu Lys Gly Asn Asn Leu  Ile Trp Thr Leu Lys  Asp Ser Ala
        995                 1000                 1005

Gly Glu  Val Arg Gln Ile Thr  Phe Arg Asp Leu Pro  Asp Lys Phe
    1010                 1015                 1020

Asn Ala  Tyr Leu Ala Asn Lys  Trp Val Phe Ile Thr  Ile Thr Asn
    1025                 1030                 1035

Asp Arg  Leu Ser Ser Ala Asn  Leu Tyr Ile Asn Gly  Val Leu Met
    1040                 1045                 1050

Gly Ser  Ala Glu Ile Thr Gly  Leu Gly Ala Ile Arg  Glu Asp Asn
    1055                 1060                 1065

Asn Ile  Thr Leu Lys Leu Asp  Arg Cys Asn Asn Asn  Asn Gln Tyr
    1070                 1075                 1080

Val Ser  Ile Asp Lys Phe Arg  Ile Phe Cys Lys Ala  Leu Asn Pro
    1085                 1090                 1095

Lys Glu  Ile Glu Lys Leu Tyr  Thr Ser Tyr Leu Ser  Ile Thr Phe
    1100                 1105                 1110

Leu Arg  Asp Phe Trp Gly Asn  Pro Leu Arg Tyr Asp  Thr Glu Tyr
    1115                 1120                 1125

Tyr Leu  Ile Pro Val Ala Ser  Ser Ser Lys Asp Val  Gln Leu Lys
    1130                 1135                 1140

Asn Ile  Thr Asp Tyr Met Tyr  Leu Thr Asn Ala Pro  Ser Tyr Thr
    1145                 1150                 1155

Asn Gly  Lys Leu Asn Ile Tyr  Tyr Arg Arg Leu Tyr  Asn Gly Leu
    1160                 1165                 1170

Lys Phe  Ile Ile Lys Arg Tyr  Thr Pro Asn Asn Glu  Ile Asp Ser
    1175                 1180                 1185

Phe Val  Lys Ser Gly Asp Phe  Ile Lys Leu Tyr Val  Ser Tyr Asn
    1190                 1195                 1200

Asn Asn  Glu His Ile Val Gly  Tyr Pro Lys Asp Gly  Asn Ala Phe
    1205                 1210                 1215

Asn Asn  Leu Asp Arg Ile Leu  Arg Val Gly Tyr Asn  Ala Pro Gly
    1220                 1225                 1230

Ile Pro  Leu Tyr Lys Lys Met  Glu Ala Val Lys Leu  Arg Asp Leu
    1235                 1240                 1245

Lys Thr  Tyr Ser Val Gln Leu  Lys Leu Tyr Asp Asp  Lys Asn Ala
    1250                 1255                 1260

Ser Leu  Gly Leu Val Gly Thr  His Asn Gly Gln Ile  Gly Asn Asp
    1265                 1270                 1275

Pro Asn  Arg Asp Ile Leu Ile  Ala Ser Asn Trp Tyr  Phe Asn His
    1280                 1285                 1290

Leu Lys  Asp Lys Ile Leu Gly  Cys Asp Trp Tyr Phe  Val Pro Thr
    1295                 1300                 1305

Asp Glu  Gly Trp Thr Asn Asp
    1310                 1315
```

<210> SEQ ID NO 2
<211> LENGTH: 1315
<212> TYPE: PRT
<213> ORGANISM: Clostridium tetani

<400> SEQUENCE: 2

```
Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
            20                  25                  30

Tyr Tyr Lys Ala Phe Lys Ile Thr Asp Arg Ile Trp Ile Val Pro Glu
        35                  40                  45

Arg Tyr Glu Phe Gly Thr Lys Pro Glu Asp Phe Asn Pro Pro Ser Ser
    50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
        195                 200                 205

Val Ile Glu Asn Ile Thr Ser Leu Thr Ile Gly Lys Ser Lys Tyr Phe
    210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
    290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
            340                 345                 350

Ser Ile Met Tyr Gly Phe Thr Glu Ile Glu Leu Gly Lys Lys Phe Asn
        355                 360                 365

Ile Lys Thr Ala Leu Ser Phe Phe Ser Met Asn His Asp Pro Val Lys
    370                 375                 380
```

-continued

```
Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
        435                 440                 445

Arg Glu Asn Leu Tyr Asn Arg Thr Ala Ser Leu Thr Asp Leu Gly Gly
    450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
            500                 505                 510

Ile Val Asp Tyr Asn Leu Gln Ser Lys Ile Thr Leu Pro Asn Asp Arg
        515                 520                 525

Thr Thr Pro Val Thr Lys Gly Ile Pro Tyr Ala Pro Glu Tyr Lys Ser
    530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
        595                 600                 605

Gly Ile Leu Phe Leu Gln Trp Val Arg Asp Ile Ile Asp Asp Phe Thr
    610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
            660                 665                 670

Leu Leu Glu Tyr Ile Pro Glu Ile Thr Leu Pro Val Ile Ala Ala Leu
        675                 680                 685

Ser Ile Ala Glu Ser Ser Thr Gln Lys Glu Lys Ile Ile Lys Thr Ile
    690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
            740                 745                 750

Lys Lys Ile Ile Asp Tyr Glu Tyr Lys Ile Tyr Ser Gly Pro Asp Lys
        755                 760                 765

Glu Gln Ile Ala Asp Glu Ile Asn Asn Leu Lys Asn Lys Leu Glu Glu
    770                 775                 780

Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
```

-continued

```
                805                 810                 815

Leu Leu Glu Phe Asp Thr Gln Ser Lys Asn Ile Leu Met Gln Tyr Ile
            820                 825                 830

Lys Ala Asn Ser Lys Phe Ile Gly Ile Thr Glu Leu Lys Lys Leu Glu
        835                 840                 845

Ser Lys Ile Asn Lys Val Phe Ser Thr Pro Ile Pro Phe Ser Tyr Ser
    850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                885                 890                 895

Ser Asp Ile Ser Gly Phe Asn Ser Ser Val Ile Thr Tyr Pro Asp Ala
            900                 905                 910

Gln Leu Val Pro Gly Ile Asn Gly Lys Ala Ile His Leu Val Asn Asn
        915                 920                 925

Glu Ser Ser Glu Val Ile Val His Lys Ala Met Asp Ile Glu Tyr Asn
    930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
                965                 970                 975

Ile Ser Ser Met Lys Lys His Ser Leu Ser Ile Gly Ser Gly Trp Ser
            980                 985                 990

Val Ser Leu Lys Gly Asn Asn Leu  Ile Trp Thr Leu Lys  Asp Ser Ala
        995                 1000                1005

Gly Glu  Val Arg Gln Ile Thr  Phe Arg Asp Leu Pro  Asp Lys Phe
    1010                 1015                1020

Asn Ala  Tyr Leu Ala Asn Lys  Trp Val Phe Ile Thr  Ile Thr Asn
    1025                 1030                1035

Asp Arg  Leu Ser Ser Ala Asn  Leu Tyr Ile Asn Gly  Val Leu Met
    1040                 1045                1050

Gly Ser  Ala Glu Ile Thr Gly  Leu Gly Ala Ile Arg  Glu Asp Asn
    1055                 1060                1065

Asn Ile  Thr Leu Lys Leu Asp  Arg Cys Asn Asn Asn  Asn Gln Tyr
    1070                 1075                1080

Val Ser  Ile Asp Lys Phe Arg  Ile Phe Cys Lys Ala  Leu Asn Pro
    1085                 1090                1095

Lys Glu  Ile Glu Lys Leu Tyr  Thr Ser Tyr Leu Ser  Ile Thr Phe
    1100                 1105                1110

Leu Arg  Asp Phe Trp Gly Asn  Pro Leu Arg Tyr Asp  Thr Glu Tyr
    1115                 1120                1125

Tyr Leu  Ile Pro Val Ala Ser  Ser Ser Lys Asp Val  Gln Leu Lys
    1130                 1135                1140

Asn Ile  Thr Asp Tyr Met Tyr  Leu Thr Asn Ala Pro  Ser Tyr Thr
    1145                 1150                1155

Asn Gly  Lys Leu Asn Ile Tyr  Tyr Arg Arg Leu Tyr  Asn Gly Leu
    1160                 1165                1170

Lys Phe  Ile Ile Lys Arg Tyr  Thr Pro Asn Asn Glu  Ile Asp Ser
    1175                 1180                1185

Phe Val  Lys Ser Gly Asp Phe  Ile Lys Leu Tyr Val  Ser Tyr Asn
    1190                 1195                1200

Asn Asn  Glu His Ile Val Gly  Tyr Pro Lys Asp Gly  Asn Ala Phe
    1205                 1210                1215
```

-continued

```
Asn Asn  Leu Asp Arg Ile Leu  Arg Val Gly Tyr Asn  Ala Pro Gly
    1220                 1225                 1230

Ile Pro  Leu Tyr Lys Lys Met  Glu Ala Val Lys Leu  Arg Asp Leu
    1235                 1240                 1245

Lys Thr  Tyr Ser Val Gln Leu  Lys Leu Tyr Asp Asp  Lys Asn Ala
    1250                 1255                 1260

Ser Leu  Gly Leu Val Gly Thr  His Asn Gly Gln Ile  Gly Asn Asp
    1265                 1270                 1275

Pro Asn  Arg Asp Ile Leu Ile  Ala Ser Asn Trp Tyr  Phe Asn His
    1280                 1285                 1290

Leu Lys  Asp Lys Ile Leu Gly  Cys Asp Trp Tyr Phe  Val Pro Thr
    1295                 1300                 1305

Asp Glu  Gly Trp Thr Asn Asp
    1310                 1315


<210> SEQ ID NO 3
<211> LENGTH: 3945
<212> TYPE: DNA
<213> ORGANISM: Clostridium tetani

<400> SEQUENCE: 3

atgccgatta ccattaacaa ctttcgttat agcgatccgg tgaacaacga taccattatt     60

atgatggaac cgccgtattg caaaggcctg gatatttatt ataaagcgtt taaagttacc    120

gatcgtattt ggattgtgcc ggaacgttat gaatttggca ccaaaccgga agatttcaac    180

ccgccgagca gcctgattga aggcgcgagc gaatattatg atccgaacta tctgcgtacc    240

gatagcgata aagatcgttt cctgcagacc atggtgaaac tgtttaaccg tattaagaac    300

aacgtggcgg gcgaagcgct gctggataaa attattaacg cgattccgta tctgggcaac    360

agctatagcc tgctggataa atttgatacc aacagcaaca gcgtgagctt taacctgctg    420

gaacaagatc cgagcggcgc gaccaccaaa agcgcgatgc tgaccaacct gattattttc    480

ggcccgggcc cggtgctgaa caaaaacgaa gtgcgtggca ttgtgctgcg tgtggataac    540

aagaactatt tcccgtgccg tgatggcttt ggcagcatta tgcagatggc gttttgcccg    600

gaatatgtgc cgacctttga taacgtgatt gaaaacatta ccagcctgac cattggcaaa    660

agcaaatatt tccaagatcc ggcgctgctg ctgatgcatg aactgattca tgtgctgcat    720

ggcctgtatg gcatgcaggt gagcagccat gaaattattc cgagcaaaca ggaaatttat    780

atgcagcata cctatccgat tagcgcggaa gaactgttta cctttggcgg ccaggatgcg    840

aacctgatta gcattgatat taagaacgat ctgtatgaaa agaccctgaa cgattataaa    900

gcgattgcga acaaactgag ccaggtgacc agctgcaacg atccgaacat tgatattgat    960

agctataaac agatttatca gcagaaatat cagtttgata aagatagcaa cggccagtat   1020

attgtgaacg aagataaatt tcagattctg tataacagca ttatgtatgg ctttaccgaa   1080

attgaactgg gcaagaaatt taacattaaa accgcgctga gctttttttag catgaaccat   1140

gatccggtga aaattccgaa cctgctggat gataccattt ataacgatac cgaaggcttt   1200

aacattgaaa gcaaagacct gaaaagcgaa tataaaggcc agaacatgcg tgtgaacacc   1260

aacgcgtttc gtaacgtgga tggatccggc ctggtgagca aactgattgg cctgtgcaag   1320

aagattattc cgccgaccaa cattcgtgag aacctgtata accgtaccgc gagcctgacc   1380

gatctgggcg gcgaactgtg cattaagatt aagaacgaag atctgacctt tattgcggag   1440

aagaacagct ttagcgaaga accgtttcag gatgaaattg tgagctataa caccaagaac   1500
```

-continued

```
aaaccgctga actttaacta tagcctggat aaaattattg tggattataa cctgcagagc   1560
aagattaccc tgccgaacga tcgtaccacc ccggtgacca aaggcattcc gtatgcgccg   1620
gaatataaga gcaacgcggc gagcaccatt gaaattcata acattgatga taacaccatt   1680
tatcagtatc tgtatgcgca gaagagcccg accaccctgc agcgtattac catgaccaac   1740
agcgtggatg atgcgctgat taacagcacc aaaatttata gctattttcc gagcgtgatt   1800
agcaaagtga accagggcgc gcagggcatt ctgtttctgc agtgggtgcg tgatattatt   1860
gatgatttta ccaacgaaag cagccagaaa accaccattg ataaaattag cgatgtgagc   1920
accattgtgc cgtatattgg cccggcgctg aacattgtga aacagggcta tgaaggcaac   1980
tttattggcg cgctggaaac caccggcgtg gtgctgctgc tggaatatat tccggaaatt   2040
accctgccgg tgattgcggc gctgagcatt gcggaaagca gcacccagaa agagaagatt   2100
attaaaacca ttgataactt tctggagaaa cgttatgaga aatggattga agtgtataaa   2160
ctggtgaaag cgaaatggct gggcaccgtg aacacccagt ttcagaaacg tagctatcag   2220
atgtatcgta gcctggaata tcaggtggat gcgattaaga aaattattga ttatgaatat   2280
aagatttata gcggcccgga taaagaacag attgcggatg aaattaacaa cctgaaaaac   2340
aaactggaag agaaagcgaa caaagcgatg attaacatta acatctttat gcgtgaaagc   2400
agccgtagct ttctggtgaa ccagatgatt aacgaagcga agaaacagct gctggaattt   2460
gatacccaga gcaagaacat tctgatgcag tatattaaag cgaacagcaa atttattggc   2520
attaccgaac tgaagaaact ggaaagcaaa attaacaaag tgtttagcac cccgattccg   2580
tttagctata gcaagaacct ggattgctgg gtggataacg aagaagatat tgatgtgatt   2640
ctgaagaaga gcaccattct gaacctggat attaacaacg atattattag cgatattagc   2700
ggcttcaaca gcagcgtgat tacctatccg gatgcgcagc tggtaccggg cattaacggc   2760
aaagcgattc atctggtgaa caacgaaagc agcgaagtga ttgtgcataa agcgatggat   2820
attgaatata acgatatgtt caacaacttt accgtgagct tttggctgcg tgtgccgaaa   2880
gtgagcgcga gccatctgga acagtatggc accaacgaat atagcattat tagcagcatg   2940
aagaaacata gcctgagcat tggcagcggc tggagcgtga gcctgaaagg caacaacctg   3000
atttggaccc tgaaagatag cgcgggcgaa gtgcgtcaga ttacctttcg tgatctgccg   3060
gataagttta acgcgtatct ggcgaacaaa tgggtgttta ttaccattac caacgatcgt   3120
ctgagcagcg cgaacctgta tattaacggc gtgctgatgg gcagcgcgga aattaccggc   3180
ctgggcgcga ttcgtgaaga taacaacatt accctgaaac tggatcgttg caacaataac   3240
aaccagtatg tgagcattga taaatttcgt attttttgca aagcgctgaa cccgaaagaa   3300
attgaaaaac tgtataccag ctatctgagc attacctttc tgcgtgattt ttggggcaac   3360
ccgctgcgtt atgataccga atattatctg attccggtgg cgagcagtag caaagatgtg   3420
cagctgaaga acattaccga ttatatgtat ctgaccaacg cgccgagcta taccaacggc   3480
aaactgaaca tttactatcg tcgtctgtat aacggcctga aattcattat taaacgttat   3540
accccgaata acgaaattga tagctttgtg aaaagcggcg attttattaa actgtatgtg   3600
agctataaca ataacgaaca tattgtgggc tatccgaaag atggcaacgc gtttaataac   3660
ctggatcgta ttctgcgtgt gggctataac gcgccgggca ttccgctgta taagaagatg   3720
gaagcggtga aactgcgtga tctgaaaacc tatagcgtgc agctgaaact gtatgatgat   3780
aagaacgcga gcctgggcct ggttggaacc cataacggtc agattggcaa cgatccaaac   3840
```

-continued cgtgatattc tgattgcgag caactggtat tttaaccatc tgaaagacaa gatcctgggc 3900
tgtgattggt acttcgttcc gacagatgaa ggctggacca acgat 3945

<210> SEQ ID NO 4
<211> LENGTH: 1315
<212> TYPE: PRT
<213> ORGANISM: Clostridium tetani

<400> SEQUENCE: 4

Met Pro Ile Thr Ile Asn Asn Phe Arg Tyr Ser Asp Pro Val Asn Asn
1 5 10 15

Asp Thr Ile Ile Met Met Glu Pro Pro Tyr Cys Lys Gly Leu Asp Ile
20 25 30

Tyr Tyr Lys Ala Phe Lys Ile Thr Asp Arg Ile Trp Ile Val Pro Glu
35 40 45

Arg Tyr Glu Phe Gly Thr Lys Pro Glu Asp Phe Asn Pro Pro Ser Ser
50 55 60

Leu Ile Glu Gly Ala Ser Glu Tyr Tyr Asp Pro Asn Tyr Leu Arg Thr
65 70 75 80

Asp Ser Asp Lys Asp Arg Phe Leu Gln Thr Met Val Lys Leu Phe Asn
85 90 95

Arg Ile Lys Asn Asn Val Ala Gly Glu Ala Leu Leu Asp Lys Ile Ile
100 105 110

Asn Ala Ile Pro Tyr Leu Gly Asn Ser Tyr Ser Leu Leu Asp Lys Phe
115 120 125

Asp Thr Asn Ser Asn Ser Val Ser Phe Asn Leu Leu Glu Gln Asp Pro
130 135 140

Ser Gly Ala Thr Thr Lys Ser Ala Met Leu Thr Asn Leu Ile Ile Phe
145 150 155 160

Gly Pro Gly Pro Val Leu Asn Lys Asn Glu Val Arg Gly Ile Val Leu
165 170 175

Arg Val Asp Asn Lys Asn Tyr Phe Pro Cys Arg Asp Gly Phe Gly Ser
180 185 190

Ile Met Gln Met Ala Phe Cys Pro Glu Tyr Val Pro Thr Phe Asp Asn
195 200 205

Val Ile Glu Asn Ile Thr Ser Leu Thr Ile Gly Lys Ser Lys Tyr Phe
210 215 220

Gln Asp Pro Ala Leu Leu Leu Met His Gln Leu Ile His Val Leu His
225 230 235 240

Gly Leu Tyr Gly Met Gln Val Ser Ser His Glu Ile Ile Pro Ser Lys
245 250 255

Gln Glu Ile Tyr Met Gln His Thr Tyr Pro Ile Ser Ala Glu Glu Leu
260 265 270

Phe Thr Phe Gly Gly Gln Asp Ala Asn Leu Ile Ser Ile Asp Ile Lys
275 280 285

Asn Asp Leu Tyr Glu Lys Thr Leu Asn Asp Tyr Lys Ala Ile Ala Asn
290 295 300

Lys Leu Ser Gln Val Thr Ser Cys Asn Asp Pro Asn Ile Asp Ile Asp
305 310 315 320

Ser Tyr Lys Gln Ile Tyr Gln Gln Lys Tyr Gln Phe Asp Lys Asp Ser
325 330 335

Asn Gly Gln Tyr Ile Val Asn Glu Asp Lys Phe Gln Ile Leu Tyr Asn
340 345 350

Ser Ile Met Tyr Gly Phe Thr Glu Ile Glu Leu Gly Lys Lys Phe Asn

-continued

```
        355                 360                 365

Ile Lys Thr Ala Leu Ser Phe Phe Ser Met Asn His Asp Pro Val Lys
    370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
        435                 440                 445

Arg Glu Asn Leu Tyr Asn Arg Thr Ala Ser Leu Thr Asp Leu Gly Gly
    450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
            500                 505                 510

Ile Val Asp Tyr Asn Leu Gln Ser Lys Ile Thr Leu Pro Asn Asp Arg
        515                 520                 525

Thr Thr Pro Val Thr Lys Gly Ile Pro Tyr Ala Pro Glu Tyr Lys Ser
    530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
        595                 600                 605

Gly Ile Leu Phe Leu Gln Trp Val Arg Asp Ile Ile Asp Asp Phe Thr
    610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
            660                 665                 670

Leu Leu Glu Tyr Ile Pro Glu Ile Thr Leu Pro Val Ile Ala Ala Leu
        675                 680                 685

Ser Ile Ala Glu Ser Ser Thr Gln Lys Glu Lys Ile Ile Lys Thr Ile
    690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
            740                 745                 750

Lys Lys Ile Ile Asp Tyr Glu Tyr Lys Ile Tyr Ser Gly Pro Asp Lys
        755                 760                 765

Glu Gln Ile Ala Asp Glu Ile Asn Asn Leu Lys Asn Lys Leu Glu Glu
    770                 775                 780
```

```
Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
                805                 810                 815

Leu Leu Glu Phe Asp Thr Gln Ser Lys Asn Ile Leu Met Gln Tyr Ile
            820                 825                 830

Lys Ala Asn Ser Lys Phe Ile Gly Ile Thr Glu Leu Lys Lys Leu Glu
        835                 840                 845

Ser Lys Ile Asn Lys Val Phe Ser Thr Pro Ile Pro Phe Ser Tyr Ser
    850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                885                 890                 895

Ser Asp Ile Ser Gly Phe Asn Ser Ser Val Ile Thr Tyr Pro Asp Ala
            900                 905                 910

Gln Leu Val Pro Gly Ile Asn Gly Lys Ala Ile His Leu Val Asn Asn
        915                 920                 925

Glu Ser Ser Glu Val Ile Val His Lys Ala Met Asp Ile Glu Tyr Asn
    930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
                965                 970                 975

Ile Ser Ser Met Lys Lys His Ser Leu Ser Ile Gly Ser Gly Trp Ser
            980                 985                 990

Val Ser Leu Lys Gly Asn Asn Leu  Ile Trp Thr Leu Lys  Asp Ser Ala
        995                 1000                1005

Gly Glu  Val Arg Gln Ile Thr  Phe Arg Asp Leu Pro  Asp Lys Phe
    1010                 1015                 1020

Asn Ala  Tyr Leu Ala Asn Lys  Trp Val Phe Ile Thr  Ile Thr Asn
    1025                 1030                 1035

Asp Arg  Leu Ser Ser Ala Asn  Leu Tyr Ile Asn Gly  Val Leu Met
    1040                 1045                 1050

Gly Ser  Ala Glu Ile Thr Gly  Leu Gly Ala Ile Arg  Glu Asp Asn
    1055                 1060                 1065

Asn Ile  Thr Leu Lys Leu Asp  Arg Cys Asn Asn Asn  Asn Gln Tyr
    1070                 1075                 1080

Val Ser  Ile Asp Lys Phe Arg  Ile Phe Cys Lys Ala  Leu Asn Pro
    1085                 1090                 1095

Lys Glu  Ile Glu Lys Leu Tyr  Thr Ser Tyr Leu Ser  Ile Thr Phe
    1100                 1105                 1110

Leu Arg  Asp Phe Trp Gly Asn  Pro Leu Arg Tyr Asp  Thr Glu Tyr
    1115                 1120                 1125

Tyr Leu  Ile Pro Val Ala Ser  Ser Ser Lys Asp Val  Gln Leu Lys
    1130                 1135                 1140

Asn Ile  Thr Asp Tyr Met Tyr  Leu Thr Asn Ala Pro  Ser Tyr Thr
    1145                 1150                 1155

Asn Gly  Lys Leu Asn Ile Tyr  Tyr Arg Arg Leu Tyr  Asn Gly Leu
    1160                 1165                 1170

Lys Phe  Ile Ile Lys Arg Tyr  Thr Pro Asn Asn Glu  Ile Asp Ser
    1175                 1180                 1185
```

-continued

```
Phe Val  Lys Ser Gly Asp Phe  Ile Lys Leu Tyr Val  Ser Tyr Asn
    1190                 1195                 1200

Asn Asn  Glu His Ile Val Gly  Tyr Pro Lys Asp Gly  Asn Ala Phe
    1205                 1210                 1215

Asn Asn  Leu Asp Arg Ile Leu  Leu Val Gly Tyr Asn  Ala Pro Gly
    1220                 1225                 1230

Ile Pro  Leu Tyr Lys Lys Met  Glu Ala Val Lys Leu  Arg Asp Leu
    1235                 1240                 1245

Lys Thr  Tyr Ser Val Gln Leu  Lys Leu Tyr Asp Asp  Lys Asn Ala
    1250                 1255                 1260

Ser Leu  Gly Leu Val Gly Thr  His Asn Gly Gln Ile  Gly Asn Asp
    1265                 1270                 1275

Pro Asn  Arg Asp Ile Leu Ile  Ala Ser Asn Ala Tyr  Phe Asn His
    1280                 1285                 1290

Leu Lys  Asp Lys Ile Leu Gly  Cys Asp Trp Tyr Phe  Val Pro Thr
    1295                 1300                 1305

Asp Glu  Gly Trp Thr Asn Asp
    1310                 1315


<210> SEQ ID NO 5
<211> LENGTH: 1315
<212> TYPE: PRT
<213> ORGANISM: Clostridium tetani

<400> SEQUENCE: 5

Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
            20                  25                  30

Tyr Tyr Lys Ala Phe Lys Ile Thr Asp Arg Ile Trp Ile Val Pro Glu
        35                  40                  45

Arg Tyr Glu Phe Gly Thr Lys Pro Glu Asp Phe Asn Pro Pro Ser Ser
    50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
        195                 200                 205

Val Ile Glu Asn Ile Thr Ser Leu Thr Ile Gly Lys Ser Lys Tyr Phe
    210                 215                 220

Gln Asp Pro Ala Leu Leu Leu Met His Gln Leu Ile His Val Leu His
225                 230                 235                 240
```

-continued

```
Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
    290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
            340                 345                 350

Ser Ile Met Tyr Gly Phe Thr Glu Ile Glu Leu Gly Lys Lys Phe Asn
        355                 360                 365

Ile Lys Thr Ala Leu Ser Phe Phe Ser Met Asn His Asp Pro Val Lys
    370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
        435                 440                 445

Arg Glu Asn Leu Tyr Asn Arg Thr Ala Ser Leu Thr Asp Leu Gly Gly
    450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
            500                 505                 510

Ile Val Asp Tyr Asn Leu Gln Ser Lys Ile Thr Leu Pro Asn Asp Arg
        515                 520                 525

Thr Thr Pro Val Thr Lys Gly Ile Pro Tyr Ala Pro Glu Tyr Lys Ser
    530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
        595                 600                 605

Gly Ile Leu Phe Leu Gln Trp Val Arg Asp Ile Ile Asp Asp Phe Thr
    610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655
```

-continued

```
Tyr Glu Gly Asn Phe Ile Gly Ala Leu Glu Thr Thr Gly Val Val Leu
            660                 665                 670

Leu Leu Glu Tyr Ile Pro Glu Ile Thr Leu Pro Val Ile Ala Ala Leu
        675                 680                 685

Ser Ile Ala Glu Ser Ser Thr Gln Lys Glu Lys Ile Ile Lys Thr Ile
    690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
            740                 745                 750

Lys Lys Ile Ile Asp Tyr Glu Tyr Lys Ile Tyr Ser Gly Pro Asp Ala
        755                 760                 765

Glu Gln Ile Ala Asp Glu Ile Asn Asn Leu Lys Asn Lys Leu Glu Glu
    770                 775                 780

Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
                805                 810                 815

Leu Leu Glu Phe Asp Thr Gln Ser Lys Asn Ile Leu Met Gln Tyr Ile
            820                 825                 830

Lys Ala Asn Ser Lys Phe Ile Gly Ile Thr Glu Leu Lys Lys Leu Glu
        835                 840                 845

Ser Lys Ile Asn Lys Val Phe Ser Thr Pro Ile Pro Phe Ser Tyr Ser
    850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                885                 890                 895

Ser Asp Ile Ser Gly Phe Asn Ser Ser Val Ile Thr Tyr Pro Asp Ala
            900                 905                 910

Gln Leu Val Pro Gly Ile Asn Gly Lys Ala Ile His Leu Val Asn Asn
        915                 920                 925

Glu Ser Ser Glu Val Ile Val His Lys Ala Met Asp Ile Glu Tyr Asn
    930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
                965                 970                 975

Ile Ser Ser Met Lys Lys His Ser Leu Ser Ile Gly Ser Gly Trp Ser
            980                 985                 990

Val Ser Leu Lys Gly Asn Asn Leu  Ile Trp Thr Leu Lys  Asp Ser Ala
        995                 1000                1005

Gly Glu  Val Arg Gln Ile Thr  Phe Arg Asp Leu Pro  Asp Lys Phe
    1010                 1015                1020

Asn Ala  Tyr Leu Ala Asn Lys  Trp Val Phe Ile Thr  Ile Thr Asn
    1025                 1030                1035

Asp Arg  Leu Ser Ser Ala Asn  Leu Tyr Ile Asn Gly  Val Leu Met
    1040                 1045                1050

Gly Ser  Ala Glu Ile Thr Gly  Leu Gly Ala Ile Arg  Glu Asp Asn
    1055                 1060                1065

Asn Ile  Thr Leu Lys Leu Asp  Arg Cys Asn Asn Asn  Asn Gln Tyr
```

```
    1070                1075                1080

Val Ser  Ile Asp Lys Phe Arg  Ile Phe Cys Lys Ala  Leu Asn Pro
    1085                1090                1095

Lys Glu  Ile Glu Lys Leu Tyr  Thr Ser Tyr Leu Ser  Ile Thr Phe
    1100                1105                1110

Leu Arg  Asp Phe Trp Gly Asn  Pro Leu Arg Tyr Asp  Thr Glu Tyr
    1115                1120                1125

Tyr Leu  Ile Pro Val Ala Ser  Ser Ser Lys Asp Val  Gln Leu Lys
    1130                1135                1140

Asn Ile  Thr Asp Tyr Met Tyr  Leu Thr Asn Ala Pro  Ser Tyr Thr
    1145                1150                1155

Asn Gly  Lys Leu Asn Ile Tyr  Tyr Arg Arg Leu Tyr  Asn Gly Leu
    1160                1165                1170

Lys Phe  Ile Ile Lys Arg Tyr  Thr Pro Asn Asn Glu  Ile Asp Ser
    1175                1180                1185

Phe Val  Lys Ser Gly Asp Phe  Ile Lys Leu Tyr Val  Ser Tyr Asn
    1190                1195                1200

Asn Asn  Glu His Ile Val Gly  Tyr Pro Lys Asp Gly  Asn Ala Phe
    1205                1210                1215

Asn Asn  Leu Asp Arg Ile Leu  Leu Val Gly Tyr Asn  Ala Pro Gly
    1220                1225                1230

Ile Pro  Leu Tyr Lys Lys Met  Glu Ala Val Lys Leu  Arg Asp Leu
    1235                1240                1245

Lys Thr  Tyr Ser Val Gln Leu  Lys Leu Tyr Asp Asp  Lys Asn Ala
    1250                1255                1260

Ser Leu  Gly Leu Val Gly Thr  His Asn Gly Gln Ile  Gly Asn Asp
    1265                1270                1275

Pro Asn  Arg Asp Ile Leu Ile  Ala Ser Asn Ala Tyr  Phe Asn His
    1280                1285                1290

Leu Lys  Asp Lys Ile Leu Gly  Cys Asp Trp Tyr Phe  Val Pro Thr
    1295                1300                1305

Asp Glu  Gly Trp Thr Asn Asp
    1310                1315


<210> SEQ ID NO 6
<211> LENGTH: 1315
<212> TYPE: PRT
<213> ORGANISM: Clostridium tetani

<400> SEQUENCE: 6

Met Pro Ile Thr Ile Asn Asn Phe Arg Tyr Ser Asp Pro Val Asn Asn
1               5                   10                  15

Asp Thr Ile Ile Met Met Glu Pro Pro Ala Cys Lys Gly Leu Asp Ile
            20                  25                  30

Tyr Tyr Lys Ala Phe Lys Ile Thr Asp Arg Ile Trp Ile Val Pro Glu
        35                  40                  45

Arg Tyr Glu Phe Gly Thr Lys Pro Glu Asp Phe Asn Pro Pro Ser Ser
    50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
            100                 105                 110
```

-continued

```
Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
        195                 200                 205

Val Ile Glu Asn Ile Thr Ser Leu Thr Ile Gly Lys Ser Lys Tyr Phe
    210                 215                 220

Gln Asp Pro Ala Leu Leu Leu Met His Gln Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
    290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
            340                 345                 350

Ser Ile Met Tyr Gly Phe Thr Glu Ile Glu Leu Gly Lys Lys Phe Asn
        355                 360                 365

Ile Lys Thr Ala Leu Ser Phe Phe Ser Met Asn His Asp Pro Val Lys
    370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
        435                 440                 445

Arg Glu Asn Leu Tyr Asn Arg Thr Ala Ser Leu Thr Asp Leu Gly Gly
    450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
            500                 505                 510

Ile Val Asp Tyr Asn Leu Gln Ser Lys Ile Thr Leu Pro Asn Asp Arg
        515                 520                 525

Thr Thr Pro Val Thr Lys Gly Ile Pro Tyr Ala Pro Glu Tyr Lys Ser
```

-continued

```
    530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
        595                 600                 605

Gly Ile Leu Phe Leu Gln Trp Val Arg Asp Ile Ile Asp Asp Phe Thr
    610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
            660                 665                 670

Leu Leu Glu Tyr Ile Pro Glu Ile Thr Leu Pro Val Ile Ala Ala Leu
        675                 680                 685

Ser Ile Ala Glu Ser Ser Thr Gln Lys Glu Lys Ile Ile Lys Thr Ile
    690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
            740                 745                 750

Lys Lys Ile Ile Asp Tyr Glu Tyr Lys Ile Tyr Ser Gly Pro Asp Ala
        755                 760                 765

Glu Gln Ile Ala Asp Glu Ile Asn Asn Leu Lys Asn Lys Leu Glu Glu
    770                 775                 780

Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
                805                 810                 815

Leu Leu Glu Phe Asp Thr Gln Ser Lys Asn Ile Leu Met Gln Tyr Ile
            820                 825                 830

Lys Ala Asn Ser Lys Phe Ile Gly Ile Thr Glu Leu Lys Lys Leu Glu
        835                 840                 845

Ser Lys Ile Asn Lys Val Phe Ser Thr Pro Ile Pro Phe Ser Tyr Ser
    850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                885                 890                 895

Ser Asp Ile Ser Gly Phe Asn Ser Ser Val Ile Thr Tyr Pro Asp Ala
            900                 905                 910

Gln Leu Val Pro Gly Ile Asn Gly Lys Ala Ile His Leu Val Asn Asn
        915                 920                 925

Glu Ser Ser Glu Val Ile Val His Lys Ala Met Asp Ile Glu Tyr Asn
    930                 935                 940

Asp Met Phe Asn Asn Phe Thr Val Ser Phe Trp Leu Arg Val Pro Lys
945                 950                 955                 960
```

-continued

Val Ser Ala Ser His Leu Glu Gln Tyr Gly Thr Asn Glu Tyr Ser Ile
965 970 975

Ile Ser Ser Met Lys Lys His Ser Leu Ser Ile Gly Ser Gly Trp Ser
980 985 990

Val Ser Leu Lys Gly Asn Asn Leu Ile Trp Thr Leu Lys Asp Ser Ala
995 1000 1005

Gly Glu Val Arg Gln Ile Thr Phe Arg Asp Leu Pro Asp Lys Phe
1010 1015 1020

Asn Ala Tyr Leu Ala Asn Lys Trp Val Phe Ile Thr Ile Thr Asn
1025 1030 1035

Asp Arg Leu Ser Ser Ala Asn Leu Tyr Ile Asn Gly Val Leu Met
1040 1045 1050

Gly Ser Ala Glu Ile Thr Gly Leu Gly Ala Ile Arg Glu Asp Asn
1055 1060 1065

Asn Ile Thr Leu Lys Leu Asp Arg Cys Asn Asn Asn Asn Gln Tyr
1070 1075 1080

Val Ser Ile Asp Lys Phe Arg Ile Phe Cys Lys Ala Leu Asn Pro
1085 1090 1095

Lys Glu Ile Glu Lys Leu Tyr Thr Ser Tyr Leu Ser Ile Thr Phe
1100 1105 1110

Leu Arg Asp Phe Trp Gly Asn Pro Leu Arg Tyr Asp Thr Glu Tyr
1115 1120 1125

Tyr Leu Ile Pro Val Ala Ser Ser Ser Lys Asp Val Gln Leu Lys
1130 1135 1140

Asn Ile Thr Asp Tyr Met Tyr Leu Thr Asn Ala Pro Ser Tyr Thr
1145 1150 1155

Asn Gly Lys Leu Asn Ile Tyr Tyr Arg Arg Leu Tyr Asn Gly Leu
1160 1165 1170

Lys Phe Ile Ile Lys Arg Tyr Thr Pro Asn Asn Glu Ile Asp Ser
1175 1180 1185

Phe Val Lys Ser Gly Asp Phe Ile Lys Leu Tyr Val Ser Tyr Asn
1190 1195 1200

Asn Asn Glu His Ile Val Gly Tyr Pro Lys Asp Gly Asn Ala Phe
1205 1210 1215

Asn Asn Leu Asp Arg Ile Leu Leu Val Gly Tyr Asn Ala Pro Gly
1220 1225 1230

Ile Pro Leu Tyr Lys Lys Met Glu Ala Val Lys Leu Arg Asp Leu
1235 1240 1245

Lys Thr Tyr Ser Val Gln Leu Lys Leu Tyr Asp Asp Lys Asn Ala
1250 1255 1260

Ser Leu Gly Leu Val Gly Thr His Asn Gly Gln Ile Gly Asn Asp
1265 1270 1275

Pro Asn Arg Asp Ile Leu Ile Ala Ser Asn Ala Tyr Phe Asn His
1280 1285 1290

Leu Lys Asp Lys Ile Leu Gly Cys Asp Trp Tyr Phe Val Pro Thr
1295 1300 1305

Asp Glu Gly Trp Thr Asn Asp
1310 1315

<210> SEQ ID NO 7
<211> LENGTH: 1315
<212> TYPE: PRT
<213> ORGANISM: Clostridium tetani

<400> SEQUENCE: 7

Met Pro Ile Thr Ile Asn Asn Phe Arg Tyr Ser Asp Pro Val Asn Asn
1 5 10 15

Asp Thr Ile Ile Met Met Glu Pro Pro Ala Cys Lys Gly Leu Asp Ile
20 25 30

Tyr Tyr Lys Ala Phe Lys Ile Thr Asp Arg Ile Trp Ile Val Pro Glu
35 40 45

Arg Tyr Glu Phe Gly Thr Lys Pro Glu Asp Phe Asn Pro Pro Ser Ser
50 55 60

Leu Ile Glu Gly Ala Ser Glu Tyr Tyr Asp Pro Asn Tyr Leu Arg Thr
65 70 75 80

Asp Ser Asp Lys Asp Arg Phe Leu Gln Thr Met Val Lys Leu Phe Asn
85 90 95

Arg Ile Lys Asn Asn Val Ala Gly Glu Ala Leu Leu Asp Lys Ile Ile
100 105 110

Asn Ala Ile Pro Tyr Leu Gly Asn Ser Tyr Ser Leu Leu Asp Lys Phe
115 120 125

Asp Thr Asn Ser Asn Ser Val Ser Phe Asn Leu Leu Glu Gln Asp Pro
130 135 140

Ser Gly Ala Thr Thr Lys Ser Ala Met Leu Thr Asn Leu Ile Ile Phe
145 150 155 160

Gly Pro Gly Pro Val Leu Asn Lys Asn Glu Val Arg Gly Ile Val Leu
165 170 175

Arg Val Asp Asn Lys Asn Tyr Phe Pro Cys Arg Asp Gly Phe Gly Ser
180 185 190

Ile Met Gln Met Ala Phe Cys Pro Glu Tyr Val Pro Thr Phe Asp Asn
195 200 205

Val Ile Glu Asn Ile Thr Ser Leu Thr Ile Gly Lys Ser Lys Tyr Phe
210 215 220

Gln Asp Pro Ala Leu Leu Lys Met His Gln Leu Ile His Val Leu His
225 230 235 240

Gly Leu Tyr Gly Met Gln Val Ser Ser His Glu Ile Ile Pro Ser Lys
245 250 255

Gln Glu Ile Tyr Met Gln His Thr Tyr Pro Ile Ser Ala Glu Glu Leu
260 265 270

Phe Thr Phe Gly Gly Gln Asp Ala Asn Leu Ile Ser Ile Asp Ile Lys
275 280 285

Asn Asp Leu Tyr Glu Lys Thr Leu Asn Asp Tyr Lys Ala Ile Ala Asn
290 295 300

Lys Leu Ser Gln Val Thr Ser Cys Asn Asp Pro Asn Ile Asp Ile Asp
305 310 315 320

Ser Tyr Lys Gln Ile Tyr Gln Gln Lys Tyr Gln Phe Asp Lys Asp Ser
325 330 335

Asn Gly Gln Tyr Ile Val Asn Glu Asp Lys Phe Gln Ile Leu Tyr Asn
340 345 350

Ser Ile Met Tyr Gly Phe Thr Glu Ile Glu Leu Gly Lys Lys Phe Asn
355 360 365

Ile Lys Thr Ala Leu Ser Phe Phe Ser Met Asn His Asp Pro Val Lys
370 375 380

Ile Pro Asn Leu Leu Asp Asp Thr Ile Tyr Asn Asp Thr Glu Gly Phe
385 390 395 400

Asn Ile Glu Ser Lys Asp Leu Lys Ser Glu Tyr Lys Gly Gln Asn Met
405 410 415

-continued

```
Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
        435                 440                 445

Arg Glu Asn Leu Tyr Asn Arg Thr Ala Ser Leu Thr Asp Leu Gly Gly
    450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
            500                 505                 510

Ile Val Asp Tyr Asn Leu Gln Ser Lys Ile Thr Leu Pro Asn Asp Arg
        515                 520                 525

Thr Thr Pro Val Thr Lys Gly Ile Pro Tyr Ala Pro Glu Tyr Lys Ser
    530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
        595                 600                 605

Gly Ile Leu Phe Leu Gln Trp Val Arg Asp Ile Ile Asp Asp Phe Thr
    610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
            660                 665                 670

Leu Leu Glu Tyr Ile Pro Glu Ile Thr Leu Pro Val Ile Ala Ala Leu
        675                 680                 685

Ser Ile Ala Glu Ser Ser Thr Gln Lys Glu Lys Ile Ile Lys Thr Ile
    690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
            740                 745                 750

Lys Lys Ile Ile Asp Tyr Glu Tyr Lys Ile Tyr Ser Gly Pro Asp Ala
        755                 760                 765

Glu Gln Ile Ala Asp Glu Ile Asn Asn Leu Lys Asn Lys Leu Glu Glu
    770                 775                 780

Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
                805                 810                 815

Leu Leu Glu Phe Asp Thr Gln Ser Lys Asn Ile Leu Met Gln Tyr Ile
            820                 825                 830
```

-continued

```
Lys Ala Asn Ser Lys Phe Ile Gly Ile Thr Glu Leu Lys Lys Leu Glu
        835                 840                 845

Ser Lys Ile Asn Lys Val Phe Ser Thr Pro Ile Pro Phe Ser Tyr Ser
    850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                885                 890                 895

Ser Asp Ile Ser Gly Phe Asn Ser Ser Val Ile Thr Tyr Pro Asp Ala
            900                 905                 910

Gln Leu Val Pro Gly Ile Asn Gly Lys Ala Ile His Leu Val Asn Asn
        915                 920                 925

Glu Ser Ser Glu Val Ile Val His Lys Ala Met Asp Ile Glu Tyr Asn
    930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
                965                 970                 975

Ile Ser Ser Met Lys Lys His Ser Leu Ser Ile Gly Ser Gly Trp Ser
            980                 985                 990

Val Ser Leu Lys Gly Asn Asn Leu  Ile Trp Thr Leu Lys  Asp Ser Ala
        995                 1000                 1005

Gly Glu  Val Arg Gln Ile Thr  Phe Arg Asp Leu Pro  Asp Lys Phe
    1010                 1015                 1020

Asn Ala  Tyr Leu Ala Asn Lys  Trp Val Phe Ile Thr  Ile Thr Asn
    1025                 1030                 1035

Asp Arg  Leu Ser Ser Ala Asn  Leu Tyr Ile Asn Gly  Val Leu Met
    1040                 1045                 1050

Gly Ser  Ala Glu Ile Thr Gly  Leu Gly Ala Ile Arg  Glu Asp Asn
    1055                 1060                 1065

Asn Ile  Thr Leu Lys Leu Asp  Arg Cys Asn Asn Asn  Asn Gln Tyr
    1070                 1075                 1080

Val Ser  Ile Asp Lys Phe Arg  Ile Phe Cys Lys Ala  Leu Asn Pro
    1085                 1090                 1095

Lys Glu  Ile Glu Lys Leu Tyr  Thr Ser Tyr Leu Ser  Ile Thr Phe
    1100                 1105                 1110

Leu Arg  Asp Phe Trp Gly Asn  Pro Leu Arg Tyr Asp  Thr Glu Tyr
    1115                 1120                 1125

Tyr Leu  Ile Pro Val Ala Ser  Ser Ser Lys Asp Val  Gln Leu Lys
    1130                 1135                 1140

Asn Ile  Thr Asp Tyr Met Tyr  Leu Thr Asn Ala Pro  Ser Tyr Thr
    1145                 1150                 1155

Asn Gly  Lys Leu Asn Ile Tyr  Tyr Arg Arg Leu Tyr  Asn Gly Leu
    1160                 1165                 1170

Lys Phe  Ile Ile Lys Arg Tyr  Thr Pro Asn Asn Glu  Ile Asp Ser
    1175                 1180                 1185

Phe Val  Lys Ser Gly Asp Phe  Ile Lys Leu Tyr Val  Ser Tyr Asn
    1190                 1195                 1200

Asn Asn  Glu His Ile Val Gly  Tyr Pro Lys Asp Gly  Asn Ala Phe
    1205                 1210                 1215

Asn Asn  Leu Asp Arg Ile Leu  Leu Val Gly Tyr Asn  Ala Pro Gly
    1220                 1225                 1230

Ile Pro  Leu Tyr Lys Lys Met  Glu Ala Val Lys Leu  Arg Asp Leu
```

-continued

```
    1235                1240                1245

Lys Thr  Tyr Ser Val Gln Leu  Lys Leu Tyr Asp Asp  Lys Asn Ala
    1250                1255                1260

Ser Leu  Gly Leu Val Gly Thr  His Asn Gly Gln Ile  Gly Asn Asp
    1265                1270                1275

Pro Asn  Arg Asp Ile Leu Ile  Ala Ser Asn Ala Tyr  Phe Asn His
    1280                1285                1290

Leu Lys  Asp Lys Ile Leu Gly  Cys Asp Trp Tyr Phe  Val Pro Thr
    1295                1300                1305

Asp Glu  Gly Trp Thr Asn Asp
    1310                1315
```